United States Patent [19]

Rubinsky et al.

[11] Patent Number: 5,674,218
[45] Date of Patent: Oct. 7, 1997

[54] CRYOSURGICAL INSTRUMENT AND SYSTEM AND METHOD OF CRYOSURGERY

[75] Inventors: Boris Rubinsky, Albany, Calif.; Gary Onik, Wexford, Pa.; J. J. Finkelstein, Washington, D.C.; Dan Neu, Pittsburgh; Steve Jones, Monroeville, both of Pa.

[73] Assignee: Cryomedical Sciences, Inc., Rockville, Md.

[21] Appl. No.: 390,371

[22] Filed: Feb. 16, 1995

Related U.S. Application Data

[63] Continuation of Ser. No. 953,279, Sep. 30, 1992, abandoned, which is a continuation of Ser. No. 588,329, Sep. 26, 1990, abandoned.

[51] Int. Cl.$^6$ .................................................. A61B 17/36
[52] U.S. Cl. .................................................. 606/20; 606/23
[58] Field of Search ........................... 606/22–26, 20; 62/50.1, 50.2, 51.2, 243

[56] References Cited

U.S. PATENT DOCUMENTS

| | | |
|---|---|---|
| 2,319,542 | 5/1943 | Hall . |
| 3,266,492 | 8/1966 | Steinberg . |
| 3,272,203 | 9/1966 | Chato . |
| 3,289,424 | 12/1966 | Shepherd . |
| 3,298,371 | 1/1967 | Lee . |
| 3,398,738 | 8/1968 | Lamb et al. . |
| 3,421,508 | 1/1969 | Nestrock . |
| 3,460,538 | 8/1969 | Armstrong . |
| 3,536,075 | 10/1970 | Thomas, Jr. . |
| 3,542,029 | 11/1970 | Hirschhorn . |
| 3,782,386 | 1/1974 | Barger et al. . |
| 3,859,986 | 1/1975 | Okada et al. . |
| 3,911,924 | 10/1975 | Zimmer . |
| 3,971,383 | 7/1976 | van Gerven . |
| 4,015,606 | 4/1977 | Mitchiner et al. . |
| 4,018,227 | 4/1977 | Wallach . |
| 4,022,215 | 5/1977 | Benson ........................... 606/23 |
| 4,202,336 | 5/1980 | van Gerven . |
| 4,206,760 | 6/1980 | Davis . |
| 4,207,897 | 6/1980 | Lloyd et al. . |
| 4,211,231 | 7/1980 | Rzasa . |
| 4,278,090 | 7/1981 | Van Gerven . |
| 4,280,499 | 7/1981 | Sguazzi . |
| 4,296,610 | 10/1981 | Davis . |
| 4,376,376 | 3/1983 | Gregory . |
| 4,715,187 | 12/1987 | Stearns . |
| 4,716,738 | 1/1988 | Tatge et al. ........................ 62/55 |
| 4,726,194 | 2/1988 | Mackay et al. . |
| 4,831,846 | 5/1989 | Sungaila . |
| 4,924,679 | 5/1990 | Brigham et al. . |
| 4,946,460 | 8/1990 | Merry et al. . |
| 4,949,459 | 8/1990 | Steidl et al. ..................... 62/480 |

Primary Examiner—David M. Shay
Attorney, Agent, or Firm—Sherman and Shalloway

[57] ABSTRACT

An improved cryosurgical system includes means for cooling the cryoprobe instrument to temperatures below the normal boiling point of liquid nitrogen as well as means for recovering the sub-cooled liquid coolant. A unique cryoprobe instrument of simplified construction uses an active vacuum for thermal insulation. Means are provided for controllably adjusting the length of the freezing zone of the cryoprobe to allow the freezing zone to be adjusted for different sizes and shapes of tumors which may be "observed" before surgery by ultrasound imaging. Multiple, disposable cryoprobe instruments can be individually controlled for both operating temperature and freeze zone length. A preferred refrigeration system for sub-cooling liquid nitrogen refrigerant or other cryogenic liquid refrigerant is based on the principles of evaporative cooling.

10 Claims, 26 Drawing Sheets

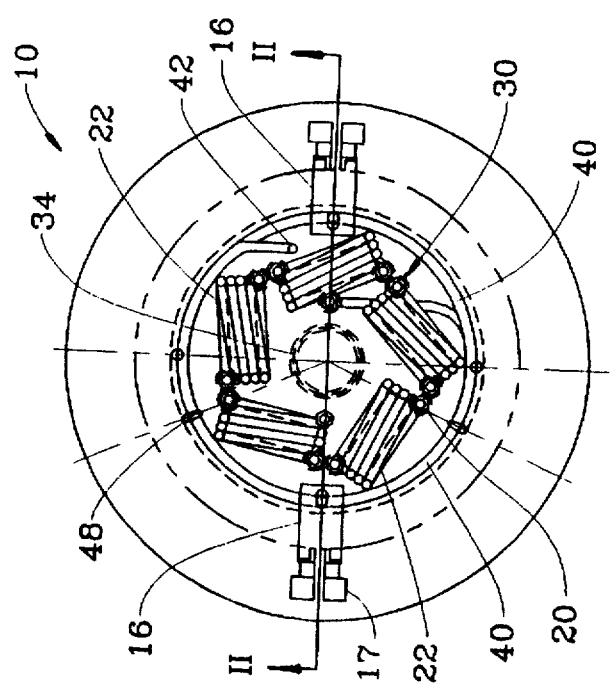

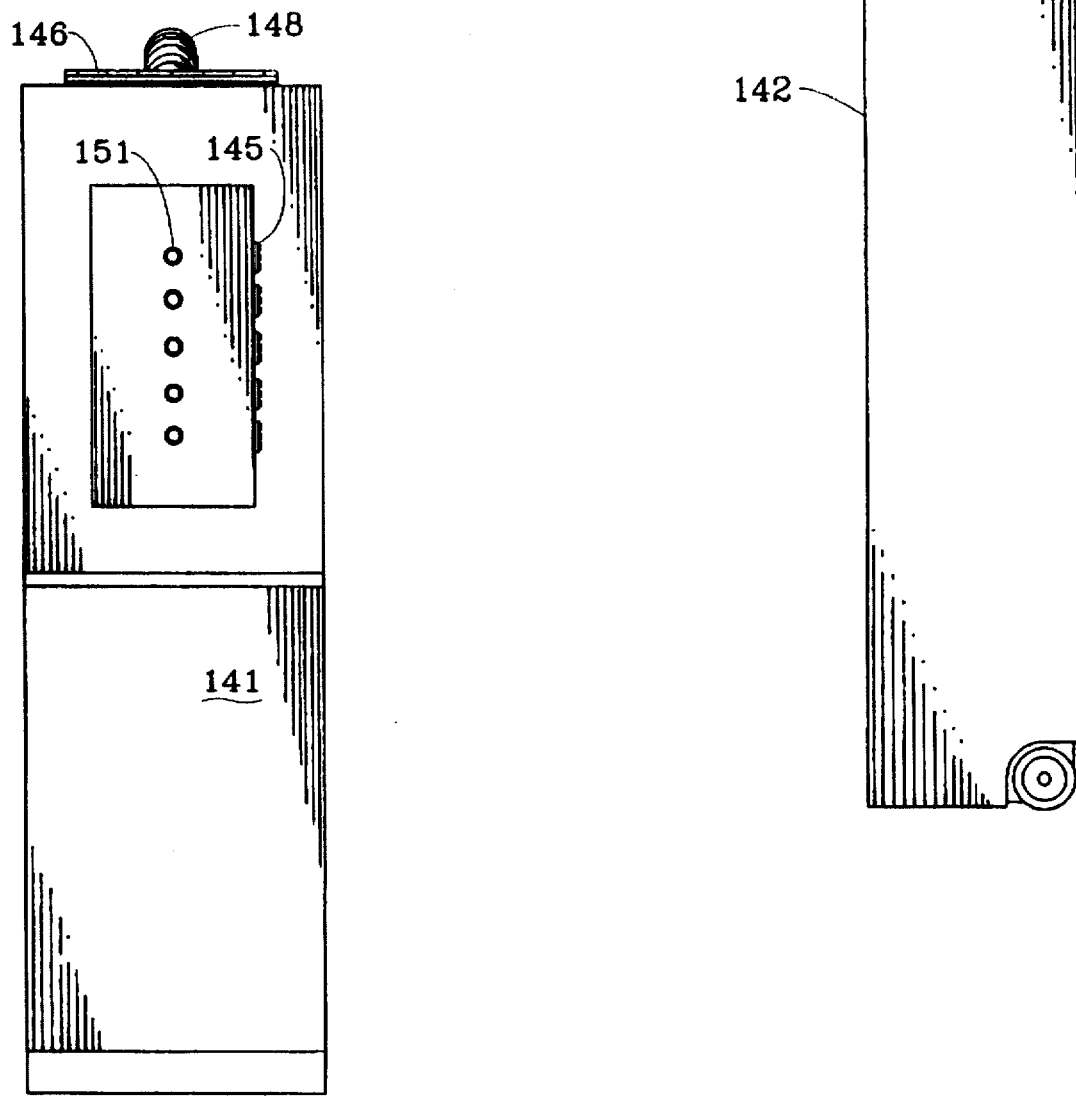

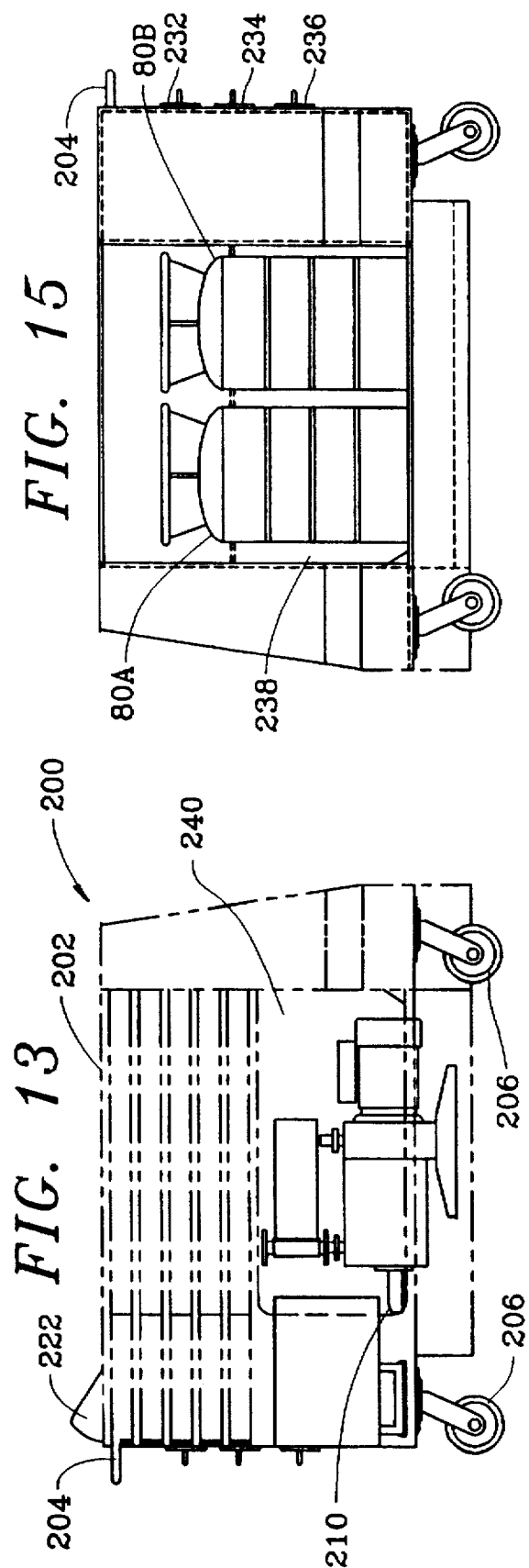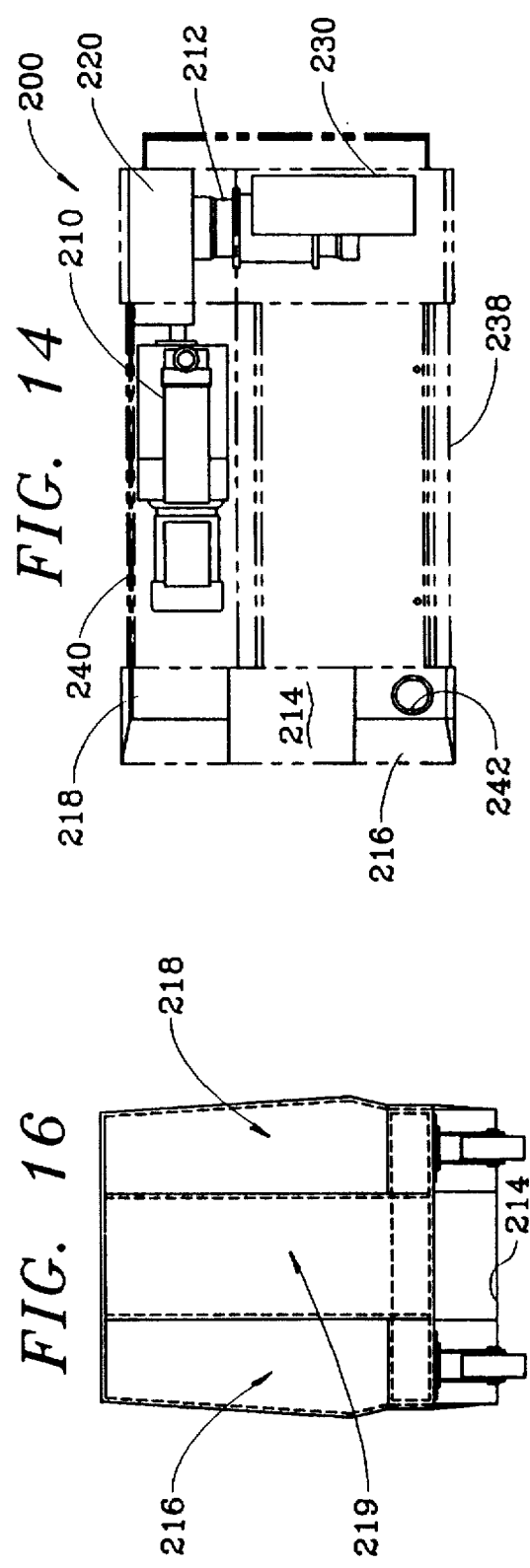

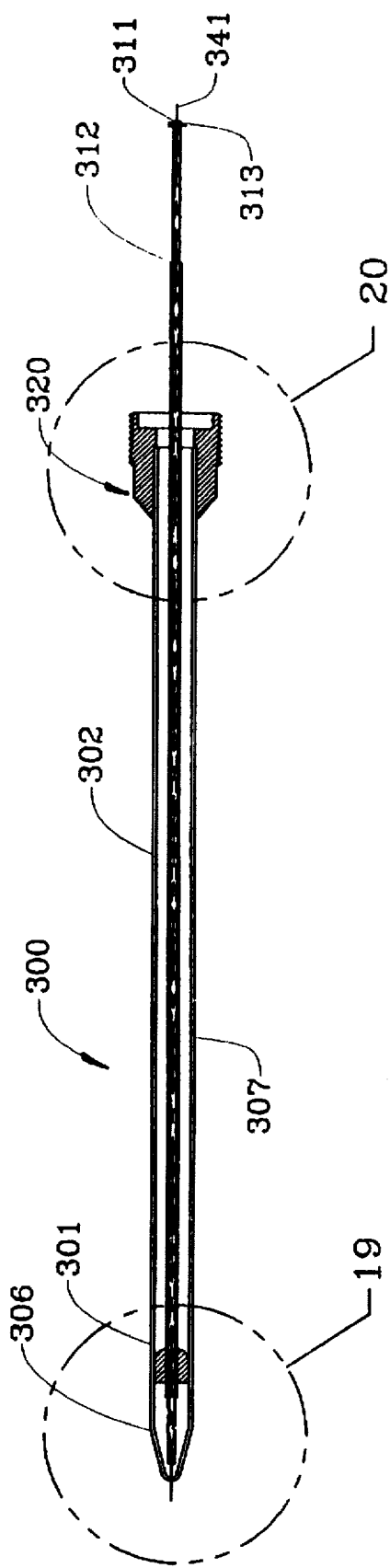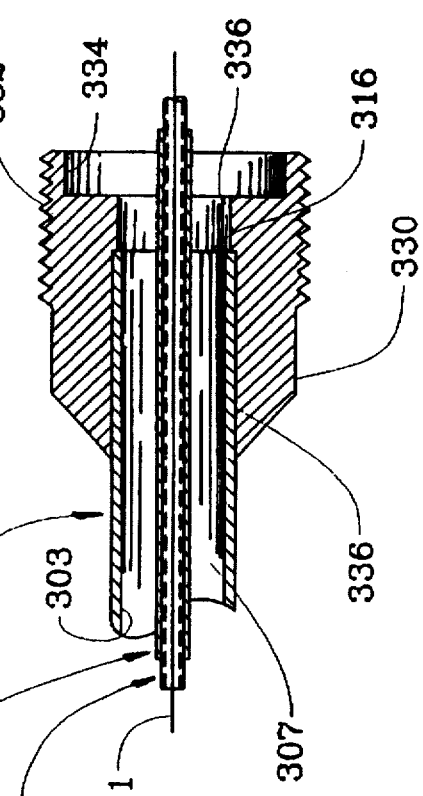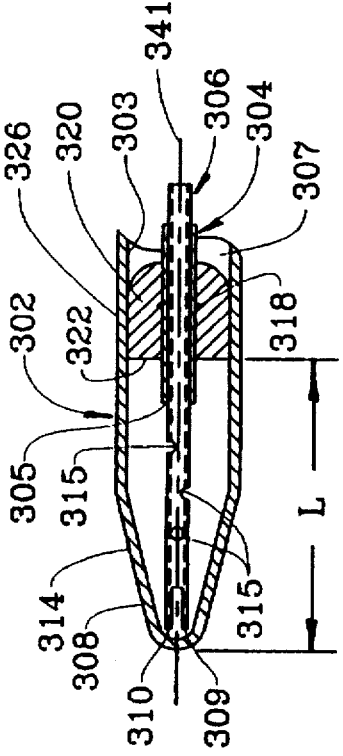
FIG. 18
FIG. 20
FIG. 19

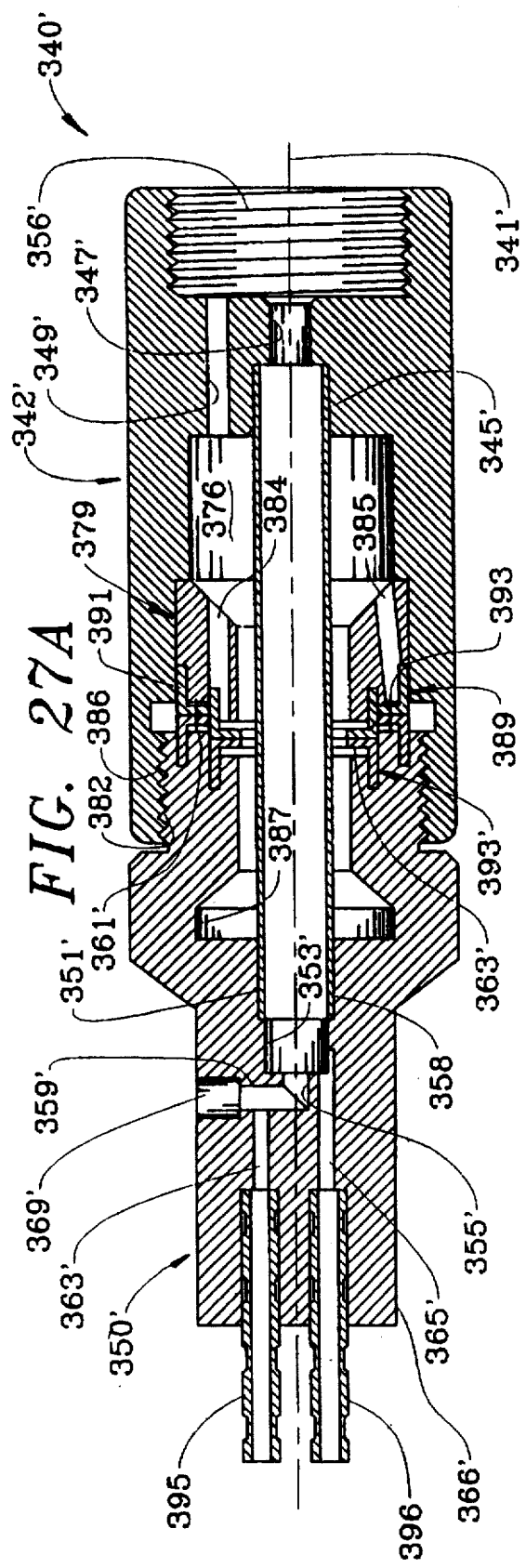
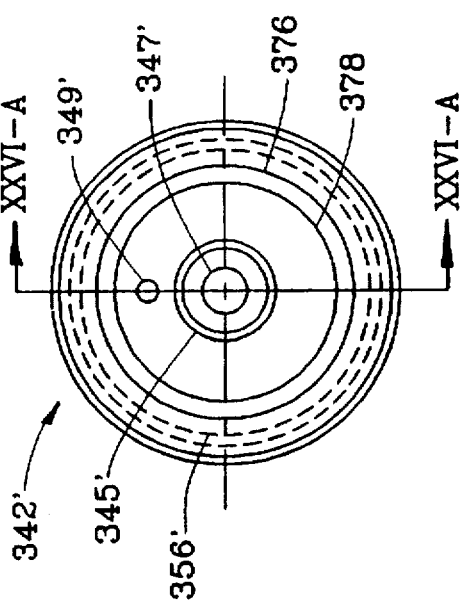

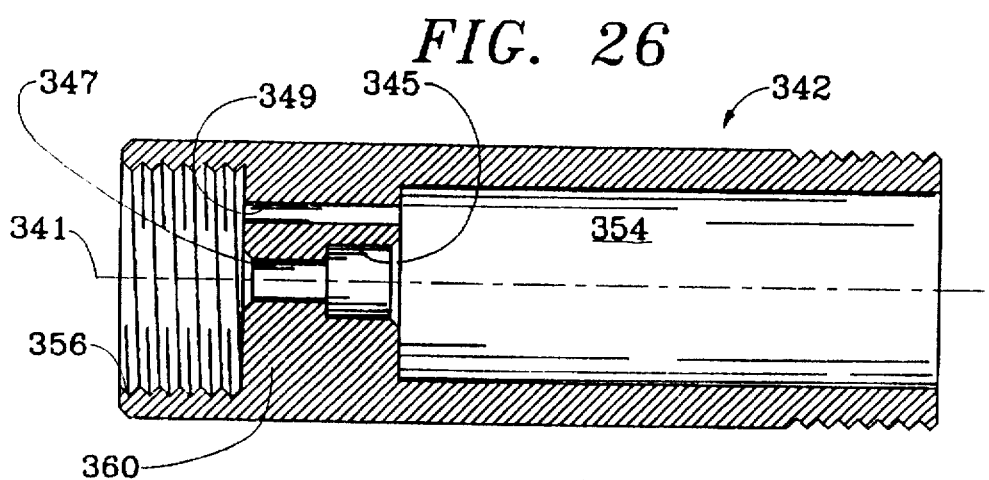
FIG. 26
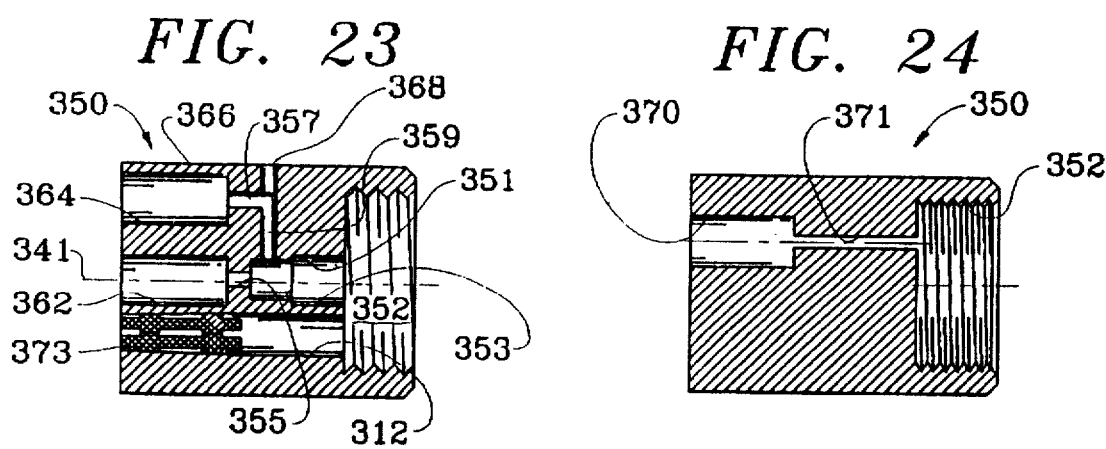
FIG. 23
FIG. 24
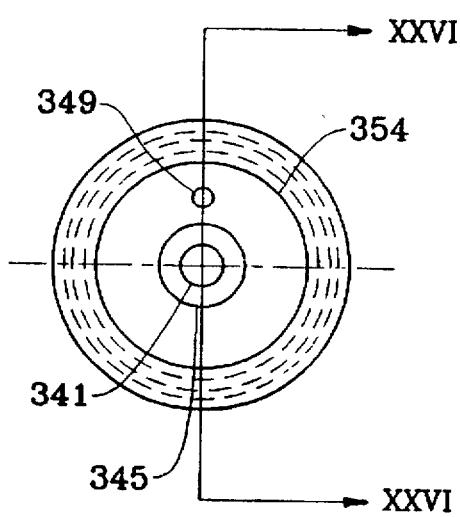
FIG. 22
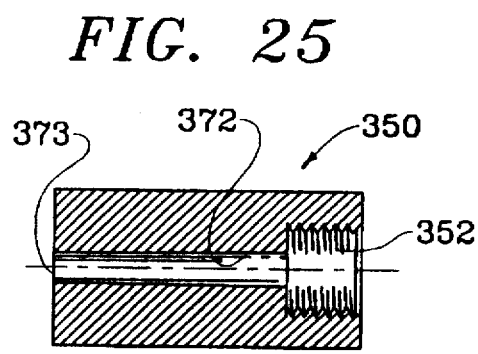
FIG. 25

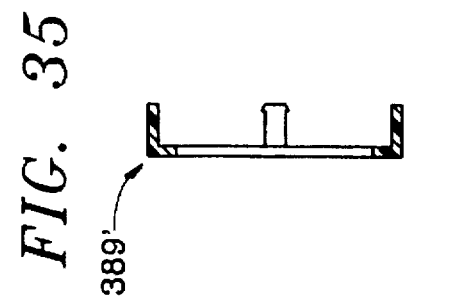
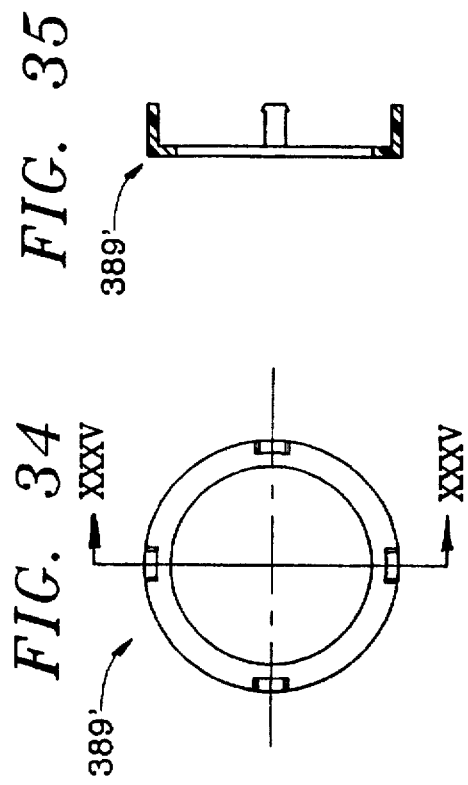
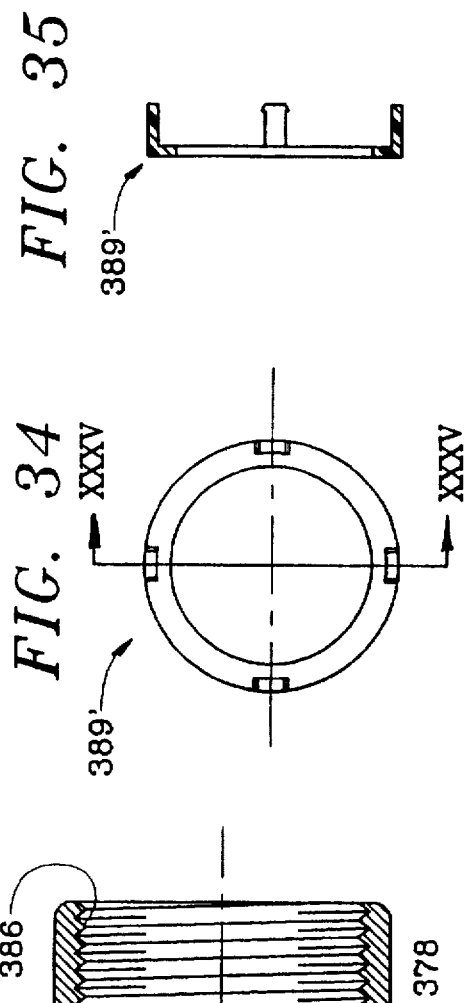
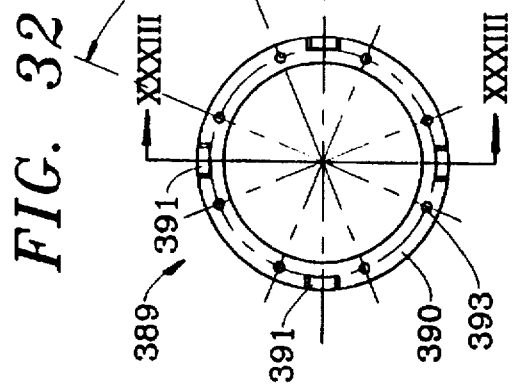
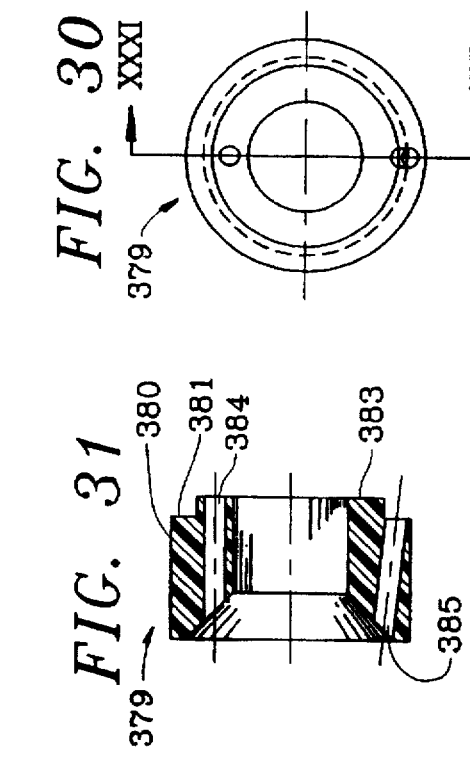
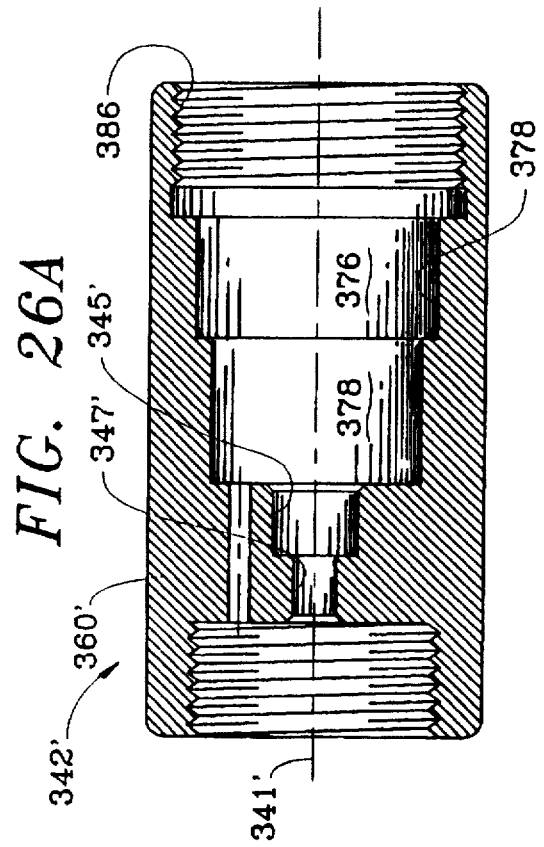

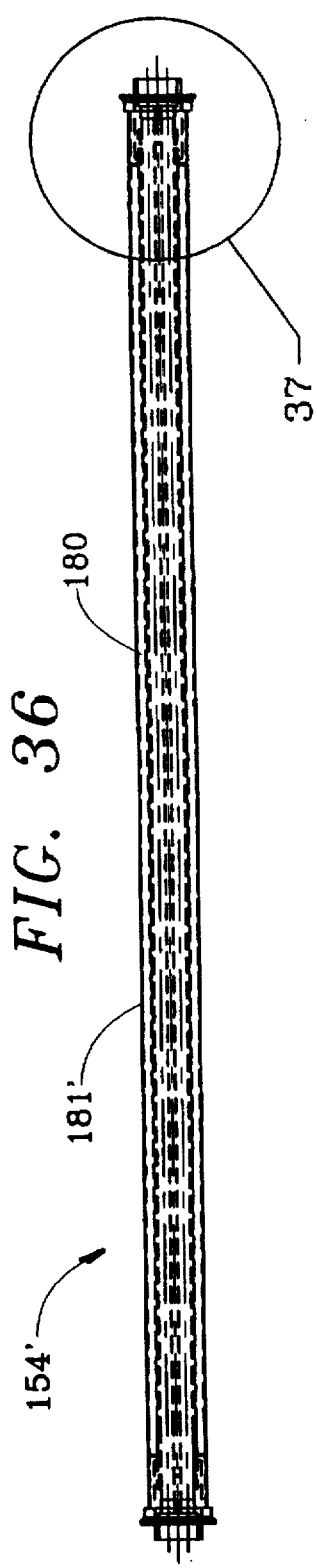
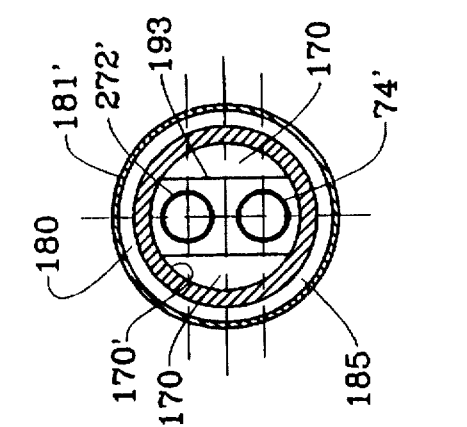
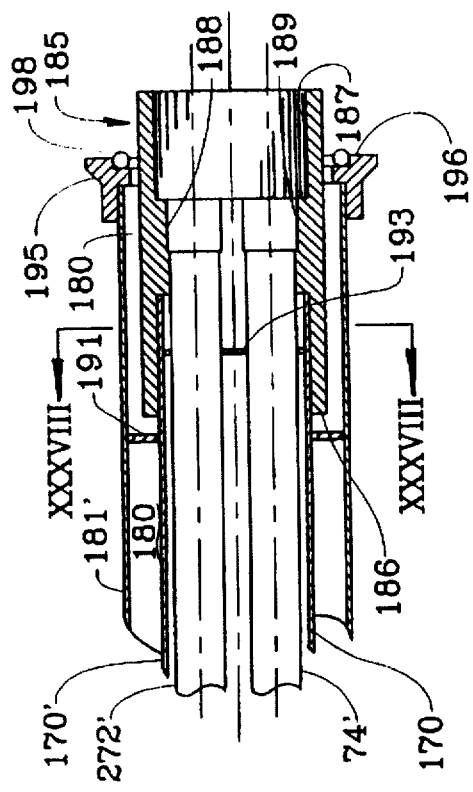
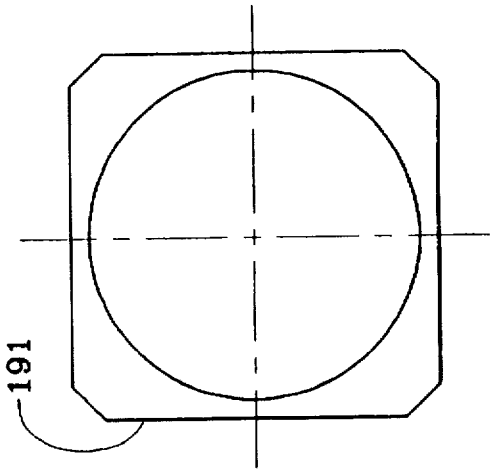

CRYOSURGICAL INSTRUMENT AND SYSTEM AND METHOD OF CRYOSURGERY

This application is a continuation of application Ser. No. 07/953,279, filed Sep. 30, 1992, which in turn is a continuation of application Ser. No. 07/588,329, filed Sep. 26, 1990, both now abandoned.

BACKGROUND OF THE INVENTION

1. Field of Invention

This invention relates to a cryosurgical instrument suitable for use in destroying living tissues, such as solid malignant or benign tumors. More particularly, the invention relates to a surgical system including one or more cryoprobe instruments capable of producing very low temperatures and which is highly effective in the surgical treatment of various disorders, especially for destroying tumors. Even more specifically, the invention relates to a surgical system, including at least one cryoprobe, with means for producing at the probe tip temperatures below the freezing temperature of tissue (−0.57° C.), using liquid nitrogen as the coolant, which coolant temperatures can be lower than the normal boiling temperature of nitrogen. The invention also relates to cryoprobe instruments which have variable controlled active cooling region (freezing zone) as well as cryoprobe instruments and connecting lines with active vacuum thermal insulation, as well as to a cryosurgical operating method in which the surgeon may adjust the freezing zone length in one or more cryoprobe instruments in response to images taken of the tumor prior to or during cryosurgery.

2. Discussion of Prior Art

Cryosurgery is a surgical procedure that uses freezing temperatures to destroy tissue. James Arnott, an English physician, was the first to introduce this method in 1865 for treatment of cancer of the skin. Between 1920 and 1940, the commercialization of liquid air led a number of surgeons to employ freezing to accomplish the destruction of nondesirable tissue. By 1930 the first monograph on the method was published (Lortat-Jacobs and Solente, 1930).

Modern cryosurgery started with the work of a New York surgeon, I. Cooper, who in 1961 developed a new apparatus for cryosurgery. This apparatus consisted of a hollow metal tube which was vacuum insulated, except at the tip, through which liquid nitrogen was circulated. Cooper was able to localize the freezing and, thereby, treat the tissue in a controlled way. The method was used first for treatment of Parkinsonism, and later extended to the destruction of non-desirable tissue in other areas, such as dermatology, proctology, gynecology. The applications of cryosurgery are numerous and have been described in several texts and review papers. (Rand, et al., 1968; Albin 1980; Gage 1982; Zacarian, 1985; Gage, "Cryosurgery For Cancer", Compr. Ther. January 1984; 10(1):61–69; Gage and Torre, 1988; Onik and Rubinsky, 1988).

Until recently, cryosurgery has been applied primarily to treatment of tumors on the outer surface of the body, such as for treatment of skin cancer. Despite the remarkable rate of success with treatment of tumors on the outer surface of the body by cryosurgery (97% survival with treatment of cancer of the skin by cryosurgery, Gage 1982), and despite evidence that cryosurgery may be as efficient deep in the body, (Onik and Rubinsky 1989), the cryosurgery technique is not applied, at this stage, extensively to treatment of nondesirable tissue deep in the body.

Some major problems that hindered the efficient application of cryosurgery to the treatment of cancer and other nondesirable tissue, were that, for example, it had been impossible to observe the extent of the frozen region during cryosurgery, and there was no good understanding of the mechanism by which tissue is destroyed during freezing. Consequently, cryosurgery was typically used for treatment of disease in easily accessible areas, e.g. skin, eyes, nose, where the extent of the frozen tissue could be observed visually.

The prior art devices are, in general, of either of two types, the spray type, wherein the cold refrigerant is sprayed directly onto the tissue to be destroyed, or the closed end cryotip type, in which the refrigerant is delivered to a portion of the tip that is inserted in the tissue to be necrosed. Apparatus described in U.S. Pat. No. 4,376,376 issued to Gregory is exemplary of the spray type devices. The device described in U.S. Pat. No. 4,211,231 includes interchangeable spray and closed end cryotips. Other representative patents disclosing closed end cryotip devices include, for example, U.S. Pat. Nos. 3,971,383—van Gerven; 4,202,336—van Gerven; 3,782,386—Barger, et al.; 3,398,738—Lamb, et al.; 4,015,606—Mitchiner, et al.; 3,859,986—Okada, et al.; 4,831,846—Sungaila. Typical to these prior art devices, which were developed in response to the known science prior to the recent developments of Onik and Rubinsky, is the fact that the extent of the freezing region was not controlled accurately because there was no way to observe the dimension of the tumor and of the tumors deep in the body. Therefore, an accurate control would not have been useful in any event. While the prior art systems were designed to achieve the lowest possible temperature on the closed end tip, as fast as possible, to ensure that as much of the closed end tip (hereinafter often referred to as "freezing zone") as possible reaches as low a temperature as possible, there were, nevertheless, often substantial differences between the temperature of the refrigerant and the temperature of the freezing zone probe tip.

Two major new advances were made recently in the area of cryosurgery. They are reviewed in the paper by Rubinsky and Pegg, Proc., R. Soc. Lond. B234, 343–358 (1988). It was found that monitoring by imaging techniques, such as magnetic resonance imaging or ultrasound, can be used intraoperatively to determine, in real time, the extent of the tumors, as well as that of the frozen tissue during cryosurgery. Ultrasound works by sensing a pressure wave from a pressure transducer. The wave is reflected from boundaries between regions that have differences in acoustic impedance such as between tumors and normal tissue, blood vessels and tissue and frozen and unfrozen tissue. The reflected wave is identified by the pressure transducer and the extent of the tumor, or of the frozen region, is shown on a monitor. Following computerized interpretation of the data, this procedure facilitates an accurate identification of the extent of the tumor and of the frozen region during cryosurgery. Also, recent experiments described in the previously mentioned article by Rubinsky and Pegg, have shed new light on the process of freezing in tissue. The results show that freezing in tissue is strongly affected by the structure of the tissue. Rather, it was shown that ice forms first in the blood vessels, while the cells surrounding the frozen blood vessels remain unfrozen. The rejection of saline during the freezing of the blood vessels causes an increase in the saline concentration in the solution inside the blood vessels. This causes water to leave the unfrozen cells through the cell membrane into the blood vessel. The consequent expansion of the blood vessels leads to the destruction of the vessels. Apparently the destruction of the frozen tissue is promoted by the fact that during freezing the vasculature network is destroyed and, therefore, cancerous and other nondesirable cells in the region that has been frozen are deprived of their blood supply after thawing and die because of ischemic necrosis. It was shown in the same paper that tissue can be destroyed by freezing to temperatures as high as −2° C. Furthermore, it was also shown that this mode of destruction is pronounced at the outer edge of the frozen region. This implies that the image seen on the ultrasound also corresponds to the extent of the frozen region. The work of Rubinsky, et al. also shows that destruction of the vasculature network can be optimized by varying the temperature of the cryosurgical tip in a predetermined controlled way.

The commonly assigned U.S. Pat. No. 4,946,460 of Merry and Smidebush, the disclosure of which is incorporated herein in its entirety by reference thereto, provides a cryosurgical system and method which incorporate these new discoveries by including control means for precisely controlling the heating and cooling of the cryosurgical probe in accordance with a desired temperature regimen.

While good results can be obtained by operating a cryosurgical probe instrument according to predetermined temperature-time profiles, there still remain several problems to be solved before cryosurgical procedures and cryosurgical devices become more readily available to the art.

For example, the new ability to observe, with ultrasound, prior to surgery the extent of the tumor and during surgery the extent of the frozen tissue have raised additional demands from cryosurgical probes that cannot be readily achieved with the available devices. In the past, when the extent of the tumor or of the frozen tissue were not known accurately, the surgeons could not demand that the extent of the frozen region accurately correspond to the tumor. Therefore, prior devices did not have to provide a well specified frozen region to fit the particular tumor that was treated and, in fact, it was impossible to control the performance of prior devices and to determine whether it freezes according to the desire of the surgeon. All that was known was the fact that the temperature at the tip of the cryosurgical probe drops and a certain amount of freezing occurs. Since the surgeons were unable to determine how much freezing occurs, there was no method to determine if the existing devices performed satisfactory or not, neither was there any specific desire to develop devices that can accurately freeze predetermined domains. However, with the clinical application of ultrasound monitoring to cryosurgery, the flaws of the existing devices with respect to the ability to freeze accurately unhealthy, e.g. cancerous, tissue have become evident. The major flaws of the existing devices for clinical practice are related to the minimal temperature that they can achieve and, therefore, to the actual extent of the tissue which they can freeze, and to the extent the actively freezing part of the tip, which in most of the devices is predetermined and, therefore, there is no flexibility in adjusting the extent of the freezing region to the size of the tumor. The new device and system described herein were developed in response to these problems. Furthermore, because of the relative small number of cryosurgeries made in the past, past design requirement for the probes in terms of their ability to handle numerous surgeries were not as stringent as those which the inventors started facing with the increase in the appeal of this procedure and in the number of surgeries performed. Therefore, one of the features of the invention probes is their ability to withstand the rigors of increased use.

It is still often necessary and desirable to be able to achieve probe tip freezing zone temperatures lower than −196° C., the normal boiling point of liquid nitrogen. Lower temperatures can provide higher efficiency in tissue destruction by freezing larger areas with the same probe tip size and geometry, i.e. surface area, or alternatively, the same freezing area with smaller probe tip diameter or surface area.

Most conventional cryosurgical probe instruments operate with liquid nitrogen ($LN_2$) or other liquefied gas as the cooling medium. The $LN_2$ is introduced into the freezing zone of the probe through a feed or delivery tube (which is usually the innermost tube of three concentric tubes). The delivery tube extends into an expansion chamber at the closed probe tip end but terminates a distance from the tip. The $LN_2$ immediately and rapidly vaporizes and undergoes over a one hundred-fold increase in volume. As the liquid vaporizes or gasifies, it absorbs heat from the probe tip to lower its temperature, theoretically to the normal boiling point of $LN_2$ (about −196° C.). However, in actual practice, as the liquid nitrogen boils a thin layer of nitrogen gas [$N_2(g)$] inevitably forms on the inner surface of the closed probe tip end. This gas layer which has a high thermal resistance acts to insulate the probe tip freezing zone such that the outside probe tip temperature does not usually fall below about −160° C. This effect is known as the Liedenfrost effect. Additional inefficiencies result when the back pressures produced by the boiling $LN_2$ reduce the $LN_2$ flow into the freezing zone, thereby further reducing the efficiency of the probe tip to cool. Another problem posed by prior art systems is that the "cold" $N_2(g)$ is simply vented directly to the atmosphere because there is no effective or economical way to recover it. The "cold" vented $N_2(g)$ is not only wasted but produces a cloud of condensate upon exposure to atmospheric moisture in the operating room. While not particularly harmful, it can be unsightly and disconcerting.

Accordingly, one object of this invention is to provide a cryosurgical probe device which can generate probe tip freezing zone temperatures at least as low as the normal boiling temperature of nitrogen.

Another object is to provide a cryosurgical probe device wherein cooling can be effected when desired with a cooling liquid maintained at such temperatures and pressures which avoid or minimize boiling or vaporization of the liquid coolant.

Still another object is to provide a cryosurgical probe device and system which avoids or minimizes venting of "cold" gasified coolant directly to the atmosphere.

Another and related object is to provide a cryosurgical probe instrument and system in which liquid nitrogen refrigerant is recovered after exiting from the cryoprobe and is available for recooling and recirculation.

In order to maintain the low temperatures of the liquid cryogenic refrigerant as the cooling medium flows through the cryoprobe device and also to avoid subfreezing and tissue damaging temperatures on the walls of the cryoprobe device other than the freezing zone of the probe tip almost all known cryoprobe devices will include insulation inside the cryoprobe and surrounding the coolant delivery and return or exit lines downstream of the freezing zone. Most typically the insulation of the probe tip is provided in whole or in part by a permanent or static vacuum downstream of the freezing zone portion of the probe tip which vacuum will also thermally isolate the freezing zone end of the probe tip from the downstream end of the probe tip. For this purpose, the freezing zone and expansion chamber of the probe tip is separated from the downstream end of the probe tip by some form of seal.

However, the requirement for a permanent vacuum substantially increases the cost of the cryoprobe device since it entails very high precision machining and welding of the vacuum seals. For example, the coolant delivery and return tubes need to extend through the seal to communicate with the closed probe tip end and precise machining and welding of these tubes to apertures in the seal and to the probe shell or casing is required. Furthermore, because the cryoprobe device necessarily undergoes cycles of expansion and contraction as the device goes through cooling and heating cycles even the best formed vacuum seals tend to form leaks requiring the entire device to be discarded. At a minimum, this entails very considerable expense, but if the leak occurs during surgery, even more severe problems will obviously arise.

Conventional cryosurgical probes generally have the probe tip permanently affixed to a probe instrument body, including a handle member, for example. See, however, e.g. the aforementioned U.S. Pat. No. 4,211,231, for removable and interchangeable probe tips. In the surgical destruction of tumors by freezing, different size probe tips may be required to treat different sizes and shapes of tumors. However, it is not generally practical or feasible to design or have available probe tips which have the ideal or optimum freezing area/length for every conceivable type of tumor. Therefore, there have been some proposals in the prior art to provide cryosurgical probe devices with means for adjusting the freezing zone by manipulating the length or penetration of the coolant delivery and/or coolant line with respect to the expansion chamber of the probe tip. For example, Lamb, et al. in U.S. Pat. No. 3,398,738, provides a cryosurgical probe in which the liquid refrigerant delivery tube may be longitudinally or axially adjustable with respect to the probe housing. However, the mechanism for making the adjustment is rather complicated. U.S. Pat. No. 4,015,606 to Mitchiner, et al. discloses a cryosurgical probe having a cooling chamber that is permanently separated from the insulating chamber in which a supply conduit extends into the cooling chamber of the probe tip, wherein the freeze zone in the cooling chamber is controlled by adjusting the position of the refrigerant exhaust conduit in the tip relative to the position of the supply conduit. However, only minor, if any, adjustment is available with this device. Furthermore, the problems inherent in permanent vacuum seals still exist.

Accordingly, another object of this invention is to provide a cryoprobe surgical instrument which is comparatively easy and inexpensive to manufacture.

It is another object of the invention to provide a highly efficient cryoprobe surgical instrument which is made from relatively inexpensive parts and construction and which is intended for only a single or few uses and can then be discarded.

A related object is to provide a cryoprobe surgical instrument which does not require a permanent vacuum or high precision seals to thermally isolate the probe body from the probe tip or to insulate the coolant delivery and return lines or tubes from the outside walls of the probe tip other than in the freezing zone at the closed end of the probe tip.

A still further and related object is to provide a cryosurgical probe device and system which includes means for continuously withdrawing gas from the probe tip behind the active freezing zone at the closed end of the probe tip, as well as in the conduits supplying the cryogenic liquid refrigerant to the probe tip, to form and maintain an active or dynamic vacuum to thermally insulate the probe tip and the refrigerant supply lines from the source of the cryogenic coolant to the probe tip.

It is still another object of the invention to provide a cryosurgical probe instrument with a seal which is not permanently fixed to the outer shell or casing of the probe tip but which in operation effectively separates the freezing zone of the probe tip from the remainder of the probe tip, i.e. downstream, with respect to the inflow of coolant liquid, of the seal.

Another object of the present invention is to provide a cryosurgical probe having a simplified but effective means for adjusting the freezing zone of the probe tip by changing the region of insulation relative to the closed end of the probe tip, thereby allowing prior determination of the freezing zone region and thus facilitating the controlled application of cryosurgery to only the regions in which the surgeon determines to freeze the tissue.

Another drawback to conventional cryosurgical instruments is that quite often a tumor is too large or irregularly shaped to be totally destroyed with only a single probe tip and, notwithstanding the use of ultrasonics or other techniques for "observing" the tumor prior to surgery, it often happens that the size and shape of the tumor is not fully recognized until after surgery begins. Also, it is not uncommon for a surgeon to find multiple tumors during surgery. With only a single cryosurgical instrument probe, the surgeon cannot always efficiently or safely treat large, or a larger than expected tumor or multiple tumors. If several cryoprobes are available, it may still be difficult to simultaneously connect more than one probe to the liquid nitrogen source. On the other hand, if a system for connecting multiple probes to the cryogenic refrigerant supply is available, it would still be necessary to have a simple, reliable and safe means for determining which of the several available probes was receiving coolant, which probe tips were at the desired low temperature or sufficiently warmed for being safely removed. It would also be advantageous to be able to individually control the cooling and heating rates of multiple probes and probe tips.

Therefore, it is still another object of the invention to provide a cryosurgical system capable of effectively and safely destroying one or more tumors of varying sizes and shapes using a multiplicity of cryosurgical probes the probe tip temperatures of which can be individually controlled by the surgeon or surgical team member during surgery.

Still yet another object of the invention is to provide a cryosurgical system in which all components required for effectively performing a cryosurgical procedure, including vacuum pump, liquid nitrogen supply, multiple cryosurgical probes, hoses, tubes and other connecting lines, control apparatus and sub-cooling refrigeration system, are contained within a compact movable unit and, all components can be easily and quickly set-up for convenient access by the surgeon and surgical team.

SUMMARY OF THE INVENTION

Accordingly, in a first aspect of the invention, there is provided a surgical system for use in producing very low temperature sufficient to destroy living tissue, the system including a source of cryogenic liquid refrigerant, means for sub-cooling the cryogenic liquid refrigerant, at least one cryosurgical instrument having a hollow probe tip with an opening at one end for receiving liquid refrigerant a second end for freezing living tissue, and a first passageway providing an internal supply line for carrying the liquid refrigerant from the open end to the second end, an external supply line for delivering the sub-cooled liquid refrigerant to the second end of the hollow probe tip through the first passageway, and thermal insulation surrounding at least a portion of the first passageway. The hollow probe tip may be of the spray type, in which case the second end includes an aperture for spraying the refrigerant from the first passageway, but is preferably of the closed end type in which case the second end is closed and the cryosurgical instrument further includes a second passageway providing a return line for carrying the refrigerant from the vicinity of the closed end to outside of the instrument.

In a preferred embodiment of this first aspect, the means for sub-cooling the cryogenic refrigerant, which is preferably liquid nitrogen, is a vacuum operated refrigeration system which includes a source of liquid nitrogen, a vacuum chamber having an inlet for receiving liquid nitrogen from the source, and an outlet for transferring sub-cooled liquid nitrogen to the external supply line, means for drawing a vacuum in the vacuum chamber, a receptacle for storing liquid nitrogen within the vacuum chamber, a heat exchange device within the receptacle connected at one end thereof to the inlet of the vacuum chamber and at the opposite end thereof to the outlet of the vacuum chamber, and a conduit connecting the source of liquid nitrogen to the vacuum chamber inlet, whereby in operation a vacuum is generated in the vacuum chamber to cause liquid nitrogen in the receptacle to form sub-cooled liquid nitrogen, such that liquid nitrogen flowing through the heat exchange device in heat exchange contact with the sub-cooled liquid nitrogen has its temperature lowered to below the normal boiling temperature of nitrogen.

In accordance with another preferred embodiment of this aspect of the invention, the system also includes means for continuously withdrawing gas from the cryosurgical instrument's hollow probe tip surrounding the first passageway to form and maintain an active vacuum in the probe tip to thermally insulate the first passageway.

In a second aspect of the invention, there is provided a cryosurgical probe tip having a closed end with a selectively adjustable active freeze zone at the closed end of the probe tip. The probe tip includes a hollow shell or casing having an open end and a closed end, a first flow passageway extending through the open end to the vicinity of the closed end of the hollow shell for transporting cryogenic liquid refrigerant to the vicinity of the closed end, a second flow passageway extending from the vicinity of the closed end for removing refrigerant from the closed end through the outlet opening, sealing means for separating the closed end of the hollow shell from the open end of the hollow shell and defining on the closed end side thereof a probe tip freeze zone. The first and second flow passageways extend through the sealing means, the latter being affixed to at least the second flow passageway, such that longitudinal movement of the second flow passageway will cause corresponding movement of the sealing means with respect to the closed end, and means for providing thermal insulation behind the sealing means in the hollow shell, whereby the sealing means prevents fluid flow of the cryogenic refrigerant from the probe tip freeze zone except through the second passageway.

The thermal insulation may be provided by air or other gas, vacuum, or compressible solid thermal insulating material.

According to this second aspect of the invention, a cryosurgical instrument includes the probe tip with selectively adjustable freeze zone and an instrument body for connecting the probe tip to cryogenic liquid refrigerant delivery line and refrigerant exhaust line and also for providing handle means for the probe tip. The instrument body will include a first inlet for receiving cryogenic liquid refrigerant and a first outlet for removing cryogenic refrigerant, a refrigerant flow passageway for transporting cryogenic liquid refrigerant from the first inlet through the instrument body to the first flow passageway of the probe tip, an exhaust flow passageway for transporting refrigerant from the second flow passageway through the instrument body to the first outlet, and connecting means for fluid tightly receiving the open end of the hollow shell. The cryosurgical instrument may also include a temperature sensing device for measuring the temperature at the freezing zone and electrical conductors extending through the instrument body and probe tip connected to the temperature sensing device for relaying the measured temperature to means for controlling the temperature in the freezing zone.

According to one preferred embodiment of this second aspect of the invention, the means for providing thermal insulation comprises means for continuously withdrawing gas from the hollow probe shell behind the sealing means to create an active vacuum thermal insulation surrounding the first and second flow passageways in the probe tip and preferably also in the instrument body. According to this embodiment, there may be provided a cryosurgical instrument having a hollow, probe shell having an open end and a closed face at the opposite end, an instrument body having a first inlet for receiving cryogenic liquid refrigerant, a first outlet for removing cryogenic refrigerant, a second outlet for withdrawing gas from the instrument body, a portion having a vacuum chamber at one end thereof in communication with the second outlet, the opposed end of the portion including means for receiving the hollow cryosurgical probe shell, a channel connecting the vacuum chamber and the receiving means, a first flow passageway for transporting cryogenic liquid refrigerant from the first inlet through the vacuum chamber to the vicinity of the closed end of said probe shell through the vacuum chamber and back to the first outlet, means forming a selectively movable seal within the hollow shell spaced from the closed end thereof and defining on the closed tip end side thereof an adjustable freeze zone, and at the open end of the probe shell means for mating with the receiving means, such that with the probe shell connected to the instrument body, the interior of the hollow shell up to the movable seal means is in flow communication with the vacuum chamber via the channel, and the first and second flow passageways extend through the seal means into the adjustable freeze zone, the movable seal means preventing fluid flow from the freeze zone except through the second passageway.

According to this preferred embodiment, there may also be provided means for continuously withdrawing gas from the hollow shell thereby actively generating a vacuum within the cryosurgical instrument, whereby the vacuum provides the thermal insulation for the first and second flow passageways in the probe tip and in the instrument body. Furthermore, the means for continuously withdrawing gas to actively generate a vacuum may comprise a vacuum pump and a conduit connecting the vacuum pump to the second outlet of the instrument body. Alternatively, the gas withdrawing means may comprise a rapidly flowing fluid in flow communication with the vacuum chamber thereby withdrawing gas by aspiration.

The present invention also contemplates a cryosurgical instrument with a fixed length freeze zone or non-movable sealing means between the closed end of the probe casing and the open end of the probe casing and which includes means for continuously withdrawing gas from the hollow probe casing to thereby actively generate a vacuum within the cryosurgical instrument to provide thermal insulation to prevent the cryogenic liquid refrigerant flowing through the probe casing to the closed end from freezing the walls of the hollow casing other than in the freeze zone.

For example, the present invention provides in a third aspect thereof an improvement in a cryosurgical instrument which includes an instrument body, a hollow probe casing having an open end and a closed end protruding from the instrument body, vacuum seal means for separating the closed end from the open end, and defining a probe freezing zone at the closed end of the hollow probe casing for receiving a cryogenic liquid refrigerant and a thermally insulating vacuum zone at the open end, a refrigerant supply conduit extending through the instrument body and casing and through the vacuum seal means into the probe freezing zone for supplying refrigerant to the freezing zone, a refrigerant exhaust conduit extending from the freezing zone through the vacuum seal means and through the casing and instrument body for withdrawing refrigerant from the probe freezing zone, the improvement being provided by means for continuously withdrawing gas from the casing and instrument body for generating an active vacuum within the thermally insulating vacuum zone while refrigerant is being supplied to the probe freezing zone via the supply conduit, the vacuum providing thermal insulation for refrigerant flowing through the supply conduit and exhaust conduit in the thermally insulating vacuum zone.

Accordingly to a fourth aspect of the invention, a novel cryosurgical system for destroying tumors by freezing is provided. The system includes at least one source of cryogenic liquid refrigerant, a multiplicity of cryoprobe instruments, supply conduit means connecting the at least one source to each of the multiplicity of instruments, first control means for directing flow of liquid refrigerant from the at least one source via the supply conduit means to only preselected ones of the multiplicity of instruments to cryogenically activate the preselected ones, second control means for controlling the temperature of each cryogenically activated cryoprobe instrument independently of the temperature of any other cryogenically activated cryoprobe instrument, and display means for displaying which of the preselected ones of the multiplicity of instruments is receiving liquid refrigerant, and for displaying the temperature of each preselected one, whereby only one or a multiplicity of the cryoprobe instruments may be activated to simultaneously freeze different portions of a tumor to facilitate total destruction thereof and/or simultaneously freeze at least one portion each of two or more tumors in the same patient.

In one preferred embodiment of this aspect, the at least one source of cryogenic liquid refrigerant includes means for sub-cooling the cryogenic liquid refrigerant, especially liquid nitrogen.

In another preferred embodiment of this aspect there are additionally provided two or more interchangeable probe tips of different size, configuration or both, each of the tips being adapted to be fitted on any one of the multiplicity of cryoprobe instruments.

In still another advantageous embodiment of the invention, means are provided for continuously withdrawing gas from the supply conduit and, optionally, from the cryoprobe instrument, to maintain an active vacuum for thermally insulating cryogenic refrigerant flowing through at least the supply conduit.

Still another advantageous embodiment of the invention, used in combination with the means for sub-cooling the cryogenic liquid refrigerant, includes an at least partially closed refrigeration cycle for recovering sub-cooled liquid cryogen from a cryoprobe instrument to a liquid refrigerant collection means, whereby the recovered liquid cryogenic refrigerant can be recycled to a cryosurgical instrument.

The closed loop cycle for recovering and reusing sub-cooled liquid nitrogen or other sub-cooled liquid nitrogen or other sub-cooled liquid cryogen may include, according to one specific embodiment, first and second insulated vessels for receiving, storing and delivering liquid nitrogen or other liquid cryogenic refrigerant, valve means for selectively connecting the first and second vessels to the means for sub-cooling the liquid nitrogen or other cryogenic liquid coolant, measuring means for detecting the amount of liquid nitrogen or other liquid cryogen in the first and second vessels, and valve actuation means for activating the valve means in response to the measuring means, whereby, during operation of the cryosurgical system, upon detection by the measuring means of an amount at or below a predetermined amount of liquid nitrogen in whichever of the first and second vessels is connected by the valve means to the means for generating sub-cooled liquid nitrogen or other cryogenic liquid refrigerant, the valve actuation means can be activated to connect the valve means from the vessel in which the low amount of liquid nitrogen or other liquid cryogen was detected to the other vessel.

The system may further preferably include return conduit means for returning used liquid nitrogen or other cryogenic liquid from the cryogenically activated preselected ones of the multiplicity of cryoprobe instruments to whichever of the first and second vessels is not connected by the valve means to the means for generating sub-cooled liquid nitrogen or other cryogenic liquid refrigerant.

A fifth aspect of the invention is a method for more efficiently cryosurgically destroying a tumor or tumors deep in the body, e.g. associated with an internal body organ, such as liver, colon, prostate, kidney, etc. According to the method of this invention, the surgeon, prior to surgery, obtains a visual image of the tumor or tumors using an imaging technique, such as magnetic resonance imaging, ultrasound, and the like, to determine the size and shape of the tumor or tumors, and based on the observed images, the surgeon selects one or more cryosurgical instruments having adjustable freeze zone lengths and probe tip diameters and shapes, and adjusts the freeze zone length of at least one cryosurgical instrument in accordance with the observed image of a tumor to correspond to at least one major dimension of the tumor, and inserting the at least one cryosurgical instrument with adjusted freezing zone length into the tumor whereby the adjusted freezing zone length will correspond to a major dimension of the tumor.

The invention will now be described in greater detail by way of specific, non-limiting embodiments, and with the assistance of the accompanying drawings.

BRIEF DESCRIPTION OF THE DRAWINGS

FIG. 1 is a top plan view, with the cover shown in phantom to provide an internal view, of an embodiment of a vacuum chamber for generating sub-cooled liquid refrigerant by indirect evaporative cooling according to the invention;

FIG. 2 is a section view along line II—II of the vacuum chamber of FIG. 1;

FIG. 7-A is a simplified schematic flow diagram of a direct evaporative cooling refrigeration system with modified liquid nitrogen recovery system;

FIG. 7-B is a simplified schematic flow diagram of a modified direct evaporative cooling refrigeration system using a single vessel for generating sub-cooled liquid nitrogen and recovering used liquid nitrogen;

FIG. 8-A is a simplified schematic flow diagram similar to FIG. 8 for a modified form of the delivery lines between the cryoprobe instruments and the refrigeration system;

FIG. 11 is a front view of the mobile manifold assembly of FIG. 10;

FIG. 12 is a side elevation view of the mobile manifold assembly of FIG. 10 showing the control console arm in its operative position;

FIG. 13 is a right side elevation view with side panel shown in phantom, of an embodiment of a mobil cart according to the invention for storing and transporting the pressurized liquid nitrogen supply vessels, mobile manifold, vacuum pump, optional control and computer components, and associated tubing, with the vacuum pump exposed behind the missing side panel;

FIG. 14 is a top plan view of the mobile cart assembly of FIG. 13 with a portion of the top panels shown in phantom;

FIG. 15 is a left side elevation view of the mobile cart of FIG. 13, with a portion of the right side panel broken away to show a pressurized liquid nitrogen supply vessel;

FIG. 16 is a front elevation view of the mobile cart of FIG. 13;

FIG. 17-A is a perspective view of a modified embodiment of a mobile cart with integrally mounted pivotable manifold arm;

FIG. 18-A is a sectional side elevation view of a modified embodiment of a cryosurgical probe tip with enlarged flat end and fixed seal member;

FIG. 18-B a side elevation view, in section, of an alternative embodiment of a probe tip according to the invention, including a crimpable seal member;

FIG. 19 is an enlarged side sectional view of the movable seal member and freezing zone portion of the probe tip shown by broken section line "A" in FIG. 18;

FIG. 20 is an enlarged side sectional view of the probe base at the open end of the probe tip shown by broken section line "B" in FIG. 18;

FIGS. 21-A is a rear end view of another embodiment of a delivery tube connector according to the invention;

FIG. 22 is an end view of an embodiment of a probe connector according to the invention;

FIG. 22-A is an end view of a modified embodiment of a probe connector according to the invention;

FIG. 23-A is a section view along line XXIII-A—XXIII-A of FIG. 21-A;

FIG. 24-A is a section view along line XXIV-A—XXIV-A of FIG. 21-A.

FIG. 25 is a section view along line XXV—XXV of FIG. 21;

FIG. 26 is a section view along line XXVI—XXVI of the probe connector shown in FIG. 22;

FIG. 26-A is a section view along line XXVIA—XXVIA of the probe connector shown in FIG. 22-A;

FIG. 27-A is a side elevation view of another embodiment of a probe instrument body according to the invention, including the probe connector of FIG. 26-A joined to the modified embodiment of the delivery tube connector of FIG. 21-A;

FIG. 30 is an end view of the probe connector insert shown in FIG. 27-A;

FIG. 31 is a section view along line XXXI—XXXI of FIG. 30;

FIG. 32 is an elevation view of a thermocouple electrical connector for the probe connector shown in FIG. 27-A;

FIG. 33 is a section view along line XXXIII—XXXIII of FIG. 32;

FIG. 34 is an elevation view of a thermocouple electrical connector for the delivery tube connector of FIG. 27-A;

FIG. 35 is a section view along line XXXV—XXXV of FIG. 34;

FIG. 36 is a side elevation view, partially in section, of vacuum insulated cryogenic refrigerant supply tube section according to the invention with identical female couplings at both end;

FIG. 37 is an enlarged side sectional view showing the details at end section XXXVII of one end of the supply tube section of FIG. 36;

FIG. 38 is a sectional view along line XXXVIII—XXXVIII of FIG. 36;

FIG. 42 is an elevation view of the large spacer used in the supply tube sections shown in FIGS. 30 and 33.

DETAILED DESCRIPTION OF PREFERRED EMBODIMENTS

Figure 3:
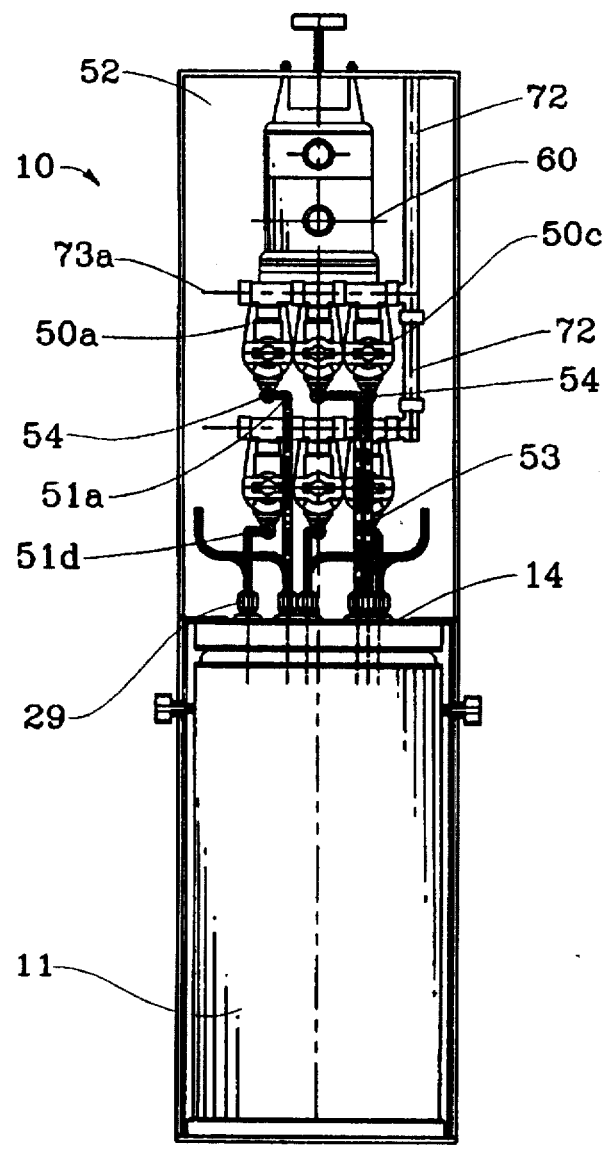
FIG. 3 is a front elevation view showing an embodiment of a heat exchanger valve assembly and optional manifold mounting plate for the vacuum chamber of FIG. 1.

The present invention cryogenic surgical system, considering all of its various aspects, is essentially a self-contained system for performing cryosurgery, i.e. surgery relying on sub-freezing temperatures to destroy unhealthy or undesired tissues and organs, including, in particular, various types of solid benign or malignant tumors. This system itself may include several major subsystems, each of which incorporates one or more unique components, and each of which would be useful independently of the other subsystems. By providing a self-contained system with easily assembled and disassembled parts and components, designed into a compact transportable unit, substantial convenience for the surgeon and operating room personnel and hospital is accomplished.

More particularly, the cryogenic surgical system may include the following major subsystems: (A) a refrigeration system for generating sub-cooled liquid refrigerant (e.g. liquid nitrogen); (B) a main console unit for storing and transporting various components of the system, including a control system for independently controlling the supply of cryogenic liquid refrigerant to one or more cryosurgical probe instruments; (C) a system for evacuating gas from a cryosurgical probe, as well as from the supply and delivery lines to the cryosurgical probe; (D) a movable seal to adjust the length of the freezing zone and insulated region of the probe; and (E) multiple inter-changeable, cryosurgical probe instruments. Other major components of the system may include (F) active vacuum insulated delivery and supply tubing for transporting the sub-cooled liquid refrigerant to and from the sub-cooling refrigeration system, and cryosurgical probe instrument(s).

For convenience, the following discussion will refer to liquid nitrogen as the operative refrigerant material, since in practice it is contemplated that liquid nitrogen which is readily available commercially and in many hospital surgical operating rooms and is economical and generates very low temperatures, will be the cryogenic refrigerant of choice. However, it is understood that other liquid refrigerants capable of generating subfreezing temperatures, preferably with boiling points below about $-20°$ C., especially below $-60°$ C., can also be used. Examples of such cryogenic liquid refrigerant materials include, for example, freon 14 (freezing point 128° K, boiling point 145° K); freon 22 (boiling point 233° K); freon 13 (boiling point 192° K); liquefied air, normally gaseous hydrocarbons, such as propane and isobutane, helium, argon, etc.

As used herein and in the appended claims, the term "sub-cooled" or "sub-cooling" in reference to the cryogenic liquid refrigerant means that the temperature of the cryogenic liquid is lowered below its normal boiling point ($-195.8°$ C. for nitrogen) and generally above its normal freezing point ($-210°$ C. for nitrogen). In the present invention, the sub-cooled liquid nitrogen refrigerant will generally be at a temperature ranging from about $-198°$ C. to $-210°$ C., preferably, from about $-200°$ to $-208°$ C., especially about $-208°$ C., as it leaves the refrigeration system in which the sub-cooling takes place. Therefore, by maintaining appropriate flow rates and shortening the distance between the refrigeration system and the cryosurgical probe(s) as much as possible, generally within 8 to 10 feet, especially within 4 to 6 feet, probe tip operating temperatures below the normal boiling point of the liquid nitrogen ($LN_2$), i.e. below about $-196°$ C., can be achieved and maintained. However, and this is also within the scope of the invention, by controlling the flow rate or intermittently interrupting the flow of the cryogenic liquid, the temperature at the freezing zone of the probe tip can be easily controlled to provide higher operating temperatures, for instance to achieve the operating temperature profiles, such as described in the aforementioned U.S. Pat. No. 4,946,460. It is also within the scope of the invention to include heating means for warming the probe tip, for instance to facilitate removal of the probe tip from the frozen tissue or organ at the conclusion of or during the surgical procedure. For example, a source of heated air or heated nitrogen gas can be used to raise the probe tip temperature to as high as about 37° C. (98.6° F.) or more, including, if desired, temperature for cauterizing the blood vessels in contact with the probe tip. Alternatively, internal or external heating coils such as known in the prior art can be provided, although this technique will generally involve higher manufacturing or assembly costs.

In the present invention, the system for generating sub-cooled liquid nitrogen may be conveniently housed in a mobile manifold unit or in a mobile cart storage and supply unit.

The mobile manifold unit can provide several functions. These include (1) storage at a location close to the patient of the refrigeration system and heat exchanger valve (manifold) assembly to allow selective and independent control of the temperature of the $LN_2$ cryogenic refrigerant for one or more cryosurgical probes; (2) providing a control panel that is easily accessible and close to the operating physician; (3) providing means for selectively raising the probe temperature for one or more cryosurgical probes for thawing and/or cauterizing; (4) providing a connection point that is close to the patient.

Such mobile manifold assembly may be shaped as a substantially vertical column, which may have a rectangular, square, polygonal or circular cross-section, including a wheeled base, a removal front panel to provide access to the refrigeration system, and valve manifold assembly, as well as associated plumbing, wiring or other utilities. The mobile manifold may also have externally mounted at a convenient and accessible location thereon, such as its top (upper) surface or ledge a temperature display and control panel for displaying the temperature and for independently controlling the temperature set point of one or more cryoprobe tools, and a multiple port connection panel for connecting the delivery tubing for the coolant, vacuum, and electrical wiring individually to each of the one or more cryoprobe tools. The manifold may also include an entry port for insertion of a supply pipe connected to the liquid nitrogen supply, vacuum pump and electrical wiring, which may all be stored in a mobile cart. The height of the upper ledge on which the temperature display and control panel and multiple port connection panel may be mounted will be selected to provide easy viewing of and access to the temperature display and temperature controls and probe delivery tubing connection ports.

The manifold unit may also be formed with two main sections, a wheeled vertical support and refrigeration unit storage column, and a foldable control console arm, the latter extending outwardly, e.g. at right angle, from the support column and over the patient for ease of unhindered access to the probes, during use, while being folded flat and parallel to the support column, during storage.

The sub-cooling refrigeration system may be located in the base of the manifold column. Here the $LN_2$'s temperature is reduced some 10°–14° C. below its boiling point. Before entry to the refrigeration system, the $LN_2$ supply line may be split into separate supply lines, one per probe, through independently operated valves, which may be motor operated, or manual, but preferably solenoid valves. These valves not only determine which probes receive $LN_2$, but also control each probe's temperature by controlling the amount and/or rate of supply of $LN_2$ to each probe. The valves may, for example, be of the on-off type for providing intermittent flow, or of the variable or proportional type for controlled rate of flow. Each of the independent supply lines may pass through separate heat exchanger coils within the refrigeration system and then to the probe. In a preferred embodiment described below, the working fluid of the refrigeration unit is also $LN_2$, and another (solenoid) valve may be provided to maintain the refrigeration system's refrigerant level. The valves should be located on the supply side of the heat exchangers to prevent adding heat to sub-cooled $LN_2$.

Sub-cooling of the liquid cryogen, preferably $LN_2$, can be accomplished by any of the refrigeration techniques known in the art. Various high performance refrigeration cycles and thermoelectric refrigeration devices are known and available. Refrigeration with liquid helium can also be used to sub-cool $LN_2$. However, in a preferred embodiment of the invention sub-cooling of the $LN_2$ in the sub-cooling refrigeration system is accomplished by direct or indirect evaporative cooling which relies on the thermodynamic principle that the boiling point of a liquid of a pure substance in equilibrium with its gaseous phase is a function of pressure. Therefore, as the pressure exerted on liquid nitrogen is lowered, its boiling point decreases resulting in evaporative cooling of the liquid nitrogen. That is, the energy required for the liquid nitrogen to evaporate is supplied by the liquid nitrogen, therefore, resulting in a lowering of the liquid's temperature. For example, for $LN_2$, at a pressure of about 1.8 pounds per square inch absolute (psia), it will have a temperature of about −210° C. In the receptacle of the vacuum chamber of the refrigeration system, a large volume of $LN_2$ is subjected to a partial vacuum of from about 1.8 psia up to about 14 psia, preferably from about 1.82 to about 3 psia, such that the temperature of the $LN_2$ sub-cooled refrigerant is lowered to a temperature below its normal boiling point, for example at or near the triple point at which temperature liquid and solid nitrogen are in equilibrium and form a thickened mixture referred to as "nitrogen slush" in which liquid and solid nitrogen coexist. The nitrogen slush or sub-cooled liquid nitrogen will be referred to as $SN_2$. In direct evaporative cooling $LN_2$ flows through heat exchanger coils suspended in the $SN_2$, the $SN_2$ extracts heat from the $LN_2$. The resulting sub-cooled $LN_2$ cryogenic refrigerant (probe $LN_2$) then continues to flow to the cryosurgical probe tip to cool the closed end of the probe tip.

In direct evaporative cooling, the evaporatively cooled $SN_2$ is used directly as the probe $LN_2$. A commercially available liquid cryogen pump can be used to directly pump the $SN_2$ from the vacuum chamber to the cryosurgical instrument(s). In another mode of direct evaporative cooling, high pressure nitrogen gas can be used as the driving force for pumping the $SN_2$ from the vacuum chamber to the cryosurgical instrument(s). It is not necessary to lower the temperature of the sub-cooled refrigerant to the triple point of nitrogen. In fact, it is generally preferred to maintain the refrigerant temperature at just above the triple point, which for nitrogen is very near to the solidification temperature, to avoid solidification of the $SN_2$ refrigerant and to avoid solidification of or nitrogen crystal formation in the probe $LN_2$ flowing through the heat exchanger coils, during indirect evaporative cooling, such as might occur, for example, during periods when the probe $LN_2$ flow rate is low, and the refrigerant temperature is at the nitrogen triple point or solidification temperature. Therefore, in practice, it is preferred to maintain a vacuum on the liquid nitrogen refrigerant which is slightly above about 1.81 psia, such as 1.83 psia or higher.

In the indirect evaporative refrigeration system using heat exchanger coils within $SN_2$ any residual nitrogen gas $N_2(g)$ which may be present in the $LN_2$ working fluid (refrigeration $LN_2$) for the refrigeration system may be condensed to $LN_2$ before it enters the vacuum chamber, for example, the refrigeration $LN_2$ may be passed through another (pre-cooling) heat exchanger also arranged within the $SN_2$ in the same receptacle of the vacuum chamber.

In practice, evaporative cooling can deliver to the probe freezing zone $LN_2$ at from 10° to 14° C. below its boiling point, generally around −208° C. By maintaining a sufficiently high flow rate, which will depend on among other factors, the delivery pressure, length of tubing and radius, the $LN_2$ will flow through the probe without being warmed to its boiling point inside the probe. The result is that $LN_2$ enters the probe and, after cooling, $LN_2$ exits from the probe. By keeping the nitrogen refrigerant in its liquid phase, a very high flow rate (relative to conventional probes operating by boiling of $LN_2$ and consequent expansion of the coolant) may be obtained. Because the thermal conductivity of $LN_2$ is much higher than $N_2(g)$, the overall cooling efficiency is greatly improved, with the amount of cooling in the freezing zone being determined by the temperature gain of the $LN_2$ from entrance to exit of the probe, the specific heat of $LN_2$, and the flow rate. The $LN_2$ exiting the sub-cooling refrigeration unit at −208° C. can be delivered to the freezing zone at the closed end of the probe tip, at say −206° C. At this temperature, the sub-cooled $LN_2$ can cool in the probe by 10° C. and still remain liquid. The amount of energy it can extract by cooling with 10° C. is given by the expression m·c·10° C., where c is the heat capacity of liquid nitrogen and m is the mass flow rate of the liquid nitrogen. However, since generally by increasing the flow rate, m, it is possible to design the system in such a way that the amount of heat extraction required for freezing will result in a heat gain of less than 10° C., at least a portion of the delivered sub-cooled $LN_2$ can be recovered, after exiting from the cryoprobe in the $LN_2$ retrieval Dewar provided for that purpose. The capability of recovering $LN_2$ is another advantage of the present invention.

Another important advantage of the very low probe tip temperatures made possible by the use of sub-cooled $LN_2$ as the probe cryogenic refrigerant is the ability to substantially reduce the diameter of the probe tip while maintaining high freezing capacity. For example, according to the present invention, probe tip (outer shell) diameters as small as about 1.5 millimeters or 2 millimeters can be used effectively for freezing much larger areas than for conventional cryoprobes of the same size. Such small probe diameters will expand the areas of application of cryosurgery of tumors or other undesirable tissues, such as prostate tumors and other small tumors or diseased tissues and organs deep in the body.

As noted above, the sub-cooling refrigeration system may be located within the mobile manifold unit so that it may be placed as close to the patient as possible. However, in view of the high efficiency in cooling the sub-cooling refrigeration system may also be physically located within the mobile cart together with the vacuum pump, $LN_2$ dewars and other components. Of course, it is also understood that the sub-cooling refrigeration system, whether the preferred evaporative cooling described above, or other form of refrigeration, may be simply provided as a self-contained unit with its own housing. Furthermore, while the sub-cooling refrigeration system may be most advantageously used with the cryoprobe instruments according to this invention, it may also be used with advantage in other cryoprobe instruments which use a liquid cryogenic refrigerant for cooling the probe tip. The sub-cooling refrigeration system may also be used for cryoprobe tools of the spray type.

The mobile manifold unit may, and preferably will, include a control panel with associated control electronics. The control panel may conveniently be located on the upper ledge or foldable control console arm which may be hingedly connected to the upper end of the support column. In the embodiment wherein the manifold unit includes a separate support column and foldable control console arm, the height of the support column may ideally be selected so that when the control console arm is in its extended position, the underside of the console arm will provide at least several inches, for instance from about 8 to 20 inches, clearance, from the surface of the operating table so that it may easily fit over the patient. Conversely, the top surface of the console arm or upper ledge of the single support column will be at a height such that any probe displays can be easily viewed by the surgeon and any controls on the top or side surfaces of column or the console arm will be easily accessible to the surgeon.

Control functions which may be supported by the manifold unit include, for example, (i) probe off; (ii) probe cool or freeze mode; (iii) probe heat (or thaw) mode; (iv) probe stick mode; and (v) temperature set point. The probe mode controls may conveniently be implemented as push-buttons, which may be lighted, while the temperature set point control may be an analog or digital knob or thumbswitch or push operated digital switch. Three probe mode control pushbuttons may be used for the four described functions, in which case, the "OFF" mode will be the normal position when none of the three push-buttons are activated. The "stick" mode may be used to achieve a moderately low temperature, e.g. −30° C., sufficient to freeze the tissue in contact with the freezing zone of the probe tip, to cause the tip to stick to the tissue. The "stick" mode is especially convenient when the surgeon wishes to place multiple probes in the patient, the probes then being located and stuck in position one at a time. The sticking temperature may be preset independently of the temperature set point.

The manifold unit will also preferably include individual temperature displays for each probe controlled thereby. All of the controls may be located on the ledge or control console arm, while all of the associated electronics and wiring may be located within the single column or within the console arm or within both the console arm and support column. Furthermore, each set of controls may be located next to the probe delivery line connection port served by that set, thereby reducing any potential confusion over which probe is controlled by each switch and which probe temperature is being displayed by each individual temperature display. In addition, appropriate color coding may be associated with each probe delivery line connection port and/or each set of controls and with the associated probe refrigerant delivery tubing and/or the probe itself to further assist in associating each probe and its operating controls, displays, connecting hoses, etc.

Also included on the manifold's ledge or console control arm are the connection ports for one or more, usually 2 or more, preferably 4 or more, e.g. from 5 to 10, refrigerant and vacuum delivery lines for independently operated and controlled cryosurgical probes. The delivery line connection ports serve to connect the supply and return $LN_2$ cryogenic refrigerant lines, and preferably an insulating vacuum line, and also the electrical connection for a thermocouple or other temperature sensing device located in the probe tip for measuring and controlling probe tip temperatures.

In the present invention, the thermocouple may preferably be attached to the movable seal member at a point that is in contact with the inner wall of the probe shell. By placing the thermocouple out of direct contact with $LN_2$ more realistic temperature readings can be expected.

The cryogenic surgical system of the invention may also include a mobile storage and supply cart which may also function as a main console unit for storing and transporting the various components of the system, including, for example, the mobile manifold unit, $LN_2$ storage vessel(s), e.g. Dewar(s), vacuum pump, and a redundant control panel, as well as various connecting hoses and cables, cryosurgical probes and the like. In a highly preferred embodiment, the mobile cart may also include a data logging and display computer with monitor and keyboard.

The mobile cart may include one, two or more storage vessels, e.g. Dewars, for the liquid nitrogen to be used as the cryogenic liquid refrigerant for the cryosurgical probes and also for use as the $LN_2$ refrigerant for the indirect evaporative sub-cooling refrigeration system. In one preferred construction, the mobile cart contains two storage dewars, each capable of holding, for example, about 10 to 25 liters or more, for example, 10, 25, 30, 40 or 50 liters of $LN_2$. The size of the storage dewars will be selected to hold sufficient $LN_2$ for the particular surgical procedure (e.g. type of tumor or tissue). However, because of the very high efficiencies of the cryosurgical system of this invention, it is expected that significant reductions in $LN_2$ requirements can be achieved. This is still another advantage of the present invention.

The $LN_2$ storage dewars may be connected through a series of electric solenoid or other types of valves in a manner to allow one dewar to act as an $LN_2$ retrieval vessel for collecting any $LN_2$ recovered from the cryosurgical probes during a surgical procedure. The $LN_2$ retrieval vessel may be vented to atmosphere or small positive pressure while the other (supply) dewar will be under positive pressure from a suitable external source, preferably $N_2(g)$. During a surgical procedure, if the supply dewar is depleted of its $LN_2$, or if the $LN_2$ level falls below a predetermined level, the electric solenoid valves may be manually or automatically activated to reverse the input and output lines so that the retrieval dewar will be switched over to become the supply dewar and vice versa. Maintaining the retrieval dewar at atmospheric or small positive pressure allows the system to be easily refilled from a large $LN_2$ supply tank without interrupting the surgical procedure. Each dewar may be equipped with a level or other indicator which may operate a notification light or other signal whenever the $LN_2$ level in the vessel falls below a certain predetermined value, for example, below one-third of capacity.

The dewars may also be equipped with pressure relief valves as an additional safety precaution. During routine storage of the system when not in use (e.g. in the "power off" mode) all of the valves to and from the dewars will normally be closed to maintain the dewars under a positive pressure (due to evaporating $LN_2$). This will avoid having any water vapor or atmospheric air from entering the system and freezing during subsequent use. Also, by not having the tanks vented to the atmosphere the $LN_2$ in the tanks will be saved for future use.

Still further, according to this invention, by virtue of the sub-cooling of the liquid refrigerant, it is now possible to effectively and economically recover $LN_2$ from the probe tip and reuse the recovered $LN_2$. For example, $LN_2$ exiting from the probe tip can be routed through appropriate tubing, preferably vacuum insulated, to the retrieval dewar for subsequent use. If only a single dewar is used for the $LN_2$ storage, the return $LN_2$ may first be passed through a compressor or other pressurizing system to raise the $LN_2$ pressure to above the pressure in the dewar. The compressed or pressurized return $LN_2$ may then be recovered in the supply dewar. The availability of a simple and inexpensive means for recovering cryogenic refrigerant in a closed cycle system is still another advantage of the cryogenic system of this invention.

Another system component which may be housed within the mobile cart is a high-capacity vacuum pump. The vacuum pump system can provide the vacuum for insulating the $LN_2$ supply and delivery lines and the cryosurgical probes and also for operating the $LN_2$ evaporative sub-cooling refrigeration system. The vacuum pump may be fitted with a high efficiency exhaust filter to remove oil particles down to submicron size. The filter may also provide some noise reduction by acting as a muffler. Further noise reduction can be provided by mounting the vacuum pump on suitable vibration isolation or vibration absorbing mounts. The effluent from the vacuum pump, which is essentially dry nitrogen, may be vented into the dewar compartment to reduce the amount of condensation tending to collect on the $LN_2$ supply plumbing.

Instead of, or in addition to a vacuum pump for continuously withdrawing gas from the supply and delivery tubing and from the cryoprobe, other known gas evacuation systems can be used. For example, by providing one or more small openings in the wall (tubing) separating the internal (i.e. in the cryoprobe) and/or external refrigerant return lines and a surrounding vacuum line, the rapidly flowing refrigerant fluid can cause the gas in the vacuum line to aspirate through the opening(s). Of course, other arrangement for maintaining an active vacuum in the cryoprobe as well as in the external supply and delivery lines may also be provided.

In still another section of the mobile cart a second control panel containing essentially the same controls as described for the mobile manifold unit may be provided. Thus, the system according to the invention may include this second or redundant control panel so that the control and operation of the cryosurgical probes may take place at either the manifold (e.g. under the direct control of the lead surgeon) or at the mobile cart (e.g. under the control of a physician, nurse, technician or other surgical team assistant).

It is understood, however, that in the embodiment described below, wherein a separate manifold unit is not provided, the control panel on the mobile cart may be the only set of controls.

Thus, it is also within the scope of the invention to bypass or entirely eliminate the mobile manifold unit in which case the sub-cooling refrigeration system may also be stored in the mobile cart. Here too, the great efficiencies in operation resulting from the sub-cooled operating temperature of the $LN_2$ refrigerant, especially when the $LN_2$ delivery tubing from the refrigeration system to the cryosurgical probe is at least partially vacuum insulated, allows the external $LN_2$ delivery tubing to extend greater distances than for conventional systems, for example up to 10 feet, especially up to 8 feet, while still delivering $LN_2$, via the probe's internal $LN_2$ supply tube, to the freeze zone of the cryoprobe at temperatures below $-196°$ C. Therefore, using flexible tubing, such as polytetrafluoroethylene (PTFE or Teflon) or other metal or non-metal material capable of withstanding the $LN_2$ temperatures without becoming brittle, the external $LN_2$ delivery and return tubing may be stored in the mobile cart when the system is not in use while during a surgical operation, the external $LN_2$ delivery and return tubing may be extended from the mobile cart at a remote position in the operating room to the site of the operating table. It is also contemplated to provide rigid conduits through which the external $LN_2$ delivery and return tubing, vacuum and electrical connections are conveyed to near the site of the operating table. This rigid tubing may be supplied, for example, as a number of telescoping sections which may be extended from the mobile cart or as a number of connectable segments.

For example, a rigid hollow substantially horizontally disposed arm of one or more segments, of from about 1 to 6 feet in length, in total, may be pivotably connected to the mobile cart. At the open end of the pivotal arm, remote from the cart, a multiplicity of probe delivery tube connection ports may be provided, each port being connected through suitable tubing to the cryogenic refrigerant, for example, the outlet of a heat exchanger coil in the sub-cooling refrigeration system's vacuum chamber located in the art. Each port may likewise be connected to a refrigerant collection or recovery vessel, for example, the retrieval dewar of a dual dewar arrangement, as well as to the gas withdrawal means, for example, a vacuum pump, also present within the cart. A separate digital temperature display console, for each available cryoprobe instrument, in addition to the graphic display on the computer monitor, may also be provided in close proximity to the entry port of the pivotal arm to the cart. In this manner, a compact system requiring a minimum effort for connecting a multiplicity of cryoprobes and flexible delivery tubes to the cryogenic refrigerant supply and return lines and the gas withdrawal means for creating and maintaining an active vacuum thermal insulation in the cryoprobe (s) as well as in the connecting pipes and tubing is provided.

The control functions provided on the mobile cart control panel may be the same as those previously described for the manifold, namely (i) probe off; (ii) probe cool mode; (iii) probe heat mode; (iv) probe stick; and (v) temperature set point. Here too, pushbuttons (which may be lighted) may conveniently be used for the probe mode controls (i), (ii), (iii) and (v), while a digital thumbswitch, etc., may be used for the temperature set point. Each individual probe will have associated therewith its own set of probe mode controls and temperature set point control. Preferably, a selector switch located on the mobile cart control panel will enable the probe control to be switched between the control panels on the mobile cart and the control panel on the manifold. Furthermore, a light (e.g. LED device, light bulb, etc.) controlled by the selector switch, may be provided on both the mobile cart control console and the manifold control console arm to signify which unit has control.

As a counterpart to the individual probe temperature displays located on the manifold, the mobile cart assembly may conveniently include a data collection computer and monitor to provide a real time display of each probe's temperature and also a time versus temperature graph. Each probe's temperature reading may be displayed in a unique color with the corresponding graph trace in the same color. Also, each probe's displayed information may be stored on a floppy disc or magnetic tape to provide an historical data log of the entire procedure for later analysis, as and if, required.

Accordingly, from the foregoing description, it may be appreciated that the present invention provides a cryosurgical system wherein a multiplicity of cryosurgical instruments may simultaneously be used to freeze a single or multiple tumors or organ(s). Furthermore, the temperature of each probe may be individually controlled as determined by the physician to be most efficient for the complete cryogenic destruction of the tumor or other diseased organ. The temperature of each probe tip may be individually determined and monitored by either digital or analog display. Furthermore, means, such as color coding of the displayed temperature and the probe, or probe tubing, will allow the physician to easily determine which of the multiple probe tips is at which displayed temperature. Redundant displays and controls may be provided to allow either the chief operating physician or an assistant to control the mode and temperature set point for each of the cryoprobe instruments. Accordingly, highly efficient cryosurgical operations may be carried out. These efficiencies are further increased when sub-cooled $LN_2$ according to the invention is used as the cryogenic refrigerant and also when the adjustable freeze zone cryoprobe tools according to the invention are used together with the multiprobe system.

Any type of commercially available tubing may be used to connect the $LN_2$ supply tank (e.g. dewar) and vacuum pump to the sub-cooling refrigeration system (which may be referred to, for convenience, as external ($LN_2$/vacuum) supply tube) and to connect the sub-cooling refrigeration system to the individual cryoprobes (which may be referred to as external ($LN_2$/vacuum) delivery tube(s)).

However, in accordance with a preferred embodiment of the invention, the external supply tube includes an outermost pipe, an inner pipe and within the inner pipe the $LN_2$ supply pipe (from the $LN_2$ supply dewar) and the $LN_2$ return pipe (from the cryoprobe to the $LN_2$ return dewar). All of the pipes may preferably be fabricated from stainless steel. The inner pipe provides a return line for cold $N_2(g)$ generated in the vacuum chamber of the sub-cooling refrigeration system. The cold $N_2(g)$ exiting from the inner tube of the external supply tube may be vented to atmosphere, preferably in the mobile cart, especially to the vacuum pump in the mobile cart where the cold $N_2(g)$ may be warmed before discharging it to the atmosphere. However, while flowing in the inner tube the cold $N_2(g)$ surrounds the $LN_2$ supply and return pipes and provides effective thermal insulation for the sub-cooled $LN_2$ and return $LN_2$ or $N_2(g)$ flowing through the $LN_2$ supply pipe and $LN_2$ return pipe, respectively. Furthermore, by connecting the annular space between the outermost pipe and the inner pipe to the vacuum pump, an active vacuum will be formed and maintained in the annular space to provide still additional thermal insulation.

The external supply tube may be provided as a single pipe, but preferably as multiple connectable pipes of different lengths, e.g. 12 inches, 24 inches, 36 inches and 48 inches, with appropriate male and/or female connections at the ends of each pipe for connection to each other as well as to the vacuum pump and $LN_2$ supply and return dewars at the inlet end thereof and to the sub-cooling refrigeration system and probe vacuum line at the outlet end thereof. It is also contemplated that the supply pipe sections may include vertical pipe sections connected to each of the mobile cart and mobile manifold with the appropriate lengths of overhead supply pipe sections connecting the vertical pipes through suitable elbow joints at a suitable height to permit free passageway in the operating room. Also, to assure a fluid tight seal between the supply pipe sections, the pipe ends may be provided with Teflon spacers which fit over the stainless steel pipe and, due to the differential thermal shrinkage between Teflon and stainless steel will form a fluid tight compression fit. Also, O-rings and clamps may be used to join together the supply pipe sections. Inside each supply pipe, first spacer discs may be provided to keep the inner tube separated from the outermost tube, while second spacer discs may be provided to keep the $LN_2$ supply and return pipes separated from each other, as well as from the inner tube.

It is also preferred that the connection ports for connecting the supply pipe to the mobile cart and mobile manifold be capable of relative angular (rotation) movement to permit the best possible orientation of the manifold and cart in any particular operating room configuration.

Each individual cryoprobe will be provided with its own delivery tube. Each delivery tube will be formed of flexible tubing (e.g. Teflon) including an external $LN_2$ delivery line for connecting the source of liquid cryogenic refrigerant (e.g. the outlet of one heat exchanger coil from the sub-cooling refrigeration system) to the probe's internal $LN_2$ supply tube, an external return line providing a passageway for the refrigerant exiting from the probe's internal refrigerant return or exhaust tube, and a vacuum hose connecting the vacuum port to the probe with the vacuum pump. Preferably, each of the refrigerant delivery and return lines may be formed of relatively small diameter flexible Teflon tubing while the vacuum hose is formed of larger diameter flexible Teflon tubing surrounding both the delivery and return tubing such that the vacuum drawn in the vacuum tubing provides thermal insulation for the refrigerant tubing. The vacuum tubing may be corrugated or pleated to provide additional flexibility. Since Teflon tubing is normally transparent the vacuum tubing may be provided with a metallized coating, e.g. by chemical vapor deposition, or may be laminated or covered, preferably on the inside surface, with a metallized, e.g. aluminum, gold, platinum, etc., thin plastic foil, e.g. metallized Mylar film, which is commercially available, for IR radiation reflection. Spacer elements may be provided within the vacuum tube to separate the $LN_2$ supply tube from the return tube, as well as separating the internal tubes from the vacuum tube.

Another major subsystem of the cryogenic surgical system of the invention is the cryosurgical instrument or cryoprobe itself. The cryoprobe may be considered to include two major components: (a) a probe tip and (b) an instrument body or probe handle/connector assembly. The probe tip may be provided in several different lengths and diameters and will include an outer hollow shell or casing, preferably of stainless steel or copper, with a narrow, but usually blunt, closed tip end and an open end, and, fitting within the shell an internal $LN_2$ delivery tube, a refrigerant return (or exhaust) tube, and a seal member for separating the freezing zone at the closed end from the insulated region at the open end. As in conventional probe tips, the internal $LN_2$ delivery tube and refrigerant return ($LN_2$ or $N_2(g)$) tube are usually arranged in parallel and most preferably are in the form of concentric tubes having the same longitudinal axis as the hollow shell, such that the hollow shell, $LN_2$ delivery tube and refrigerant return tube form three concentric tubes. The $LN_2$ delivery tube may be the innermost tube and the annular space between the delivery tube and return tube forming the passageway for removing the refrigerant from the freezing zone at the closed probe tip end to the external $LN_2$ return tube.

According to the present invention, the seal member is fixed to the refrigerant return tube near the inlet end thereof. The seal member is dimensioned to fit slidingly within the outer hollow shell, the space between the seal member and the closed tip end constituting the freeze zone and the space behind the seal member and insulated region. By adjusting the distance of penetration of the combined return tube and seal member into the hollow shell the length, L, of the freeze zone at the closed probe tip end can be adjusted according to the dimensions of the tumor (size, mass, etc.) or tissue to be cryogenically destroyed. As noted above, the $LN_2$ supply and exhaust tubes will generally be provided as concentric tubes, the supply tube being the inner tube and defining an $LN_2$ probe refrigerant supply passageway, while the space between the tubes defines an annular refrigerant exhaust passageway. However, a single double lumen tube wherein a common wall divides a tube into first and second flow passageways for the $LN_2$ supply and refrigerant exhaust, respectively, may also be used. Alternatively, separate tubes arranged in parallel, of the same or different lengths (preferably the $LN_2$ supply tube will be longer) may also be used to provide the flow passageways for the $LN_2$ supply tube and refrigerant return or exhaust tube.

According to another feature of the invention, the cryosurgical probe instrument may be provided with a movable seal member for preventing fluid flow from the closed end of the probe tip to the open end of the probe tip except through the refrigerant exhaust passageway which extends through the seal member. The movable seal member thus provides a simple means for adjusting the freeze zone length at the closed end of the probe tip to accommodate different sizes of tumors to be destroyed by freezing. This allows the surgeon to take advantage of the possibility of viewing a tumor deep in the body by magnetic resonance imaging, ultrasound, or other imaging technique, prior to the beginning of the cryosurgery. For example, by providing a series of cryoprobes with just two interchangeable probe tips of different lengths, one accommodating, for example, movement of the position of the seal member to provide a freeze zone length of from 10 to 50 millimeters, and the other accommodating, for example, movement of the seal member to provide a freeze zone length in the range of from 50 to 100 millimeters, the two interchangeable probe tips can provide a range of freeze zone lengths of from 10 to 100 mm (approx. 0.4 to 4 inches). Of course, smaller or larger sizes can also be provided. Thus, if the imaging of the tumor shows a mass having one major dimension of, say, 75 mm, and a second major dimension of 30 mm, the physician may preselect a first probe tip and adjust the freezing zone length to about 70 mm, and a second probe tip with freezing zone length adjusted to about 26 mm. Of course, dependent on the volume of the mass, only one or several, e.g. up to 5 or more, cryoprobes may be needed, each of which may include a probe tip with movable seal preadjusted to accommodate a specific dimension of the mass. In this way, the physician can optimize the probability of fully destroying the tumorous or diseased tissue mass while minimizing destruction of healthy surrounding tissue. Furthermore, by monitoring the cryosurgery with an available imaging technique, the physician may observe, in real time, the actual extent of freezing, and, if necessary, can make adjustments to the freezing zone lengths of one or more of the cryoprobes.

The availability of the movable seal with the above described advantages in terms of the cryosurgical procedure also has the additional important and practical advantage of substantially lowering the cost of manufacture of the cryoprobe. For example, unlike conventional cryoprobes which require perfect seals, with the attendant costs of precision machining, soldering, and welding, the movable seal, especially when used in combination with active vacuum thermal insulation in the probe tip, need not necessarily, although it generally will, form a perfect seal. That is, if the seal member does not form a perfect seal with the probe shell or casing or with the flow passageway tubes extending therethrough, any small leakage of refrigerant from the freezing zone into the insulated region will not destroy the active vacuum insulation, since the refrigerant will be continuously withdrawn by the means for continuously withdrawing gas.

Moreover, the cryoprobe instrument of this invention with the movable seal can be manufactured at sufficiently low comparative cost that the probe tip may, and usually should, be disposed of after each use, regardless of whether there is still a perfect seal between the seal member and probe shell or refrigerant flow tubes. Also, for some embodiments of the seal member, e.g. plastically deformable materials and those requiring crimping, only a single use of the probe tip may be possible. However, even for the elastically deformable seal members, in view of the substantial temperature cycles to which the seal member will be subjected, it is recommended that the probe tip with seal member, be discarded after a single use.

The seal member, according to one embodiment of the invention, may be formed from an elastically compressible solid, e.g. rubber or elastomeric, or spring-like metal or plastically deformable material, e.g. resinous plastic materials, especially thermoplastic resin, such as Teflon, graphite, and soft metals, such as lead. The material used for the sealing member should be one having an embrittlement temperature which is capable of withstanding the cryogenic temperatures of the refrigerant medium without shattering, preferably, no more than about −10° C., especially no more than about −30° C., for example, no more than about −40° C., for example, about −50° C. or −60° C., or less. The elastically compressible sealing material may be shaped as a substantially cylindrical mass of material such that at room temperature its diameter (in the uncompressed state) is greater than the inside diameter of the hollow probe shell. In practice, it has been found convenient to form the elastomeric sealing material as a substantially cylindrical mass of an elastomer with about the same outside diameter as the outside diameter of the hollow probe shell. Therefore, the sealing member will be compressed by the probe shell an amount corresponding to the wall thickness of the probe shell to form an effective fluid tight but repositionable seal. The space in front of the seal will constitute the freezing zone while the space behind the seal will be thermally insulated to prevent the probe shell from reaching the subfreezing temperatures of the freezing zone. The cylindrical mass will also include an aperture through which the exhaust tube (as the outer tube of concentric tubes or the double lumen tube), or apertures for both the refrigerant exhaust tube and LN2 supply tube (if separate tubes are used) will be fitted. The diameter of the aperture or apertures will preferably be somewhat smaller than the outer diameter of the tube or tubes to be fitted therethrough to provide a fluid tight seal between the periphery of the tube(s) and the elastomeric seal material. Also, it is preferred to provide means on the return tube or double lumen tube over which the seal member is fitted to prevent the seal member from sliding movement relative to the return tube or double lumen tube once it has been fitted on the tube. For example, a thin metal wire, e.g. copper, may be brazed or soldered to the outer surface of the tube at the desired location for the seal member, for example, from about 0.1 to 0.5 or 1.0 inch (2.5 or 12.7 of 25.4 mm) from the inlet end of the exhaust tube, to provide a minimum freeze zone length of, for example, from about 0.25 to 2.0 inches (about 6 to 50 mm) from the closed tip end of the probe shell. The seal member will be fitted over the stop member and will be held securely in place. Instead of the brazed metal wire, the return tube may be provided with one or more projections or bumps to hold the seal member in place. Generally, it is envisioned that the probe tips may be provided in two or more different lengths, for each diameter, each size offering a different range of freezing zone lengths. For example, one set of probe tips may offer freezing zone lengths which may be varied over a range of from 5 to 50 mm, a second set being adjustable to from 30 to 70 mm, a third set providing controlled variation in the range of from 50 to 100 mm, and so on.

Since the diameter of the cylindrical mass of elastomeric material is greater than the inside diameter of the hollow probe shell, it will be tightly packed (compressed) to a reduced volume when the return tube and attached vacuum seal member is inserted into the probe shell to assure a fluid tight vacuum seal separating the freeze zone at the closed end of the probe tip from the remainder (i.e. downstream or proximal end) of the probe tip which provides a thermally insulated region. Furthermore, when the seal member is exposed to cryogenic temperatures during use of the probe any shrinkage of the rubbery or elastomeric material due to contraction will be offset by the extra volume of the compressed mass of material which will expand to maintain a fluid tight seal.

When the seal member is formed from a plastically deformable material, such as Teflon, graphite, lead, and so on, it may be shaped as a substantially cylindrical mass having the same or slightly larger (e.g. 0.01 to 1% larger) diameter than the inside diameter of the hollow probe shell. In this case, the seal member may be forcibly pushed or pulled from its initial factory setting (assuming that the probe tip components are preassembled and sterilized in the factory for minimum handling) to its desired position, as determined by the size and shape of the tumor.

The seal member may also be formed from a thin spring like metal construction, for example, a bowl shaped spring metal having an aperture through which the refrigerant flow passageway tube or tubes may be fluid tightly fitted. If necessary, the periphery of flow tube(s) may be soldered to the spring metal to fluid tightly seal the aperture(s), however, since this soldering can be done outside the probe shell, it would not entail any significant expense. Furthermore, even if there are any pinhole leaks, the active vacuum in the thermally insulated region will still prevent the probe shell from freezing in the insulated region.

In an alternative embodiment of the invention, and one which is especially suitable for probe tips having hollow probe shells with diameters of below about 6 mm (about 0.24 inch), especially below about 5 mm (about 0.2 inch), for example from about 1 to about 3 or 4 mm, such as 1.5 mm or 2 mm, the seal member may be formed of a rigid, e.g. solid metal, disc. The exhaust tube is fitted through an aperture or perforation centrally located in the disc and the disc and tube are welded, soldered or otherwise fluid tightly adhered to each other with the disc being fixed at the desired location near the inlet end of the exhaust tube. The rigid disc will have a diameter which is slightly less than the inside diameter of the hollow probe shell, for example, about 0.0001 to 0.01 inch (0.0025 to 0.25 mm), preferably 0.0005 to 0.008 inch less than the inside diameter of the shell.

After the return tube and affixed seal member (disc) is inserted the predetermined distance into the hollow probe shell the shell will be crimped using a crimping tool at the location of the disc to thereby form a fluid tight seal between the periphery of the disc and the crimped shell. Because the probe shell has a very thin wall, on the order of from about 0.001 to 0.01 inch, it may be easily crimped to provide the desired fluid tight vacuum seal. The crimping tool may be designed with mating arms which provide a circular crimp with the same outside diameter as the rigid disc.

Especially in this embodiment, the probe tip will normally be discarded after a single use.

In still another embodiment, the seal member may be shaped in the form of a disc with a slightly smaller diameter than the inner diameter of the hollow probe shell, the disc being formed from a substantially rigid material having a coefficient of expansion which is different than the coefficient of expansion of the probe shell. For example, the probe shell and disc may be formed of different grades of stainless steel, or two different metals, e.g. stainless steel and copper, or from a metal and non-metal, e.g. stainless steel probe shell and Teflon disc. The disc will have at least one aperture in a central portion thereof through which the exhaust tube or exhaust and supply tubes extend and form a vacuum tight seal. At room temperature, the $LN_2$ supply/return vacuum unit will be slidable within the shell, but at low cryogenic operating temperatures encountered during use, the disc and probe shell contract differentially to thereby form a fluid tight seal between the periphery of the disc and the shell.

The instrument body to which the probe tip will be connected provides means for connecting the refrigerant supply and exhaust tubes, gas evacuation tube and electric wiring in the probe tip to the delivery tube, including the $LN_2$ external supply and refrigerant exhaust tubes and vacuum tube and electric wiring. Thus, the instrument body will include a series of flow passageways through which the cryogenic refrigerant is transferred from the $LN_2$ supply source (e.g. the sub-cooling refrigeration system described above) to the probe tip and through which the spent refrigerant liquid or gas is exhausted from the probe tip to either the atmosphere or to a recovery vessel. Another flow passageway may be provided for continuously withdrawing gas to form an active vacuum in the probe tip (region behind the seal) and, preferably also in the instrument body to provide thermal insulation for the cryogenic refrigerant. Still other passageways may be provided for electrical wiring for a thermocouple or other temperature sensing device or for optional electric heating elements in the probe tip. The instrument body may also function as a handle for manipulating the probe tip. For example, the probe instrument body may include a first inlet for receiving a cryogenic liquid refrigerant, a first outlet for removing the refrigerant, a second outlet for withdrawing gas from the instrument body, a vacuum chamber in communication with the second outlet, means for receiving the open end of a closed end cryosurgical probe tip, a channel connecting the vacuum chamber and the receiving means, a first flow passageway for transporting the cryogenic liquid refrigerant from the first inlet through the vacuum chamber to the vicinity of the closed end of the probe tip, and a second flow passageway for transporting refrigerant from the vicinity of the closed end of the probe tip through the vacuum chamber and back to the first outlet.

The instrument body may be formed as a single piece or as two or more mating parts to be joined together. Furthermore, when the instrument body is formed from two or more mating arts one or more of the parts may be provided as a component of the delivery tube and the remaining part of parts as a component of the cryosurgical instrument. For example, in accordance with a preferred embodiment of the invention, the instrument body may include a probe connector and a delivery tube connector. The probe connector may include at one end thereof means for fluid tightly receiving the probe tip (e.g. a female threaded portion which engages with the male threads of the probe base) and at the opposite end means for fluid tightly receiving one end of the delivery tube connector. The opposite end of the delivery tube connector includes means for receiving the external $LN_2$ supply and return tubes, vacuum tube and electrical wiring from the flexible delivery tube. Thus, in this embodiment, the first inlet for receiving refrigerant, first outlet for removing refrigerant, and second outlet for withdrawing gas are located at the end of the delivery tube connector which is connected to the delivery tube. Complementary hollow portions on the mutually mating ends of the probe connector and delivery tube connector form a vacuum chamber when the two connector parts are assembled. Solid metal electrical contacts or male and female electrical connectors may also be provided on each of the mutually mating ends of the two connector parts such that when the parts are assembled the metal electrical contacts or male and female connectors are in electrical contact with each other to complete the electrical wiring circuit to the thermocouple in the probe tip.

The probe connector and delivery tube connector may be molded from Teflon or similar self-lubricating, low friction plastic or resin material with relatively low heat transfer coefficient. An internal hollow tube member may be separately provided to define a flow passageway through the vacuum chamber and connected to the $LN_2$ inlet and refrigerant outlet. When the instrument body is connected to the probe tip the probe's internal $LN_2$ supply tube will extend through this passageway with its inlet end in fluid flow communication with the $LN_2$ inlet. The probe's internal refrigerant exhaust tube will extend into the hollow tube passageway such that exhausted refrigerant from the probe tip will flow through the annular space between the LN2 supply tube and hollow tube and will be in fluid flow communication with the refrigerant outlet. The hollow tube may preferably be fabricated from metal, such as stainless steel, and the opposite ends of the hollow tube will be received within cylindrical bores located in axial alignment in the probe connector and delivery tube connector. The cylindrical bores receiving the ends of the hollow tube will have substantially the same diameter as the outside diameter of the hollow tube so that a fluid tight compression fit is formed between the periphery of the tube and the receiving bores.

More specifically, in accordance with this embodiment, first and second outlet openings and an inlet opening, each in the form of cylindrical bores, are located at one end of the delivery tube connector and each bore is in flow communication via one or more flow passageways with a hollow portion at the opposed end thereof.

In one particular form of this embodiment, the inlet opening in the delivery tube connector is located on the longitudinal axis of the instrument body and is in fluid flow communication with the hollow portion via first, second and third cylindrical bore flow passageways, respectively, each commonly aligned with the common longitudinal axis of the delivery tube connector and each of the flow passageways having progressively larger diameters. Preferably, the diameter of the first cylindrical bore flow passageway is substantially the same as the diameter of the internal $LN_2$ supply tube of the probe tip and the diameter of the third cylindrical bore flow passageway having substantially the same diameter as the outside diameter of the hollow tube and adapted to receive an end of the hollow tube with a compression seal fit. At least one additional flow passageway connects the second cylindrical bore flow passageway with the first outlet opening.

The first outlet opening may have a longitudinal axis in the same plane as and parallel to the longitudinal axis of the instrument body.

The probe connector includes the vacuum chamber at one end thereof (the end mating with the delivery tube connector. The vacuum chamber may be in the form of an elongated hollow cylindrical bore aligned with the longitudinal axis of the instrument body and extending from the one end thereof over a substantial portion of the length of thereof. At the opposed second end of the probe connector, receiving means for the open end of the probe tip is provided and may be in the form of female screw threads which define an open portion for receiving mating male screw threads on a probe base member provided at the open end of the probe tip. The hollow vacuum chamber cylindrical bore is in flow communication with the open portion receiving means via first and second commonly aligned cylindrical bore passageways. The diameter of the first bore is substantially the same as the diameter of the third passageway in the delivery tube connector and is adapted to receive the other end of the hollow tube with a compression seal fit. The diameter is also smaller than the diameter of the vacuum chamber. The second cylindrical bore as substantially the same diameter as the outside diameter of the probe's internal refrigerant exhaust tube. A second flow passageway having an axis parallel to the longitudinal axis of the probe connector also extends between the vacuum chamber cylindrical bore and the open portion receiving means. This second flow passageway is a gas evacuation channel.

The delivery tube connector may also include a cylindrical bore having fitted therein electrical connectors, e.g. female connectors, for receiving mating, e.g. male, electrical connectors from the delivery tube, to complete the electrical circuit from electrical conductors leading from the electrical connectors to the thermocouple in the probe tip and to an electrical power supply.

In another form of this embodiment, the inlet opening in the delivery tube connector is connected to the hollow portion via an inlet cylindrical bore passageway having an axis parallel to the longitudinal axis of the instrument body, a connecting cylindrical bore passageway having an axis at an angle to the longitudinal axis, the connecting cylindrical bore terminating in a first cylindrical bore adapted to receive the inlet end of the probe's internal $LN_2$ supply tube. The first cylindrical bore is in fluid flow communication with second and third cylindrical bore flow passageways, respectively, each of the first, second and third cylindrical bores being commonly aligned with the common longitudinal axis of the instrument body, and each of these flow passageways having progressively larger diameters. The diameter of the third flow passageway is adapted to receive an end of the hollow tube with a fluid tight compression seal fit. The second cylindrical bore flow passageway is in communication with the refrigerant outlet opening through at least one additional cylindrical bore flow passageway which may have a longitudinal axis parallel to the longitudinal axis of the instrument body.

The probe connector has a similar construction to the probe connector of the particular form described above. However, the hollow cylindrical bore forming the vacuum chamber includes an intermediate portion of reduced diameter adapted to fluid tightly receive therein a molded Teflon (or similar material) insert in the form of a generally cylindrical ring, the inside diameter of which is larger than the outside diameter of the hollow tube. At least one solid metal electrical contact is provided on the end surface of the insert of the insert facing the delivery tube connector receiving end of the probe connector to cover a substantial portion of the end surface. Similarly, at least one solid metal electrical contact is provided on a substantial portion of the one end surface of the delivery tube connector such that when the mutually mating ends of the delivery tube connector and the probe connector are fully connected to each other, the solid metal electrical contacts will be in electrical contact with each other to complete the electrical wiring circuit (through suitable electrical conduction wiring) to a thermocouple in the probe tip.

Prior to joining the probe connector and the delivery tube connector, the hollow tube of substantially the same diameter as the third flow passageway and which is inserted in the passageway of second diameter in the probe connector and extends through the vacuum chamber and along the longitudinal axis, and beyond the one end of the probe connector. The inside diameter of the hollow tube is larger than the outside diameter of the refrigerant exhaust tube or double lumen tube (or the combined diameters of the exhaust and supply tubes when separate tubes are used) such that these internal refrigerant supply and return probe tubes can extend through the tube when the probe tip is connected to the probe connector.

The probe connector and delivery tube connector may be joined together before or after the probe tip is joined to the probe connector. When joined together, the instrument body parts will have a common longitudinal axis and the free end of the hollow tube will fit within the third cylindrical bore flow passageway of the delivery tube connector.

Furthermore, the length of the $LN_2$ supply tube should be such that when the probe tip is joined to the instrument body, the inlet end of the $LN_2$ supply tube will extend into and form a fluid tight seal between the periphery of the supply tube and the first cylindrical bore flow passageway. The length of the refrigerant exhaust tube will be such that its outlet end will terminate within the flow passageway defined by the hollow tube.

Prior to joining the instrument body and probe tip, the $LN_2$ supply tube and exhaust tube with affixed seal member is inserted into the hollow probe shell to provide a predetermined but adjustable length of the freeze zone to best accommodate the tumor or other tissue to be frozen. The predetermined length may be set at the factory to correspond to either the minimum or maximum available length or some intermediate value, for example, halfway between the minimum and maximum values. If this preset length is not the optimum length for the particular surgery, the surgeon may, prior to inserting the closed end of the probe tip into the tumor, reposition the return tube with affixed seal member to the desired position. While this adjustment may be made manually by pushing or pulling on the exhaust tube with the instrument body disengaged from the probe tip, it is preferred to use a thin grasping tool, with appropriate calibration marks, to reposition the exhaust tube and seal member without need to disassemble the probe connector from the probe tip but prior to joining the delivery tube connector to the probe connector. The grasping tool may, for example, be inserted through the hollow tube until it grasps the return tube with grasping means, e.g. pincers, provided at one end thereof and then used to push or pull the return tube to shorten or increase, respectively, the length of the freeze zone.

For example, the $LN_2$ supply tube and exhaust tube with affixed seal member may first be fully inserted into the hollow probe shell until, for example, the outlet end of the $LN_2$ supply tube contacts the closed probe tip end and the seal member abuts against the tapered portion of the closed end of the hollow shell. The probe connector of the instrument body may then be securely fitted to the threaded probe base with the inlet end of the internal $LN_2$ supply tube extending beyond the previously fitted axially aligned hollow tube and the outlet end of the refrigerant exhaust tube located within the hollow tube. Therefore, the portion of the return tube located with the hollow tube is available to be grasped by the thin grasping tool to enable the return tube with affixed seal member to be withdrawn or inserted the predetermined desired distance to adjust the length of the freezing zone. Furthermore, depending on the type of seal member, the probe shell may be crimped, if necessary, to secure the seal. Thereafter, the probe connector and delivery tube connector will be secured to each other by, for example, mating male and female screw thread portions to form the assembled cryosurgical probe instrument. It should be noted that the components of the cryoprobe instrument may be provided in a protective removable cap or wrapper to maintain each of the components in sterile condition, as well as to protect the parts from damage in handling.

In either case, the assembled cryoprobe instrument will then be connected to the flexible delivery tubes by way of the delivery tube connector. That is, each of the $LN_2$ inlet opening, refrigerant outlet opening and vacuum outlet opening, as well as the electrical connectors in the instrument body will be connected to the corresponding external $LN_2$ probe refrigerant supply tubing, refrigerant exhaust tubing, vacuum pump tubing, and corresponding electrical connector, respectively. Usually, all of these utility lines will be included in a single conduit carrying therein, the multiple tubing from or to their respective sources or destinations in the mobile manifold or directly to the mobile cart with appropriate connection fittings which mate with the respective openings in the probe body.

An example of the operation of a cryosurgical system according to the invention which incorporates all of the previously described subsystems, namely mobile cart, mobile manifold, main supply tubes and flexible delivery tubes, and multiple cryosurgical probes with interchangeable and adjustable probe tips and freeze zone lengths will now be given.

Setup

1. Before the system is operated, it is necessary to connect all supply lines and cables. In addition, the $LN_2$ dewars need to be filled to appropriate levels. As a matter of convenience, it is suggested that the dewars be filled before taking the unit to the operating room.

2. Select a location in the operating room on the basis of keeping the mobile cart from interfering with the procedure while, at the same time, keeping it within reach of its connecting hoses and cables. Since the vacuum pump located in the mobile cart may produce limited noise, the cart should be placed such that this low level noise does not disturb those performing the procedure.

3. Disengage the manifold unit from the manifold storage area on the mobile cart and move it to a convenient location close to the operating table.

4. Connect the vertical main supply tube sections on both the cart and manifold and then connect the appropriate length of main overhead supply tube section(s) through the elbow joints to the vertical supply tube sections.

5. Verify that the main power switch is in the OFF position and connect the system to the power source.

6. Switch the main power switch to the ON position and observe that all PROBE OFF push buttons are illuminated on both the manifold and the cart.

7. Test the "CONTROL" indicator light by switching the Control Selector Switch back and forth between the "MANIFOLD" and "CART" position.

8. Verify that the vacuum pump is running and that the refrigeration system's $LN_2$ fill valve is open and filling is taking place. It may take from 15 to 30 minutes for the system to cool down and be ready for use.

Procedural Use

1. After the manifold is in place (and the console arm extended over the patient, if necessary), rotate the cool down valves to the open position and switch the desired probe controls to STICK. By allowing the manifold delivery lines to cool for several minutes, delays will be minimized when probes are connected.

2. After this cool down period, switch all probes to OFF.

Connecting a Probe

1. Connect a flexible delivery tube to a port on the manifold. If an adjustable probe is being used, first set the desired freezing length by sliding the internal return tube to that length. Then screw the probe's Teflon probe connector to the delivery tube connector on the end of the delivery tube, being careful to not bend any tubing.

2. Repeat for each probe instrument to be used during the operation.

If a fixed length probe is being used, simply connect it to the delivery tube.

Setting a Temperature

The probe temperature setpoint control is functional in the COOL mode only. The setpoint is adjusted by simply depressing the push buttons, either above the desired digit to decrease temperature or below the digit to increase the temperature.

The larger the number value the more negative or lower the temperature.

Figure 6:
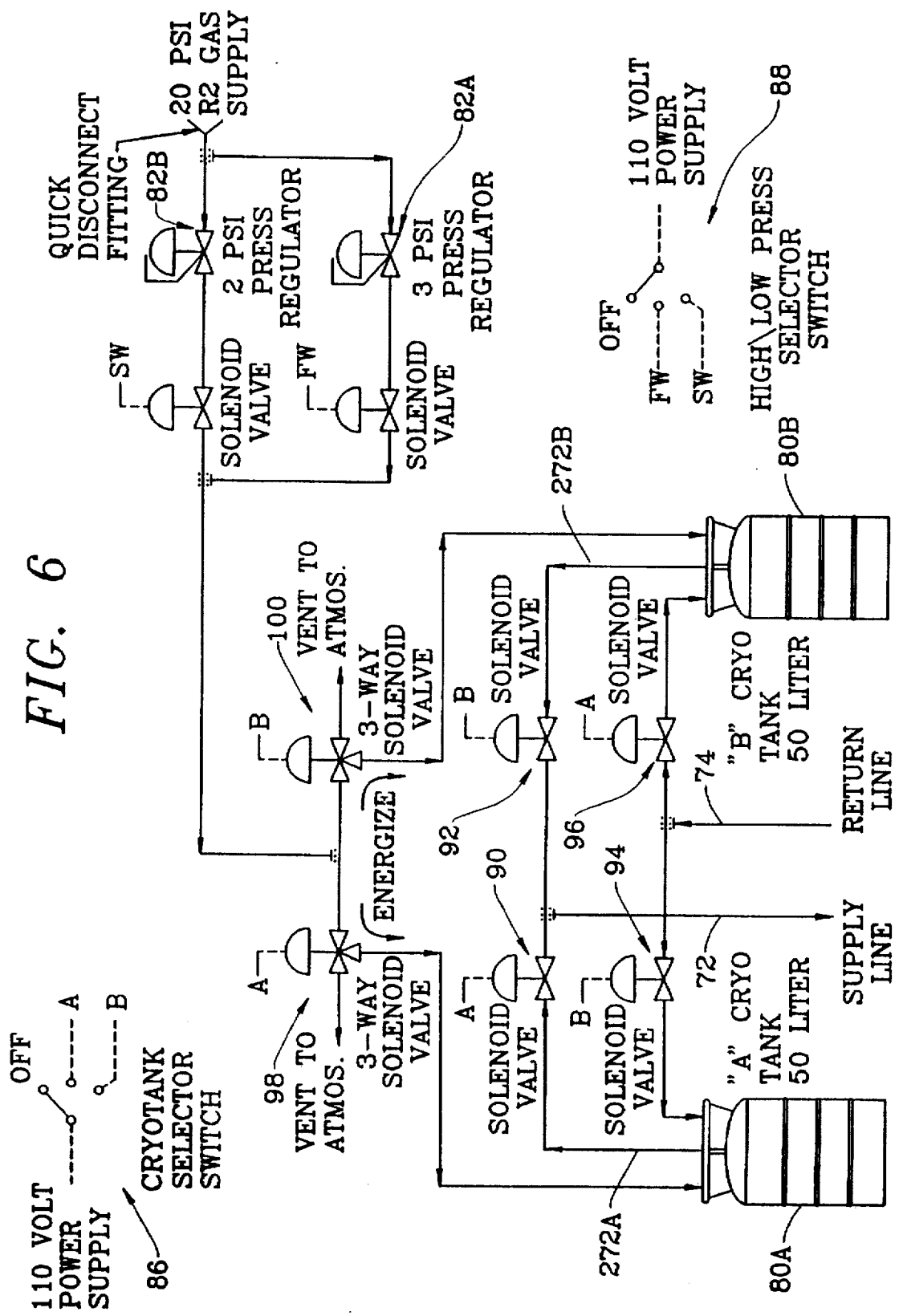
FIG. 6 is a schematic flow diagram according to the invention of the valve assembly for pressurizing liquid nitrogen supply vessels forming part of a closed cycle refrigeration and recovery system for cryogenic liquid refrigerant.

The setpoint temperature may deviate from the displayed temperature by several degrees at any given moment. This will happen when the temperature is being controlled by the on-off switching of a valve. This will produce a temperature that is cyclic around the setpoint. In this regard, temperature control can be accomplished using the temperature control system such as shown in FIG. 6 of the aforementioned U.S. Pat. No. 4,946,460, incorporated herein by reference thereto.

Probe Cooling/Freezing

After the desired temperature has been set, the probe can be activated by depressing the COOL push button. This switch will illuminate and the OFF light will go out indicating that the probe is now active. After a brief period of time, the probe will begin to cool down to the selected temperature.

Probe Thawing/Heating

When it is desired to warm the probe for removal, depress the THAW push button. The COOL light will go out and the THAW light will illuminate. The thawing temperature will normally be internally set at 37° C. and may not be adjustable.

Control Location Selection

At any time during the procedure, control may be switched between the mobile cart's controls and the manifold's controls by simply switching the Control Selector Switch on the mobile cart. While this feature permits maximum flexibility of use, care must be taken to insure that the control parameters are set identically on both units. Otherwise, disruptions to the normal course of the procedure could result.

Referring now to FIGS. 1–8 of the drawings, an embodiment of a sub-cooling refrigeration system based on indirect evaporative cooling will be described. The indirect evaporative cooling system used to sub-cool the liquid nitrogen ($LN_2$) flowing therethrough is shown generally at 10 and includes vacuum chamber 11 with enclosure 12 defining receptacle 13 and cover assembly 14 which is clamped vacuum tight to the enclosure via metal clamp members 16 and plastic knobs 17 and cover gasket 18.

Figure 4:
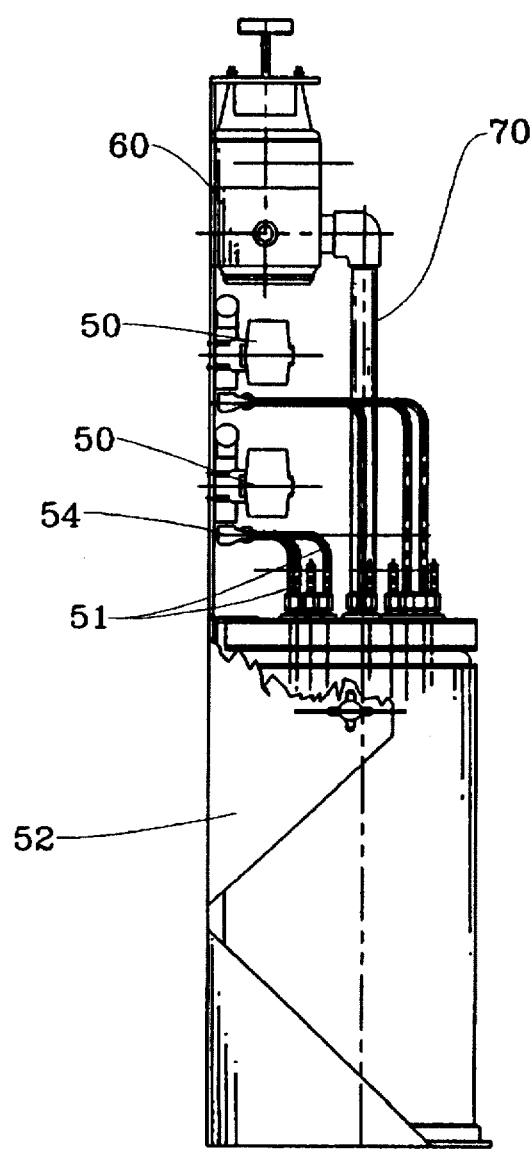
FIG. 4 is a side elevation view of the heat exchanger valve assembly and mounting plate of FIG. 3.
Figure 5A:
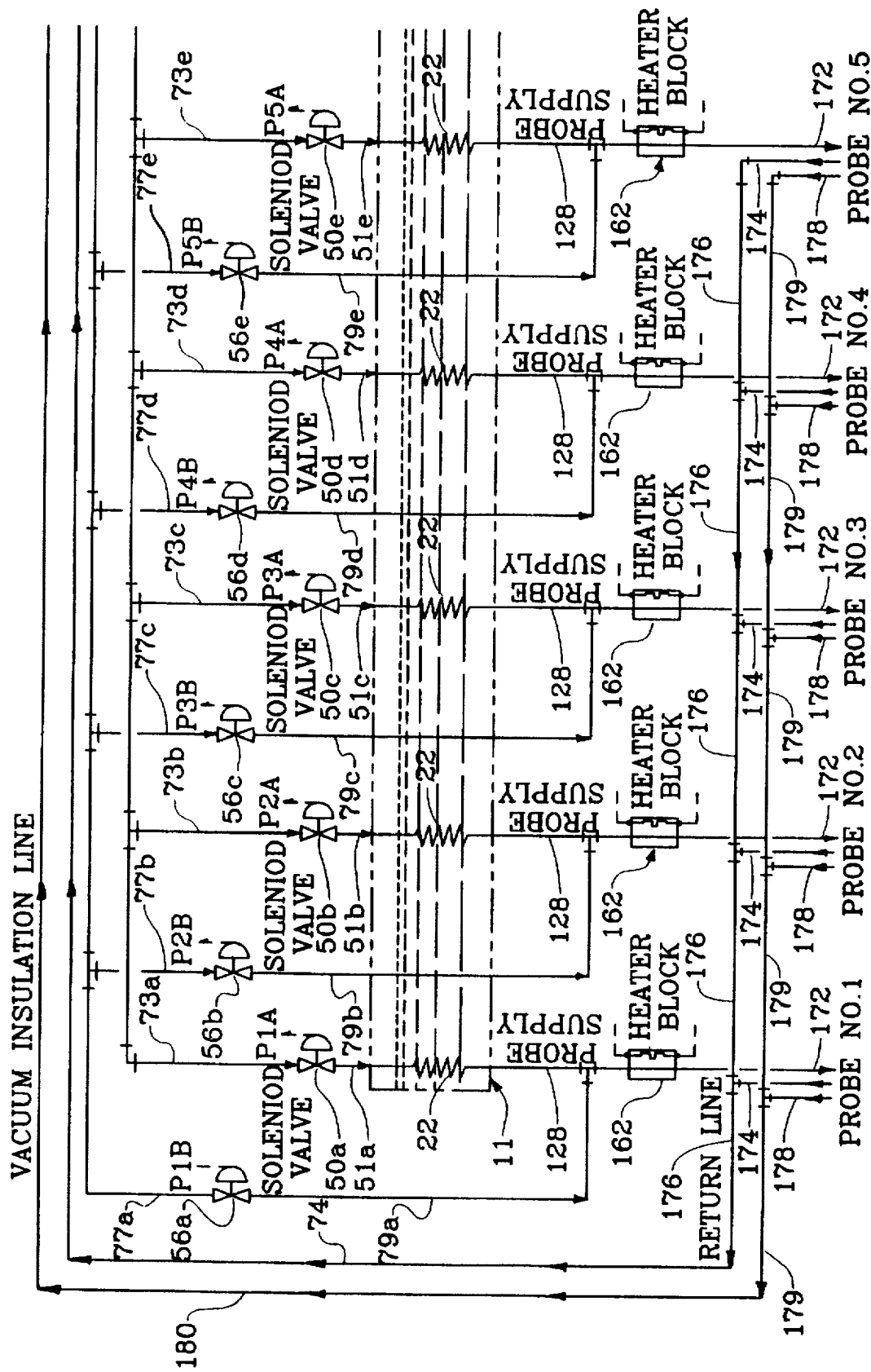
FIG. 5 is a schematic flow diagram of the operation of the indirect evaporative cooling refrigeration system including valve assembly and vacuum chamber for generating sub-cooled liquid refrigerant in the embodiment illustrated in FIGS. 1–4.
Figure 5B:
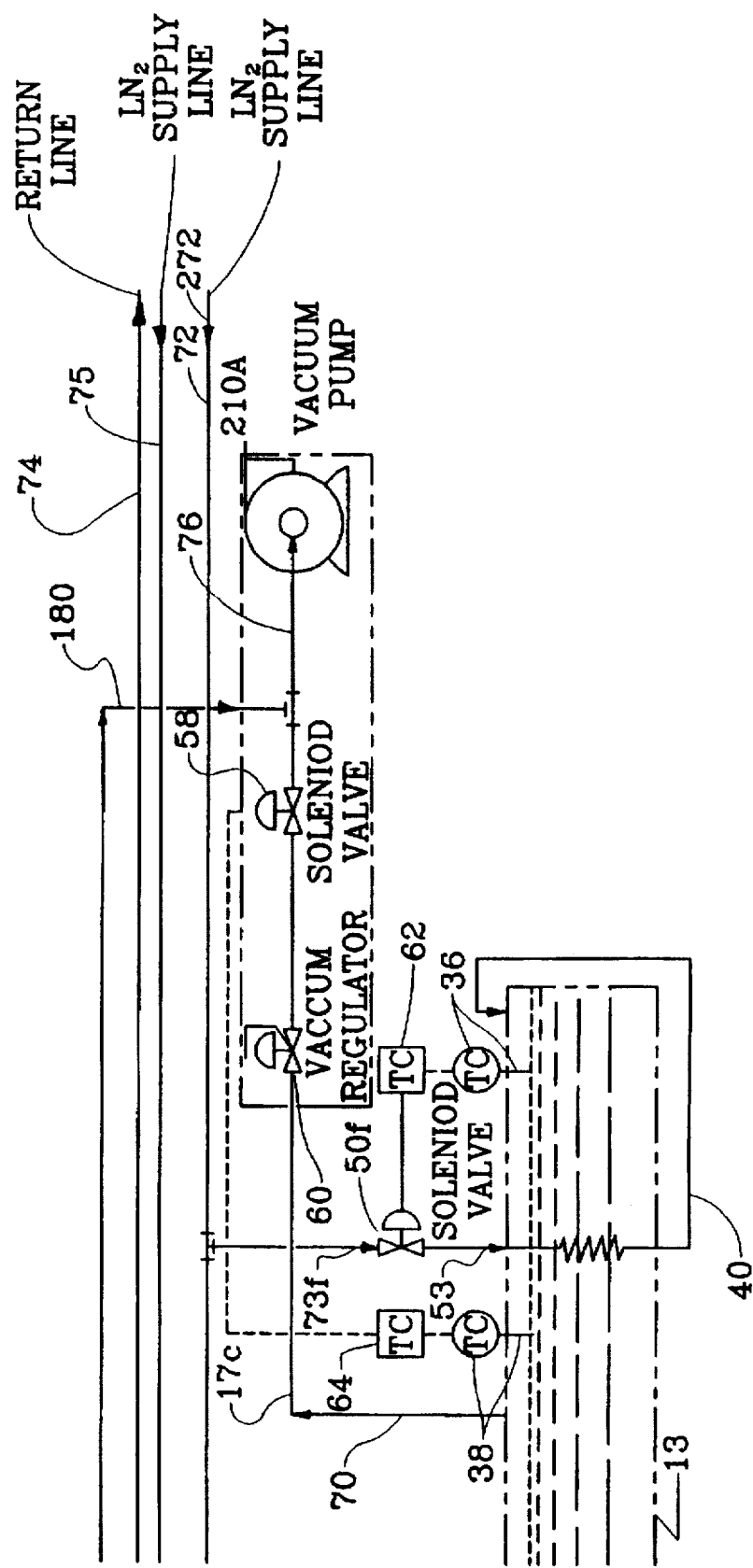

Cover assembly 14 includes counter-bored through-holes 20 for receiving therein the inlet ends 24 and outlet ends 26 of heat exchanger coils 22 for each cryoprobe. The coil inlet and outlet ends are each fitted with "swagelok" bulkhead unions 30 including threaded portions 28 which are securely bolted to the cover assembly with a series of nuts 31 and to the heat exchange tubing with nut/furrel 27. A second nut/furrel 29 provides connecting means for the tubing from the control valves (FIGS. 3–5). In the embodiment shown in FIGS. 1–5, five heat exchanger coils 22 are shown for connection to five cryoprobes, however, by adjustment in size and configuration, the vacuum chamber 11 can house from 1 up to about 10 heat exchanger coils to service from 1 to 10 cryoprobes. The heat exchanger coils in the drawings are formed from ¼" O.D.×0.035" wall refrigeration grade copper tubing of total length, per unit, of approximately 7 feet 9 inches. Four ½ inch copper securing straps 32 are lapped around the coiled tubing 22 and their ends are soldered together.

Also located within receptacle 13 is liquid nitrogen pre-cooler heat exchanger helically coiled copper (refrigeration grade) tubing 40, the individual coils of which are spaced apart by Teflon spacers 48 mounted flush against the wall 15 of receptacle 13. The outlet 42 of heat exchanger tubing 40 is located somewhat below the uppermost coil to discharge precooled liquid nitrogen free of $N_2(g)$ into receptacle 13. The inlet 44 of tubing 40 extends through and is fluid and vacuum tightly sealed to cover 14 in the same manner as for heat exchange coils 22, using a swagelok bulkhead union with fitting for connection to a source of liquid nitrogen via appropriate tubing.

Centrally located in cover 14 is opening 34 for receiving vacuum pipe line 70 to vacuum regulator 60 (see FIGS. 3 and 4). Vacuum pipeline 70 may be secured to opening 34 with, for example, a 1½ inch×¾ inch NPT reducing bushing 71. Fixed above the vacuum chamber to mounting plate 52 are six solenoid valves 50 for controlling the $LN_2$ input from $LN_2$ supply pipe 72 to each of the five heat exchange coils 22 via stainless steel tubes 51 and to the pre-cooler heat exchanger 40 through stainless steel tubing 53 which connects the outlet 54 of each valve 50 to the respective heat exchanger via connecting nuts 29. The vacuum regulator may, alternatively, be mounted in the mobile cart.

Thermocouple 36 is also fitted within the slush receptacle of the vacuum chamber via opening 35 in order to measure the temperature within the receptacle. The tip of the thermocouple will extend into the chamber to below the level of the $LN_2$ introduced through the pre-cooler heat exchanger tubing. For more sensitive temperature measurement additional thermocouples may be provided at different levels within the receptacle.

Referring now to FIG. 5, the operation of the sub-cooling refrigeration system is illustrated by a schematic flow diagram showing the connection to the input of each solenoid valve 50a–f from an $LN_2$ supply source (e.g., from the dewars of the mobile cart) via main supply line 272 and supply pipe 72 and connecting lines 73a–e and from the output of each of the five solenoid valves associated with the five cryoprobes via tubing 51a–e to the respective heat exchange coils 22 and from the 6th solenoid valve via connecting line 73f and line 53 to the pre-cooler heat exchange tubing 40. Also shown are manifold delivery lines 128 from each heat exchanger coil 22 to the respective probe connection ports for delivery via flexible $LN_2$ delivery tube 172 to each cryosurgical probe. A return line 74 is provided for returning refrigerant ($LN_2$ or "cold" $N_2(g)$) from the cryoprobe(s) to an $LN_2$ storage dewar or for venting to the atmosphere. Vacuum line 70 is connected via gas return passageway 170 to vacuum regulator 60 and optional solenoid valve 58 which in turn is connected via vacuum line 76 to a vacuum source (e.g. vacuum pump 210A).

In operation, after cover assembly 14 is tightly clamped by clamp members 16 to vessel 12, and valves 50a–e in the closed position, and valve 50f in the open position receptacle 13 of vacuum chamber 11 is filled via supply line 72, connecting lines 73f and 53, valve 50f and coils 40 with $LN_2$ to immerse the coils of the heat exchange tubes 22 and the end of thermocouple 36 with $LN_2$. After the receptacle is filled with $LN_2$ to above the level of the thermocouple 36 such that a temperature of, for example, about −190° C. or lower, is sensed by the thermocouple, valve controller 62 causes solenoid valve 58 to close, and a vacuum is drawn by vacuum pump 210A via vacuum lines 170, 70, vacuum regulator 60, valve 58, and vacuum line 76 to evacuate chamber 13 to a pressure of about 1.81 to 1.82 psia (pounds per square inch absolute). At this low pressure, the $LN_2$ temperature drops to nearly −214° C. Once the temperature of the $LN_2$ refrigerant is lowered to the desired sub-cooled temperature, one or more of the solenoid valves associated with heat exchanger coils 22 are activated manually or via suitable control means. Furthermore, when optional thermocouple 38 senses the desired sub-cooled temperature of the $LN_2$ refrigerant at or near the bottom of the receptacle, valve actuator 64 may cause solenoid valve 58 to close with the vacuum insulation lines 76, 180, 179 and 178 to the cryoprobe instrument(s) being evacuated to the lower vacuums dependent on the rating on the vacuum pump. Therefore, the vacuum for thermal insulation can be much higher than the vacuum for sub-cooling in vacuum chamber 11. Depending on the preset temperature for each cryoprobe, the associated solenoid valve may remain in the open position (to achieve maximum cooling of the probe tip) or may vary between the open and closed positions or remain partially opened, depending on the type of valve, to provide higher probe tip temperatures. After the tumor or other tissue has been completely frozen and destroyed, the valves 50a–e will be closed and the probe tips will be thawed to allow removal of the probe tip from the tumor. Thawing may be accomplished by electrical heating coils located in the probe tip but, may also be accomplished via introduction into the probe tip of warm fluid, e.g. warm $N_2(g)$ or warm air, such as shown, for example, using the system shown in the flow diagram of FIG. 5.

According to this arrangement, main supply line 75 carries nitrogen gas from a suitable source (not shown) and is connected to each probe's delivery line 172 via branch lines 77a–e, solenoid valves 56a–e, and secondary branch lines 79a–e. Optional electrical heaters 162 may also be provided for supplying additional heat to the gas flowing through the $LN_2$ delivery lines 172. The heating elements may be located on line 128 or on line 172 within the flexible delivery tube 254.

A process flow diagram for a system for pressurizing the liquid nitrogen supply tanks 80A and 80B from a nitrogen gas ($N_2(g)$) supply line, such as routinely available in a hospital surgical operating room is shown in FIG. 6. A selector switch 86 can be switched between the "Off" position or positions "A" or "B" for pressurizing either Dewar 80A or 80B from the $N_2(g)$ supply using either high or low pressure regulators 82A, 82B controlled by regulator selector switch 88, and for controlling the selection of Dewar 80A or 80B to supply $LN_2$ to main supply line 72 via lines 272A and 272B, respectively. When solenoid valve 90 is in the open position, solenoid valves 92 and 94 will be in the closed position and solenoid valve 96 will be in the open position to receive $LN_2$ from return line 74 to fill tank 80B. When switch 86 is in the "Off" position, 3-way solenoid valves 98 and 100 will be closed. When switch 86 is set to position "A" for pressurizing tank 80A and using tank 80A as the LN2 supply tank valve 100 will also be closed or may be vented to the atmosphere. A level or volume detector (not shown) in tanks 80A and 80B may also control the opening and closing of valves 98 and 100.

Figure 7:
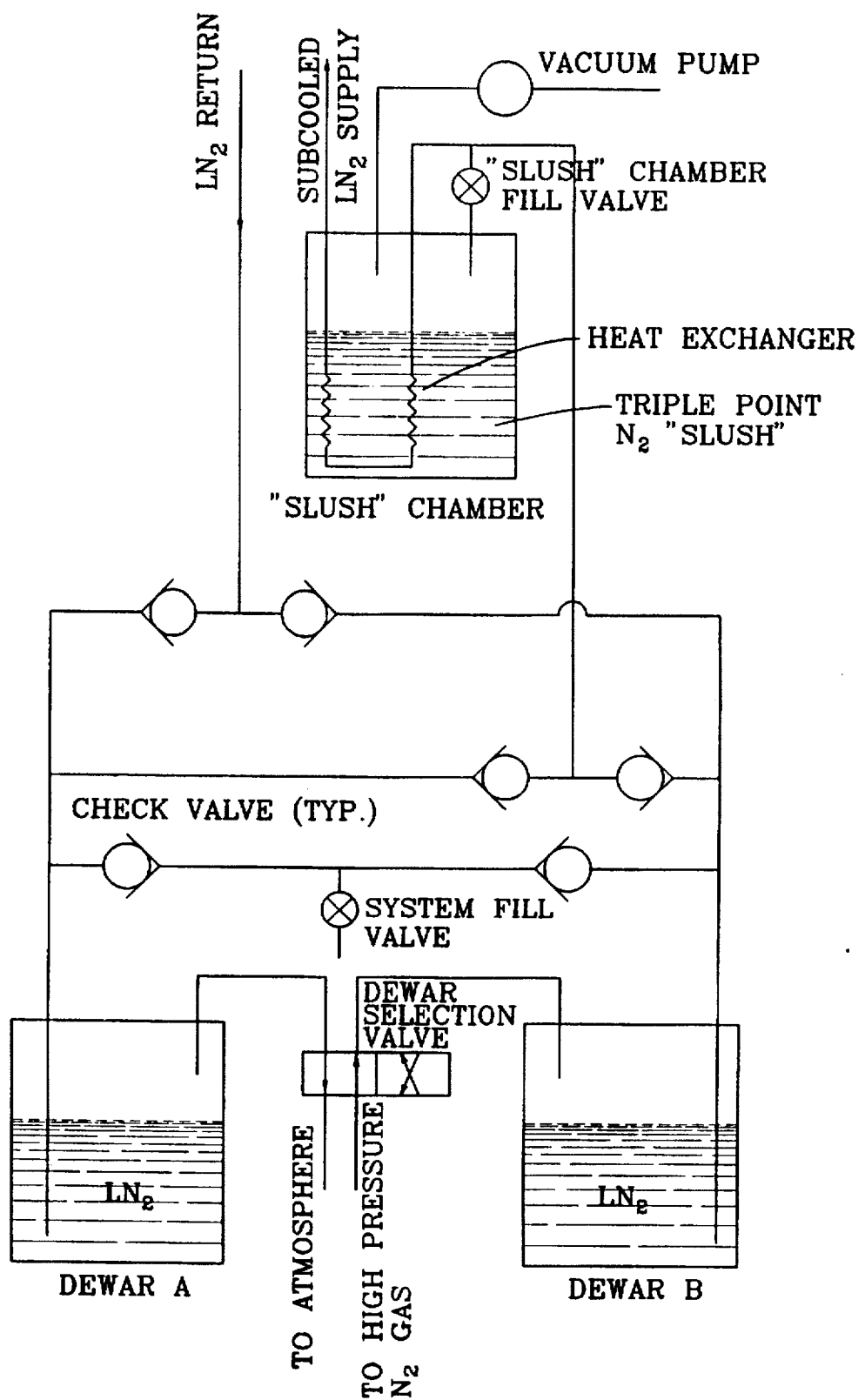
FIG. 7 is a simplified schematic flow diagram of an indirect evaporative cooling refrigeration system with a single heat exchanger incorporating the liquid nitrogen recovery system of FIG. 6.

Another form of simplified flow diagram for an indirect evaporative cooling refrigeration system with a single heat exchanger in the vacuum chamber and a dual dewar $LN_2$ supply and recovery vessel system is shown in FIG. 7. In FIG. 7 ball and seat check valves are shown to simplify the piping, however, any other plumbing arrangement may be selected as is well known in the art. The check valves allow flow of liquid only in the direction of the seat, flow in the direction of the ball forces the ball into the seat and closes the valve. The system fill valve is used to fill either dewar A or dewar B with $LN_2$. The dewar selection valve is used to select the dewar which will be pressurized with $N_2(g)$ to provide the driving force for transporting the $LN_2$ to the refrigeration system, which in the embodiment of FIG. 7 is an indirect evaporative cooling system shown with only a single heat exchanger in the vacuum or "slush" chamber.

Figure 7A:
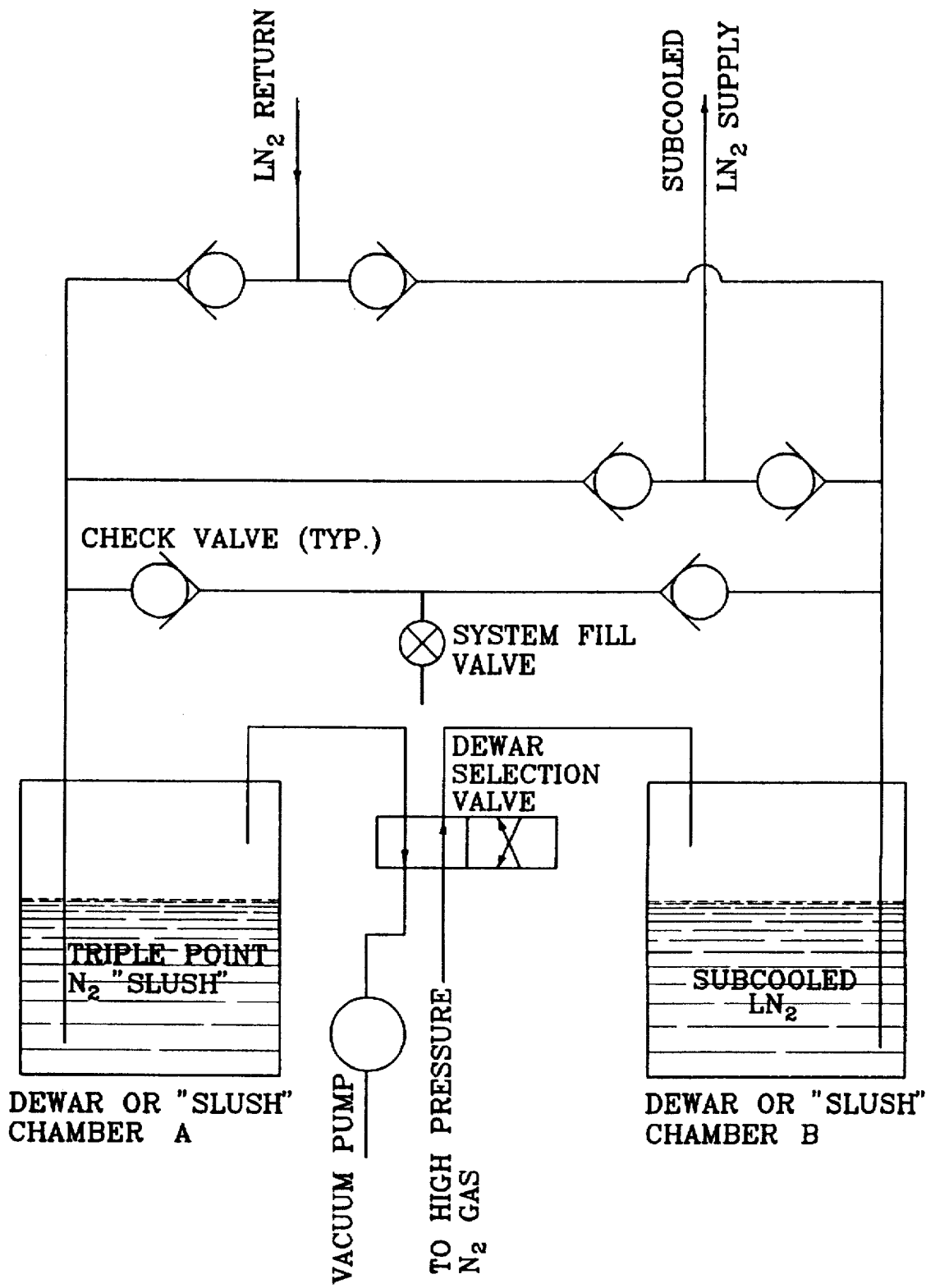

In the modified flow diagram of FIG. 7-A, the "slush" chamber with heat exchanger is eliminated and its function is replaced by dewars A and B which controlled by the dewar selection valve, alternatively function as the sub-cooling refrigeration system or the collection dewar for returned $LN_2$ from the cryoprobes. Thus, the system of FIG. 7A usls directly evaporatively cooled $LN_2$ as the sub-cooled refrigerant [$SN_2$] to be transported to the freezing zone of the one or more cryoprobe instruments. In the embodiment of FIG. 7A high pressure $N_2(g)$ is again used as the driving force for the $SN_2$ supplied to the cryoprobe(s).

However, in still another modification, as shown by the simplified flow diagram of FIG. 7-B only a single vessel may be used to function simultaneously as the "slush" chamber and $LN_2$ recovery dewar. In this embodiment a liquid cryogen pump is used to increase the pressure of the $SN_2$ generated in the "slush" chamber to transport the $SN_2$ refrigerant to one or more cryoprobe instruments.

Figure 7B:
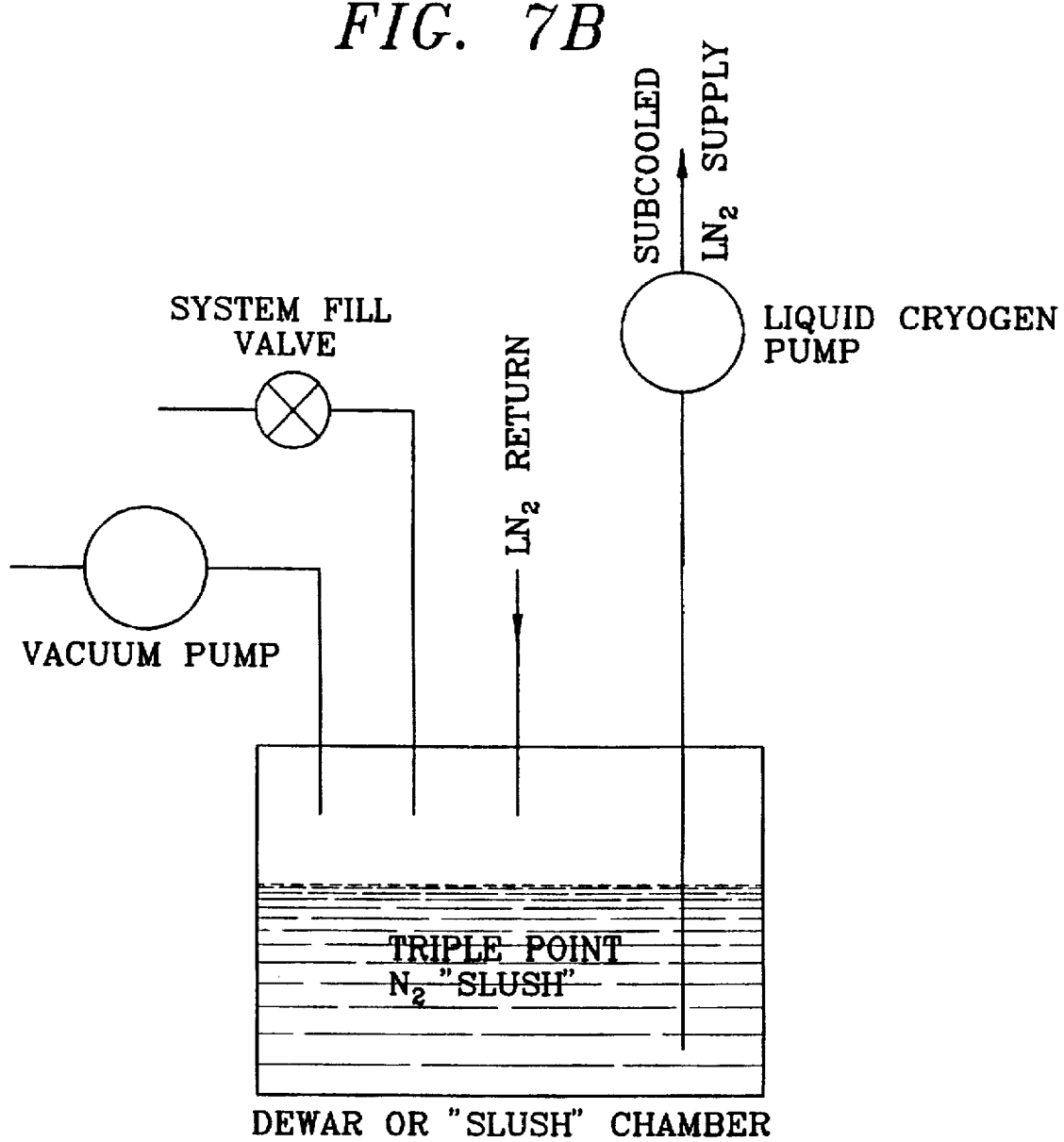

The alternative embodiments of FIGS. 7-A and 7-B which employ direct evaporative cooling to generate the $SN_2$ supply for the cryoprobe(s) will generally be able to deliver colder $SN_2$ than the indirect evaporative cooling system of FIG. 7 in view of the inherent inefficiency (somewhat less than 100%) of the submerged heat exchanger coils. The embodiment of FIG. 7B also eliminates the need for pressurized $N_2(g)$ required in arrangements shown in FIGS. 7 and 7-A. Also, in the embodiment of FIG. 7-B one cryogen pump may be used to serve multiple probes or each probe may be served by its own cryogen pump, and the cryogen pump may conveniently operate with continuous or proportional flow to provide control of the amount and rate of $SN_2$ supply to each probe.

It should also again be noted that the sizes of the dewars A and B in FIGS. 7 and 7-A or the single dewar/slush chamber in FIG. 7-B can be sized to provide the total on-board (i.e., stored in themobile cart) $LN_2$ requirements for a surgical procedure. Alternatively, the dewars may be relatively small in which case a large on-board dewar connected to the system fill valve may be used to supply the total $LN_2$ requirements.

Figure 8:
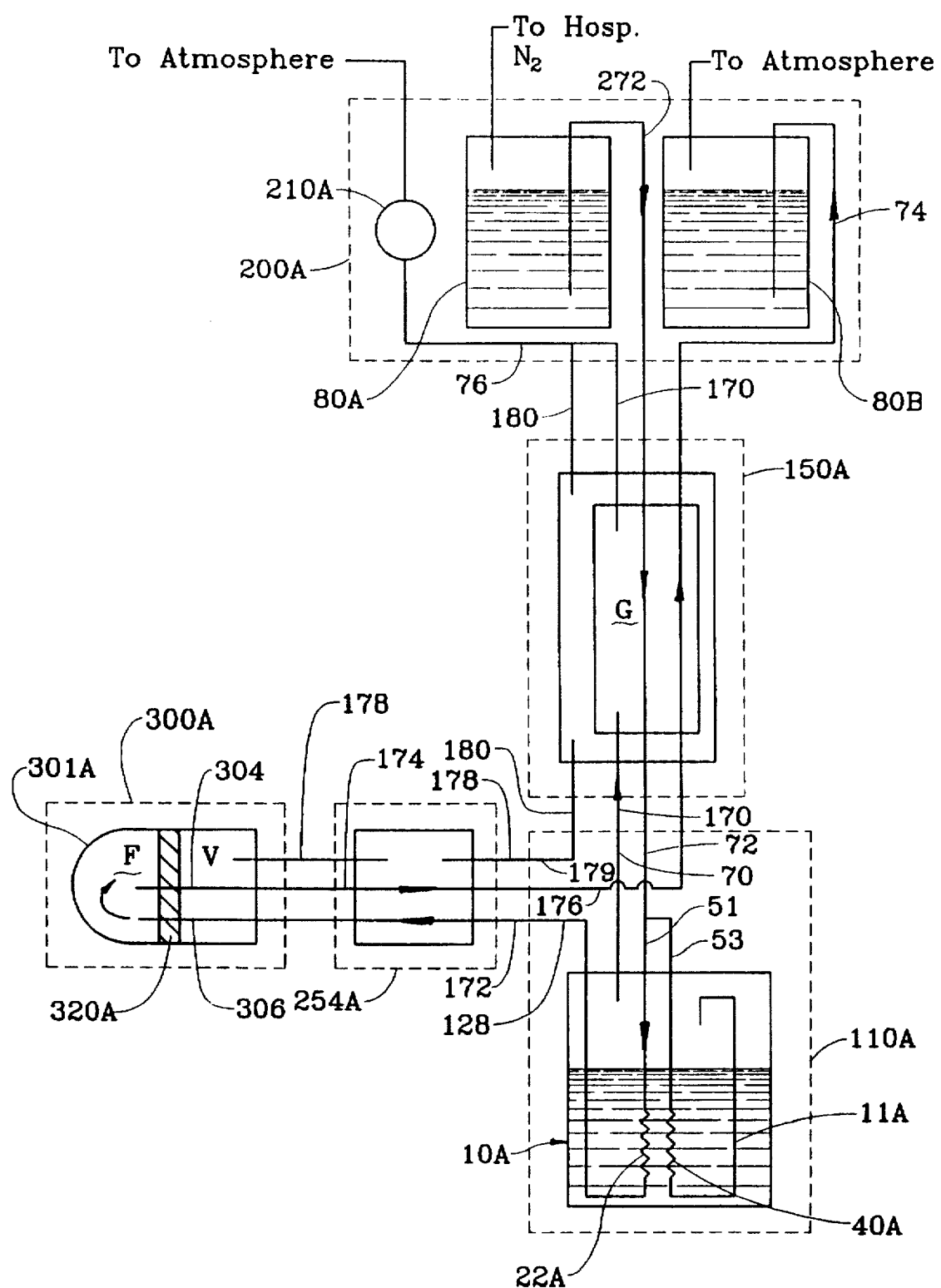
FIG. 8 is another simplified schematic flow diagram of an embodiment of the cryosurgical system similar to FIG. 7, including the supply and delivery lines to a single cryoprobe instrument, including active vacuum insulation, according to the invention.
Figure 8A:
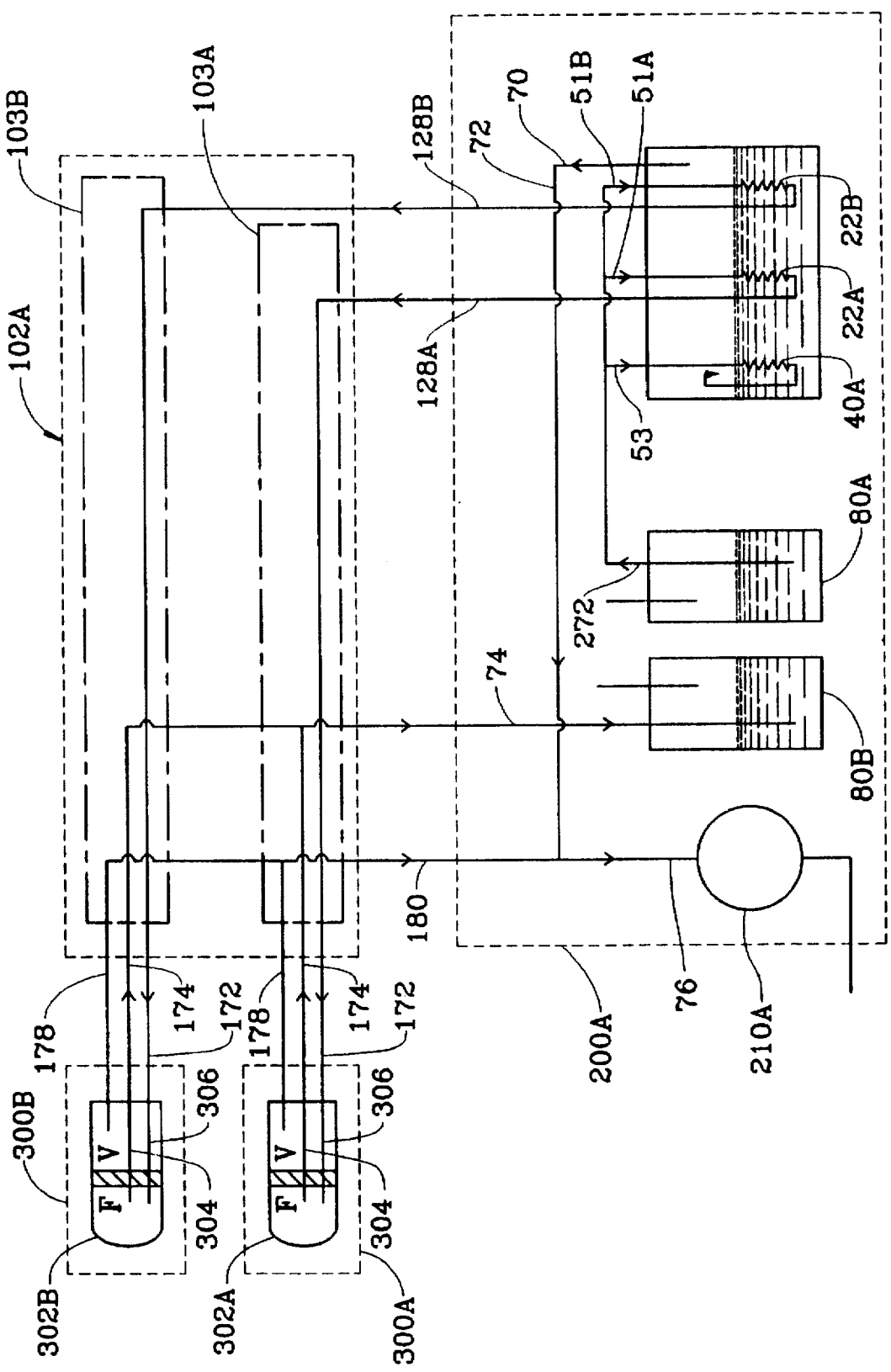

A schematic flow diagram of the various components of the cryosurgical system according to one embodiment of the invention and their connecting tubing is shown in FIG. 8.

A mobile cart is represented by broken box 200A and includes therein $LN_2$ supply dewar 80A and $LN_2$ return dewar 80B, and vacuum pump 210A.

A mobile manifold is represented by broken box 110A and includes therein the indirect evaporative sub-cooling refrigeration system 10A including vacuum chamber 11A with a single heat exchanger coil 22A and pre-cooler heat exchanger tubing 40A.

A single cryoprobe tool is represented by broken box 300A and includes probe shell 302A, and seal member 320A separating the freezing zone F from vacuum zone V. A flexible delivery hose, represented by broken box 254A is located between probe 300A and manifold 110A. Stainless steel external supply tube, represented by broken box 150A is located between the mobile cart and the manifold.

In operation, vacuum chamber 11A is filled with $LN_2$ from $LN_2$ supply dewar 80A via heat exchanger coil 40, line 53 and supply lines 72 and 272 which passes through supply tube 150A. Vacuum pump 210A is then activated to withdraw $N_2(g)$ from vacuum chamber 11A via vacuum pipe lines 70, 170 and 76 to lower the temperature of the $LN_2$ in the vacuum chamber to about −214° C. Then $LN_2$ from dewar 80A is transported via lines 53, 72 and 272 through supply tube 150A to heat exchanger coil 22A where its temperature is lowered by the $LN_2$ refrigerant in the vacuum chamber to a temperature below the normal boiling temperature of nitrogen, such as about 208° C. This sub-cooled $LN_2$ from heat exchanger 22A is conveyed to the freeze zone F via manifold line 128, flexible $LN_2$ delivery hose 172 (through delivery tube 254A) and probe internal $LN_2$ supply line 306. After extracting heat from the probe shell to reduce the external wall temperature of the shell in the freeze zone F to as low as about −206° C. (depending on the flow rate of $LN_2$ into the probe), the spent $LN_2$ refrigerant exits the freeze zone via exhaust line 304 and is conveyed to return dewar 80B through external flexible refrigerant return hose 174 (through delivery hose 254A), line 176 (in manifold 110A), and line 74 (through supply tube 150A). At the same time, vacuum pump 210A withdraws gas from vacuum chamber V of the probe via vacuum lines 178 (through delivery hose 254A) 180 (through supply tube 150A) and 76 while also creating vacuums in delivery hose 254A and supply tube 150A to provide thermal insulation for the tubes and pipes through which the cryogenic refrigerant is flowing. Also, the cold $N_2(g)$ fills the annular region G in supply tube 150A to provide additional thermal insulation for the $LN_2$ flowing through the $LN_2$ supply lines and return lines.

Figure 9:
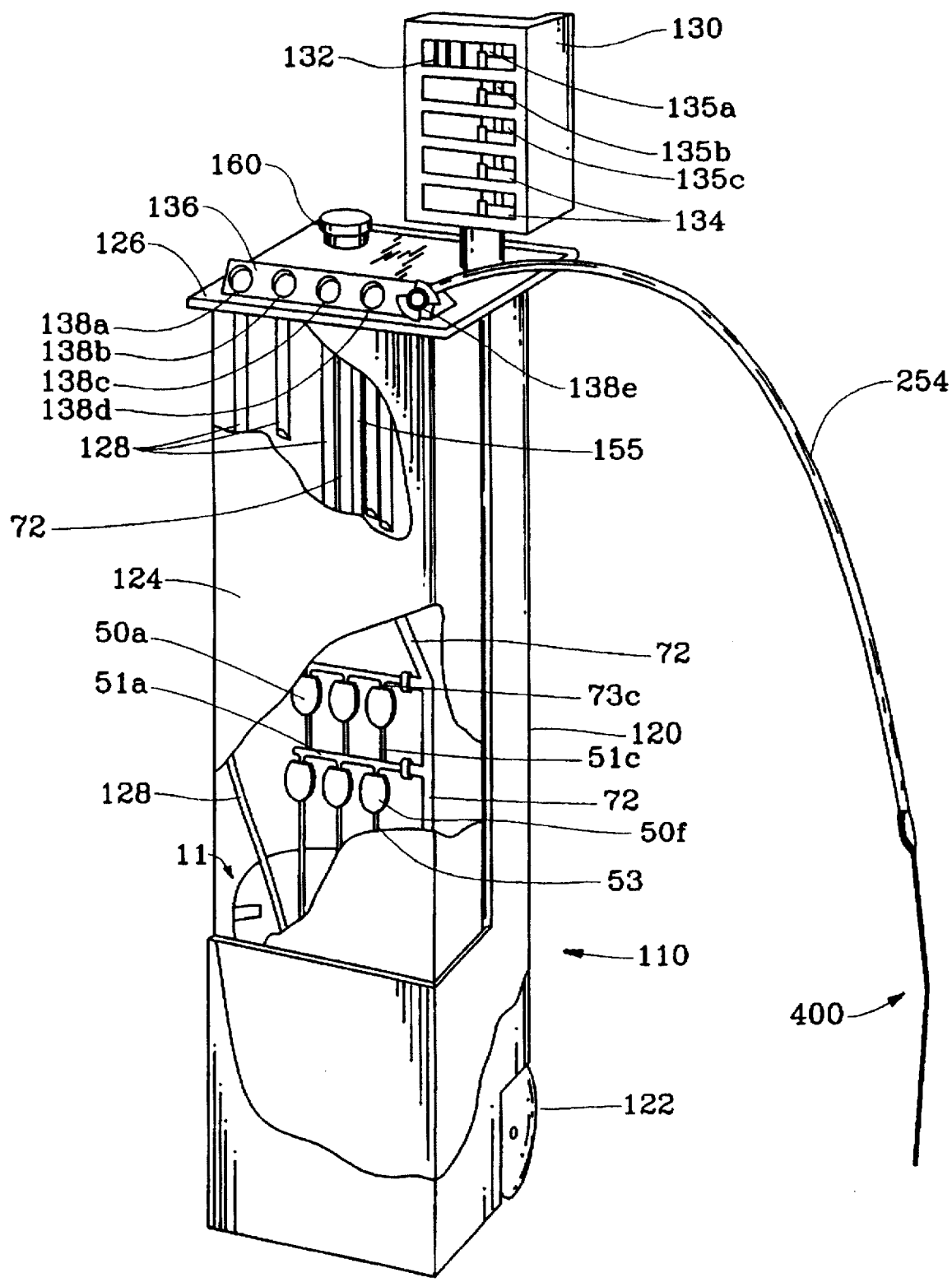
FIG. 9 is a perspective view, in elevation, of an embodiment of a mobile manifold assembly according to the invention, with a portion of the front panel and manifold cover broken away to provide an internal view of the sub-cooling refrigeration system and valve assembly and plumbing contained therein.

In one embodiment of the invention, as shown in FIG. 9, the evaporative cooling refrigeration system including vacuum chamber 10 and solenoid valves 50a–f as shown in FIGS. 1–5 as well as solenoid valves 56a–f (not shown) may be stored in a mobile manifold unit whereby the sub-cooling refrigeration system may be easily transported as close as possible to the operating table.

One embodiment of a manifold assembly is shown generally at 110 in FIG. 9 with the front panels partially broken away to provide a partial view of the sub-cooling refrigeration unit, solenoid valves, and $LN_2$ supply and vacuum lines into the manifold.

The manifold assembly includes housing 120 movable on wheels 122 located at the base thereof. A removable panel 124 provides access to the vacuum chamber 11 and associated valve mechanisms contained within the manifold assembly. On the rear portion of upper ledge 126 of housing 120 a temperature display and temperature control panel 130 is provided and includes large character, segmented vacuum fluorescent displays 132 and associated lighted push-button temperature set-point control switches 134 and mode control buttons 135a, 135b, and 135c for "STICK", "COOL" and "THAW", respectively. The displays may, if desired, be color-coordinated to the individual probes, and, in the illustrated embodiment, up to five probes may be used. On the front portion of ledge 126 delivery tube connector panel 136 is provided and includes five ports 138a–e for receiving the flexible insulated probe delivery tubes 254 (only one being shown) for each of the five individual surgical cryoprobes. Each port is, in turn, connected via manifold delivery tubing 128 to one of the heat exchanger coils, such that the sub-cooled $LN_2$ refrigerant generated in the vacuum chamber housed within the manifold may be transported via its delivery tube 254 to its associated probe tip. In a preferred embodiment, each port 138a–e is also connected to a vacuum source, e.g. pump 210, via vacuum insulation lines 179 (not shown in FIG. 8), 180 and 76 in order to actively maintain an insulating vacuum in each of the probes being used as well as in the delivery tube 254.

In this regard, ledge 126 also includes a supply or utilities port 160 for receiving a main utility supply tube, such as pipe or conduit 150 (see FIG. 17) for introducing $LN_2$, vacuum and electrical utilities into the manifold. Port 160 may thus provide connections to $LN_2$ supply line 72, electrical wiring conduit 155 and vacuum lines 179 (not shown) connected to each of ports 138a–e and to vacuum line 70 (not shown in FIG. 8).

Figure 10:
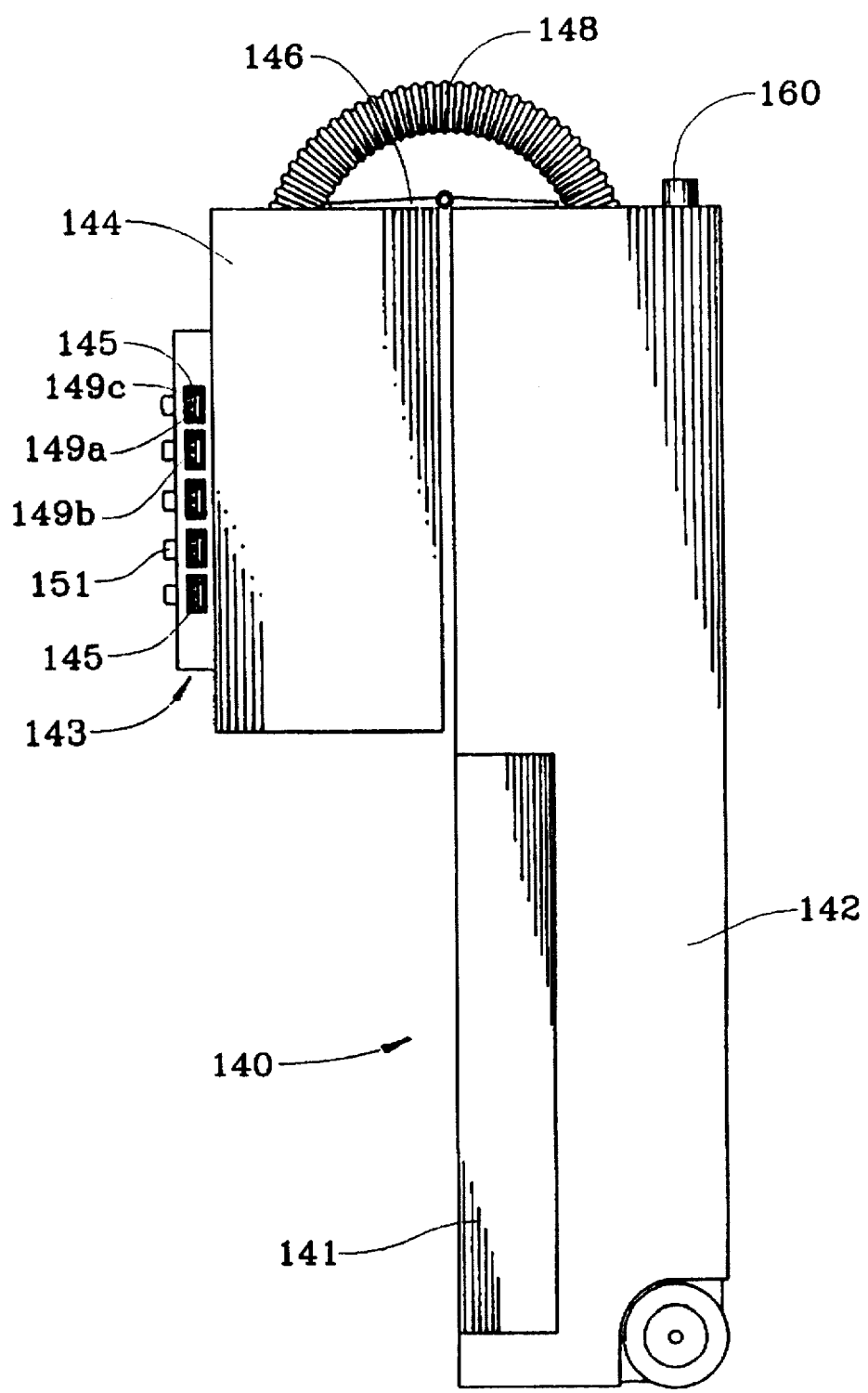
FIG. 10 is a side elevation view of an alternative embodiment of a mobile manifold assembly in its storage position.

An alternative embodiment of a mobile manifold is shown in FIGS. 10–12. In this embodiment, the manifold assembly 140 includes a main housing structure 142 containing therein the sub-cooling refrigeration system and valve assembly with associated supply and delivery lines and a foldable console arm 144. In FIG. 10, the console arm is shown in its folded or storage position. FIG. 12 shows the console arm in its raised or active position for use in a cryosurgical procedure. A locking hinge mechanism 146 locks the console arm in its raised or folded position. Flexible tubing 148 includes therein (not shown) the $LN_2$, vacuum and electrical supply utilities from the main housing 142. Port 160 is provided on the main housing unit to receive the supply pipe 150 for introducing the main $LN_2$, vacuum and electrical utility supplies to the sub-cooling refrigeration unit and to the console arm via tubing 148. The temperature display and control panel is shown at 143 and includes five fluorescent temperature displays 145 and five temperature set-point push-buttons 147. There are also five sets each of three mode control lighted push-buttons 149a, 149b and 149c for "STICK", "COOL" and "THAW", respectively. Five probe connection ports are shown at 151. Again, however, more or fewer probe connection ports with associated temperature controls and displays and mode control switches may be provided. Removable panel 141 provides access to the interior of the main housing wherein the sub-cooling refrigeration system including vacuum chamber 11 and solenoid valves 50 are stored.

An embodiment of a mobile cart is shown generally at 200 with side cover panels shown in phantom to permit viewing of the inside thereof. The mobile cart houses therein on one side thereof vacuum pump 210 and, if desired, a noise suppressor 212, such as a Topaz model 91005-31 Ultra-Isolator Line Noise Suppressor, for suppressing noise from the vacuum pump. A Lesker model AV-ZM-2033C vacuum pump has been found suitable to provide the low vacuum pressures required for the sub-cooling refrigeration system as well as for drawing the active vacuum insulation in the cryosurgical probes. The other side of the cart includes the $LN_2$ storage dewars 80A and 80B. A series of shelves or wire racks 202 are provided for storage of piping, tubing, and other accessories. Handle bar 204 facilitates moving the mobile cart assembly on wheels 206 which are provided with dual brake pedals 208.

In the front portion of the mobile cart, a mobile manifold unit will fit on shelf 214 in the space 219 provided between the forward extending sections 216 and 218 for storage during periods of non-use and for transporting the mobile manifold as required. In the embodiment in which a mobile manifold is not used, space 219 can be used, for example, to store the refrigeration system and associated valves.

Figure 17:
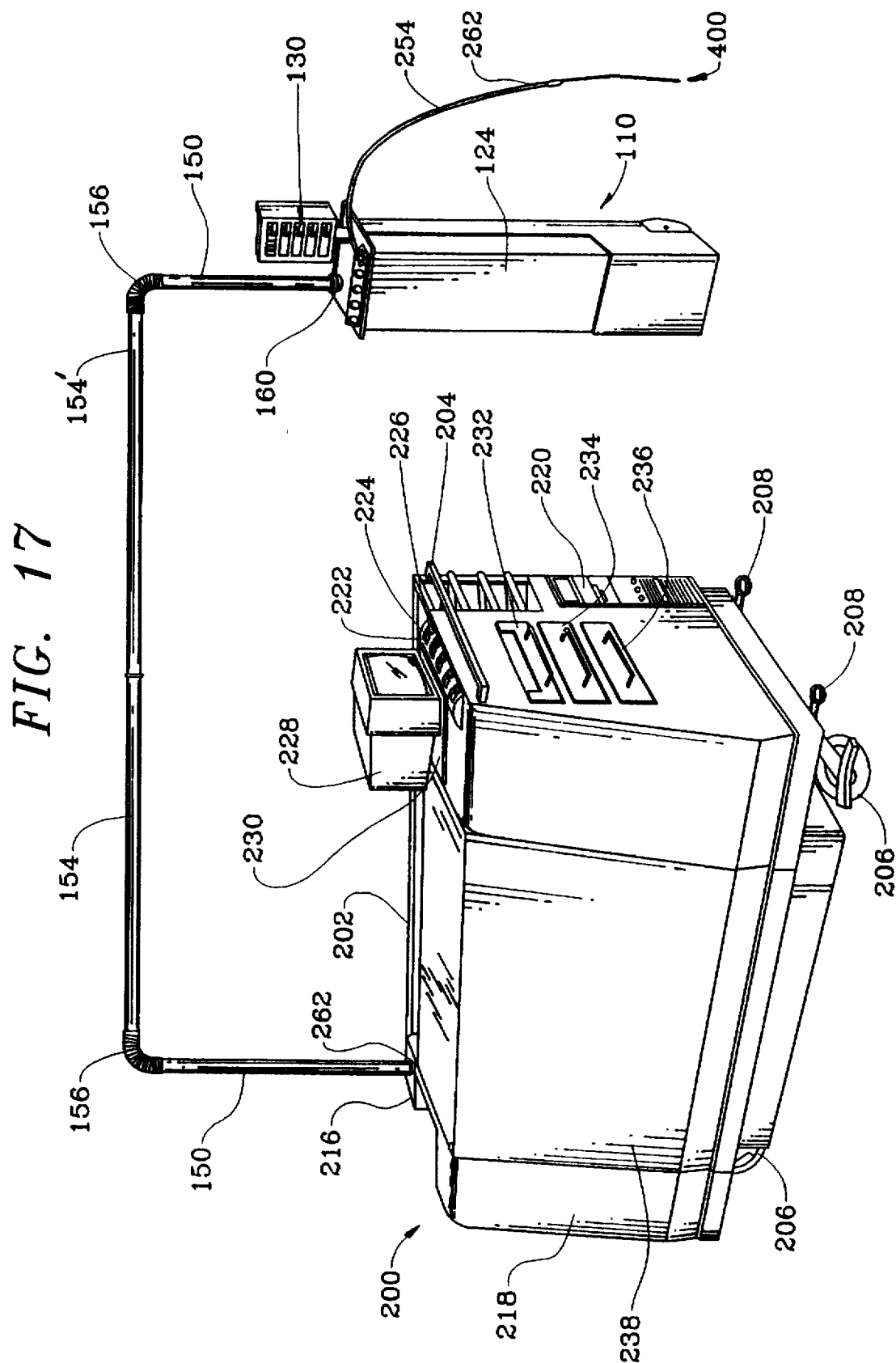
FIG. 17 is a perspective view, in elevation, of one embodiment of the layout of the mobile manifold assembly of FIG. 9 with overhead main utility supply lines connected to the mobile cart of FIGS. 13–16.
Figure 17A:
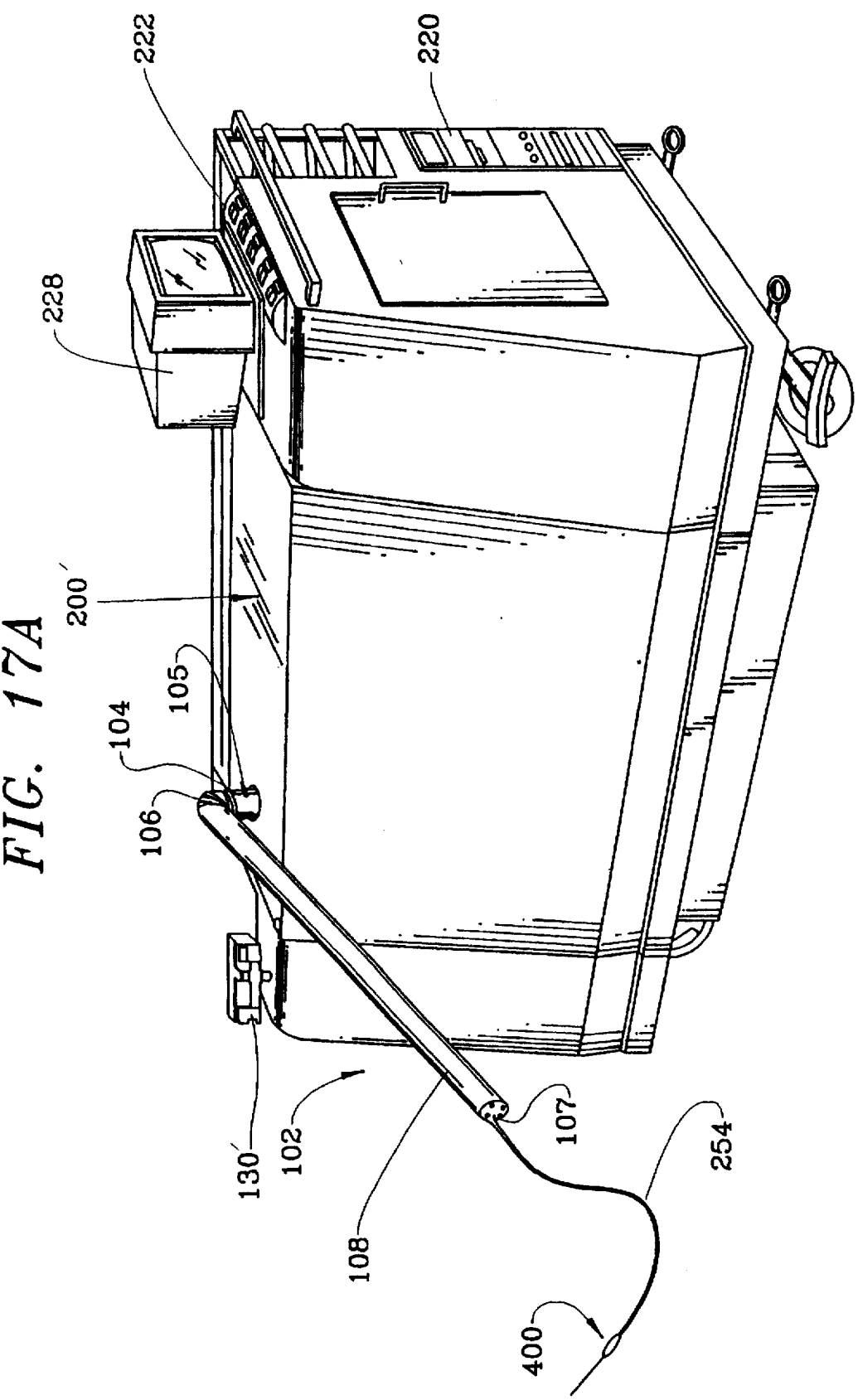

The mobile cart may also include, as best seen in FIG. 17, a computer 220 for data collection, software programming, etc., an alternative control panel 222 with mode selection push-buttons 224 for "STICK", "COOL" and "THAW" modes and temperature set-point controls 226 for each cryoprobe to be used with the system, and a display monitor 228 mounted on rotatable shelf 230 to provide a graphic display of the temperature profile of each probe tip or other information. Preferably, the graphic display for each cryoprobe will be color coordinated with a corresponding color for the temperature displays 132, 145, probe connector ports 138a–e or 151, and/or the delivery tubes 254 connecting the respective probe ports to their individually controlled cryoprobes. For instance, as shown in FIG. 17 a colored band 262 or striping may be provided on the flexible Teflon delivery tube 254 or, if desired, the entire length or a portion of tubing 254 may be coated or painted for easy identification and association of the probe tip temperature display with the probe tip whose temperature is displayed. Numerical identification or other symbols may also be used for identification. In particular, when a plurality, e.g. 5, probe tips are simultaneously inserted into a tumor or other organ or tissue, it might be difficult, in some cases, without some form of color, numeric and/or symbolic coding, to identify the temperature display with a particular probe tip. Of course, if all probe tips are operated at their maximum lowest temperature (e.g. –208° C.), all the temperature displays should have the same reading.

The mobile cart may also conveniently include a drawer compartment 232 for storing a computer keyboard, for example, which would be connected through cables to computer 220, and which can be used, for example, to enter information regarding the particular surgical procedure, such as, patient name, type of operation, date, time, and the like. Additional drawers 234, 236 can provide storage for other items and accessories, including, for example, a supply of surgical cryoprobe connectors and probe tips of different sizes and shapes.

Removable left side panel 238 provides access to the dewars 80A, 80B and associated valves, plumbing and other hardware. Similarly, a removable right side panel 240 will allow access to the vacuum pump 210.

On the upper portion of the right side forward section 216 connection port 242 is provided for receiving one end of main supply pipe 150 for connecting the utilities ($LN_2$, vacuum, electrical wiring) from the mobile cart to the mobile manifold. In setting up the invention system in an operating room main utility supply tubes or pipes 150, 150 may be connected via overhead main supply pipes 154 (two such pipes are shown, but only one or more than two may be used) via flexible elbow joints 156. Within the supply pipe sections 150, 154, 156 (see FIGS. 36–41) are the supply line 272 for the $LN_2$ from $LN_2$ supply tank to the sub-cooling refrigeration system, a vacuum line 170 from the vacuum pump to the refrigeration system for evacuating the vacuum chamber via line 70 and separate vacuum line 180 for withdrawing gas from the insulating vacuum lines 178 and 179 in the delivery tube and manifold to the vacuum chamber in the preferred cryosurgical probes according to the invention, as well as the electrical wiring for feeding power to the various controls, solenoid valves, thermocouples, and the like. A separate electrical connection (not shown) will be provided to feed electrical power to the mobile cart from any available electrical supply in the operating room to power the vacuum pump and for passing through to the manifold assembly. Alternatively, the manifold assembly may be provided with its own direct electrical power inlet for receiving electric power from a source within the operating room. Also, if desired, emergency electric power supply, e.g. 12 volt D.C. current battery or portable electric generator, may be carried within the mobile cart assembly.

Figure 39:
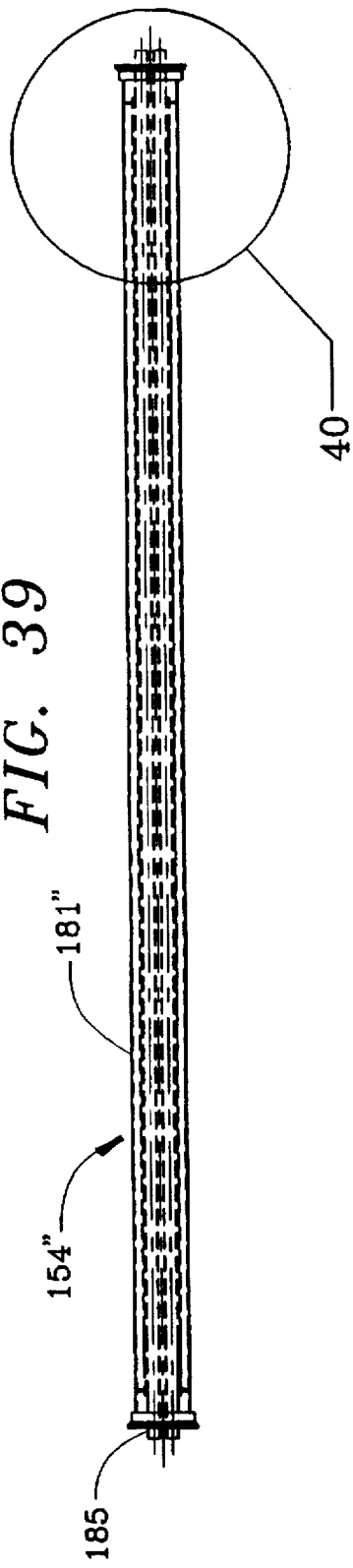
FIG. 39 is a side elevation view, partly in section, of a vacuum insulated cryogenic refrigerant supply tube section according to the invention with a female coupling at one end and extended refrigerant supply and return tubes providing a male coupling at the other end.
Figure 41:
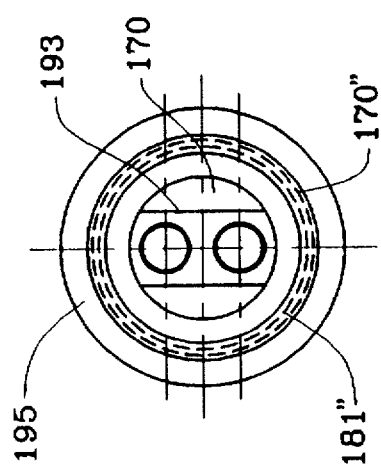
FIG. 41 is an end view of the male coupling end of the supply tube section of FIG. 39.
Figure 40:
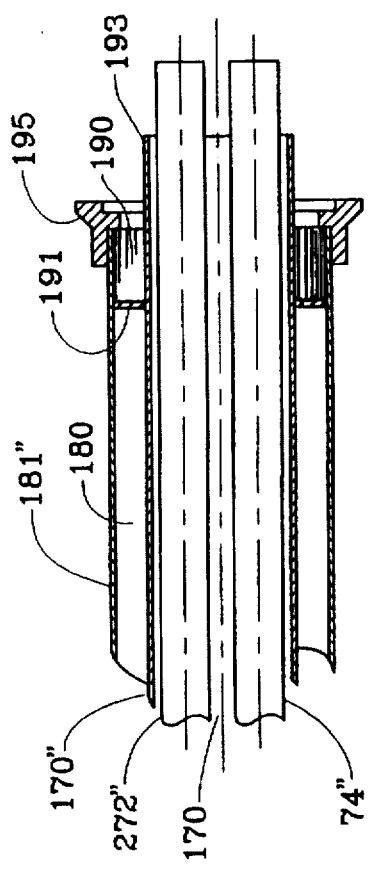
FIG. 40 is an enlarged side sectional view showing the details at end section XL of the male coupling end of the supply tube section of FIG. 33.

An embodiment of a main supply tube segment with two female coupling ends is illustrated in FIGS. 36–38 and a similar embodiment of a main supply tube segment with extending pipes at one end and a female coupling at the other end is shown in FIGS. 39–41. Referring first to FIGS. 36–38 main supply tube section 154' includes outermost pipe 181', concentric intermediate pipe 170' and within pipe 170' are $LN_2$ supply tube 272' and $LN_2$ return tube 74'. Pipe section 181' has identical female Teflon couplings 185 at each end. Each of pipes 181', 170', 272' and 74' are preferably formed from stainless steel. Coupling 185 includes at each end thereof large cylindrical bores 186, 187 dimensioned to fluid tightly receive an end of pipe section 170' and 170" (see FIGS. 39–40) respectively. Smaller cylindrical bores 188 and 189 extend between bores 186 and 187 and are dimensioned to fluid tightly receive the ends of $LN_2$ supply pipe sections 272' and 272" (see FIGS. 39 and 40) and $LN_2$ return pipe sections 74' and 74", respectively. A large spacer disc 191 securely seats pipe section 170' within pipe section 181' while smaller spacer disc 193 securely seats pipe sections 272' and 74' within pipe 170'. As seen in FIG. 42, spacer 191 is substantially square with cut-off corners to fit snugly within pipe section 181' while not blocking the flow passageway 181 formed by the annular space between pipe 181' and pipe 170' and between pipe 181' and connector 185. Passageway 181 extends across the entire length of supply tube sections 154', 154" . . . (as well as sections 150, 150 shown in FIG. 17) and will and will be connected at one end to vacuum line 76 from vacuum pump 210 and at the other end to a common vacuum passageway in the delivery hose and cryoprobe instrument.

The region between tubes 272' and 72' and tube 170' form an $N_2(g)$ return passageway 170 which will be connected at one end to vacuum pipe 70 from the vacuum chamber 11 of the sub-cooling refrigeration system through the entire length of the sections 150, 154', 154" . . . , 150, to vacuum line 76 from pump 210. This "cold" $N_2(g)$ thus provides additional insulation or possibly cooling for the $LN_2$ flowing in $LN_2$ supply passageways 272', 272" . . . and $LN_2$ or $N_2(g)$ flowing in refrigerant return passageways 74', 74" . . . .

Fittings 195 at either end of supply tube section 154' will matting with similar fittings 195 on adjacent tube section 154". An O-ring 198 may be fitted in seat 196 of fitting 195. Furthermore, a clamping ring (not shown) may be fitted over adjoining fittings 195, 195 to form, together with the O-ring, a fluid tight connection.

A similar main supply tube section 154" is shown in FIGS. 39–41 except that Teflon coupling 185 is provided at only one end, pipe sections 170", 272" and 74" extending beyond the opposite end of outermost pipe 181".

To assemble pipe sections 154' and 154" the ends of pipe 170", pipe 272" and 74" extending beyond the end of pipe 181" and fitting 195 will be fitted in the bores 187, 188 and 189, respectively in connector 185 of pipe 181' of section 154' with the confronting ends of pipes 272' and 272" and confronting ends of pipes 74' and 74" abutting against one another and the end of pipe 170" abutting against shoulder 190 of bore 187. The clamping ring may then be fitted over the adjacent fittings 195, 195 on each pipe section.

A modified embodiment of a mobile cart is shown generally at 200' in FIG. 17-A. In this embodiment, L-shaped pivoting arm 102 replaces the mobile manifold and tubes 150, 154. Digital temperature display monitor 130' provides individual temperature displays for each cryoprobe controlled by the control console 222. Pivoting arm 102 includes substantially horizontal extension arm 108 connected to rotatable leg portion 104 by elbow 106. Arm 108 may be rotated to a convenient position and leg 104 may be locked in place by a locking mechanism controlled by lever 105 to prevent further movement of arm 108.

Within cart 200' may be located vacuum pump 210 or other source of suction for withdrawing gas from the vacuum insulation region of each cryoprobe and connecting delivery and supply tubing. Cart 200' may also include therein the on-board supply of $LN_2$ as well as the sub-cooling refrigeration system which may conveniently be located on shelf 214 in space 219.

Each cryoprobe 400 to be controlled from console 222 is connected via its flexible delivery line 254 to a connection port 107 at the open end of arm 108. Each connection part is in turn connected to a conduit 103 through which pass the passageways for transporting sub-cooled $LN_{22}$ refrigerant, used refrigerant and suctioned gas to and from their respective sources or destinations. Alternatively, each delivery line may fully extend through arm 102 for attachment within cart 200' to its respective supply source or destination.

A simplified flow diagram for the modified system of FIG. 17-A is shown in FIG. 9A. Thus, each probe tip 300A and 300B of two cryoprobe instruments 400 is connected to its own conduit 103A and 103B, respectively, within pivotable arm 102A. The operation is otherwise similar to the operation illustrated in FIG. 9.

The embodiment of FIG. 17-A has the advantage of not requiring separate placement of a manifold unit and assembly of the connecting pipes 150,154 from the mobile cart to the manifold unit, while still retaining many of the advantages of a separate manifold but without redundant set of controls.

Referring to FIGS. 18–28, one embodiment of a cryosurgical instrument according to the invention will now be described.

An interchangeable probe tip is shown generally at 300 and includes elongated outer hollow shell 302, internal $LN_2$ supply and refrigerant return passageways with vacuum seal member, shown generally at 301, and probe base 320. Hollow shell 302 includes tapered portion 314 terminating at the rounded closed tip end 310 and open end 316. The $LN_2$ supply and return tubes with affixed seal member are shown generally at 301 and includes refrigerant exhaust tube 304, $LN_2$ supply tube 306 and a generally cylindrical elastomeric seal member 320. The internal exhaust tube 304 and supply tube 306 define therebetween an annular channel 305 through which $LN_2$ or $N_2(g)$ may be withdrawn from the adjustable freezing zone of length L which extends between the closed probe tip (distal) end 310 and the flat or downstream face 322 of sealing member 320.

The sealing member 320 may be formed from an elastomeric material having an embrittlement temperature of at least as low as $-10°$ C., preferably at least as low as $-50°$ C., especially at least $-60°$ C. A silicone elastomer, available from Dow Corning Co. as Silastic, Medical Grade Elastomer MDX4-4515, has an embrittlement temperature of about $-60°$ C., is compressible and easily slidable along the inner wall 303 of probe shell 302, and has proven to be useful as the sealing member. In order to hold the sealing member 320 firmly affixed to exhaust tube 304, copper coil 318 is welded or brazed to the tube 304 and the seal member is fitted over the coil.

The volume of the sealing member is such that it is highly compressed at normal temperature and tightly packed in the annular space 307 defined by inner wall 303 and tube 304. For example, the diameter of the sealing member in the uncompressed state may be the same as the outside diameter of the probe shell 302. Accordingly, the sealing member is prevented from sliding relative to tube 304 when tube 304 is moved longitudinally in shell 302 to adjust the length L of the freezing zone while still maintaining a vacuum tight seal separating the freezing zone and the annular space 307.

Figure 28:
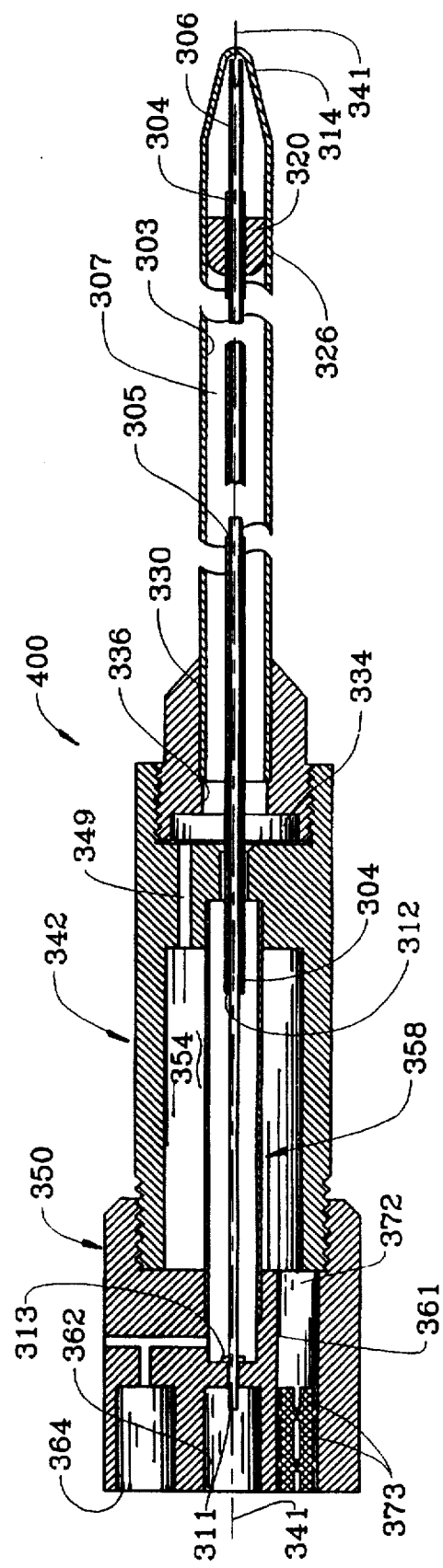
FIG. 28 is a sectional side elevation view of a cryosurgical probe instrument according to the invention including the probe tip of FIG. 17 joined to the probe instrument body of FIG. 26.

The probe's internal $LN_2$ supply tube 306 may include notched region 308 at the distal or outlet end thereof to facilitate flow of $LN_2$ from the supply tube to the freezing zone of the probe tip when the tube 304 is in a fully inserted position (as shown in FIGS. 19 and 28). In the fully inserted position shown in FIGS. 19 and 28, the outlet end 309 of tube 306 will abut against the closed tip end 310. A flange 313 may optionally be provided near the inlet end 311 of supply tube 306 to provide a positive stop to prevent tube 306 from sliding out of the assembled cryoprobe tool (see FIG. 28). If desired, one or more apertures 315 may be provided at the outlet end 309 in addition to or instead of notches 308 to facilitate delivery of $LN_2$ into the freeze zone.

In order to adjust the length L of the freezing zone, it is only necessary to slide the exhaust tube 304 along the longitudinal axis 341 of the probe. The seal member may be moved to the left in FIG. 19 until the front face 322 of the seal abuts against the tapered portion 314 of the shell to reduce the freeze zone or to the right for substantially the length of tube 358 (see e.g. FIG. 28) to increase the length of the freeze zone. For a typical construction in which the probe shell is 8.50 inches long, the exhaust tube is 9.00 inches, the supply tube is 11.40 inches and the hollow tube is 2.125 inches the freeze zone may be adjusted over a range of from about 0.4 to about 2 inches (10 to 50 mm). By increasing the length of the shell, exhaust tube and supply tube to 10.5 inches, 9.25 inches and 13.4 inches, respectively, the freezing zone length may range from about 2 to 4 inches (50 to 100 mm). In practice, there need only be a very small gap between the outside diameter of supply tube 306 and inside diameter of exhaust tube 304. For For example, tube 306 may have an outside diameter of about 0.072 inch and a wall thickness of about 0.010 inch and tube 304 may have an outside diameter of about 0.120 inch and a wall thickness of about 0.020, thereby providing a clearance of about 0.004 inch for the annular channel 305. Therefore, tube 304 is free to move over tube 306 for controlled relocation of the seal member and freeze zone length, and have sufficient clearance to allow exhaust flow in the annular channel 305 of "spent" refrigerant, e.g. $LN_2$ or $N_2(g)$.

Male probe shell 302 is soldered at its proximal end to cylindrical bore 336 of male threaded probe base 330. Preferably, each of the tubes 304, 306, shell 302 and base 330 are fabricated from stainless steel. However, other sterilizable metals which can withstand the cryogenic operating temperature may be used. For example, shell 302 may also be fabricated from copper or other heat conductive metal. Base 330 includes hollow cylindrical region 334 which is in flow communication with axially aligned cylindrical bore 336 and together with annular passageway 307 forms a vacuum insulation zone.

Thermocouple tip 326 or other temperature sensing device may be provided at the periphery of the seal member at or near the interface with the inside wall 303 of the probe shell. The thermocouple tip will be connected by electrical wiring (not shown) to an electrical connector in the probe's instrument body and provides means for measuring the temperature of the probe tip in the freezing zone without being in direct contact with the $LN_2$ refrigerant.

Figure 18A:
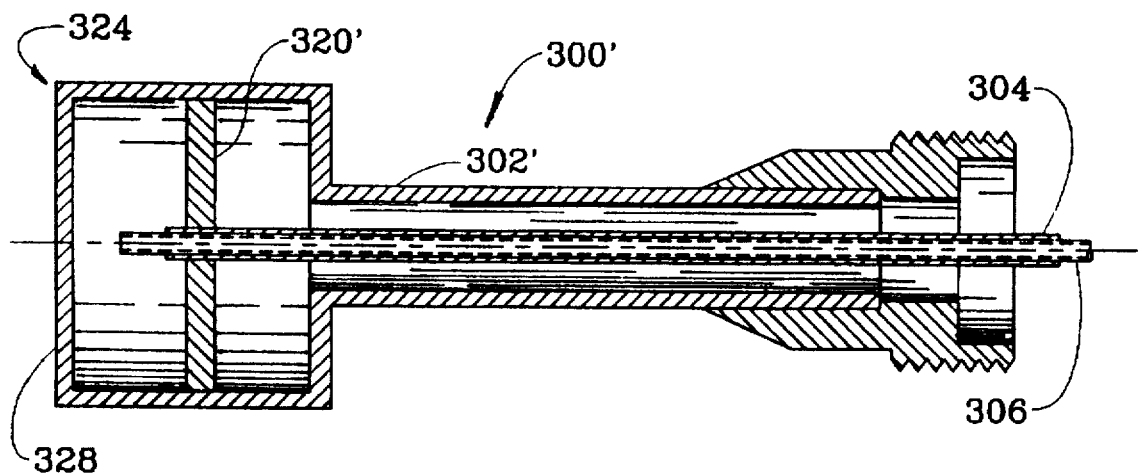
FIG. 18 is a sectional side elevation view of an embodiment of a cryosurgical probe tip according to the invention.
Figure 18B:
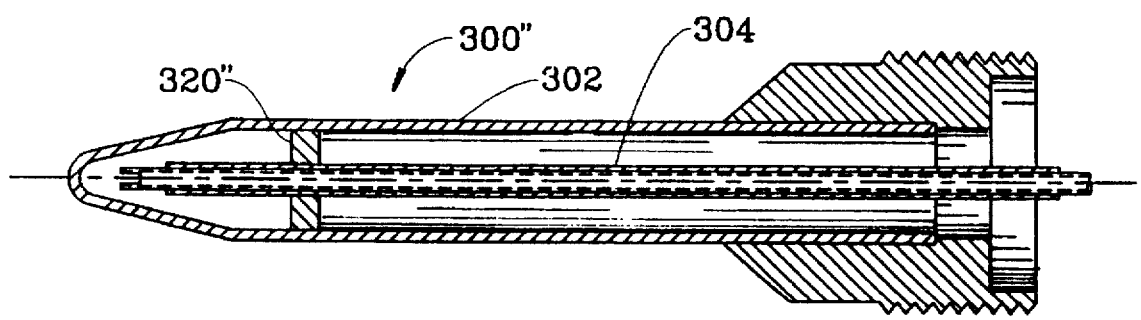
Figure 29:
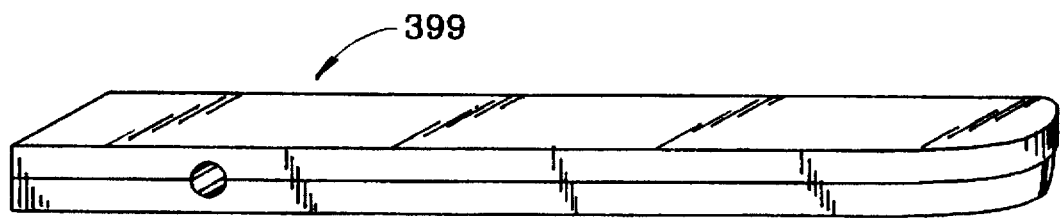
FIG. 29 is a perspective view of a crimping tool for crimping the crimpable seal member shown in FIG. 18-A.

The cryoprobe instrument shown generally at 300" in FIG. 18-B is similar to the cryoprobe 300 in FIG. 18 except that a rigid disc 320" having substantially the same diameter as the inside diameter of probe casing 302 is used as the movable seal member. Disc 320" is used as the movable seal member. Disc 320" is rigidly fixed, for example, by soldering or welding, to exhaust tube 304. After disc 320" is positioned to provide the desired freeze zone at the closed end of the probe casing, a crimping tool 399, such as shown in FIG. 29, may be used to crimp the casing 302 at the location of the sealing member to form a fluid tight seal separatimng the freeze zone from the thermally insulated region behind the seam member.

A modified form of a probe tip is shown in FIG. 18A. The probe tip, shown generally by reference numeral 300' includes a relatively large cylindrical flat faced closed end 324. This configuration of the probe tip may be used advantageously for tumors located on the surface of an organ, such as the liver, especially where the penetration of the tumor is only relatively shallow. Generally, one the flat face 328 is used for freezing and, therefore, the seal member 302' need not be movable but may be permanently secured to the probe casing 302'.

In addition to the probe tip, the cryosurgical tool (also referred to herein as "cryoprobe") according to the invention may also include an instrument body which will provide a handle means for connecting the probe tip to the cryorefrigerant, e.g. $LN_2$, and in the preferred embodiment of the invention to the vacuum source, as well as electrical wiring for providing electrical power to the thermocouple wire. The instrument body should be as compact as possible both to minimize cost and reduce weight for the benefit of the surgeon, while at the same time providing adequate thermal insulation to permit handling notwithstanding the cryogenic temperatures of the refrigerant or the elevated temperature of any heating medium passing therethrough.

Figure 27:
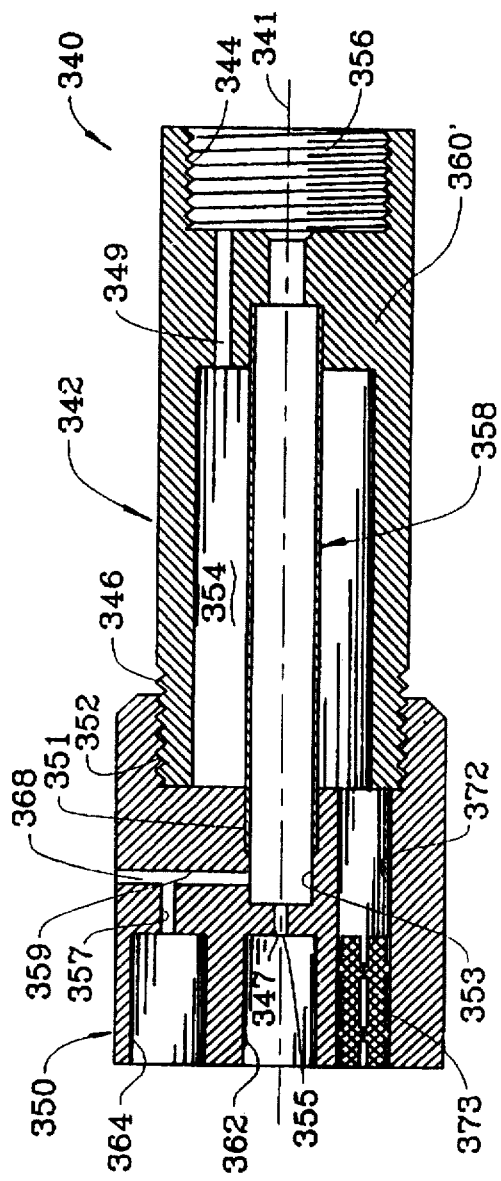
FIG. 27 is a sectional side elevation view of a cryosurgical probe instrument according to the invention including the probe tip of FIG. 17 joined to the probe instrument body of FIG. 21.
Figure 21:
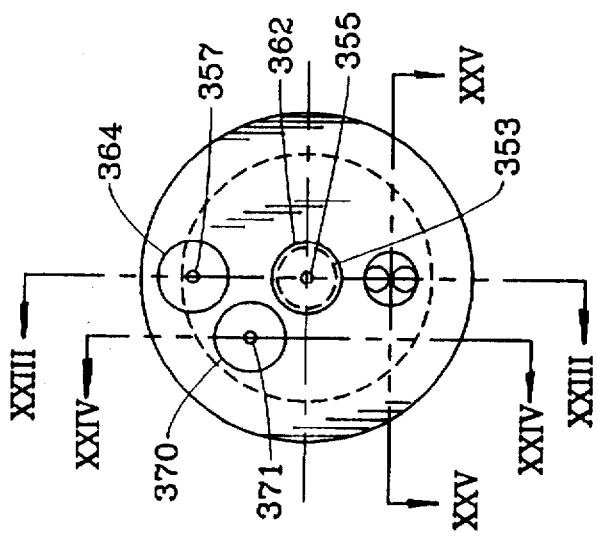

One embodiment of an instrument body is shown generally at 340 in FIG. 27 (see also FIGS. 21–26) and includes a cylindrical probe connector 342 and a cylindrical delivery tube connector 350 having a common cylindrical axis 341. Members 342 and 350 are connected together by the female threaded section 352 of the delivery tube connector and male threaded section 346 of the probe connector after insertion of one end of hollow tube 358 in cylindrical bore 345 in alignment with longitudinal axis 341. When assembled, the other end of tube 358 fits in cylindrical bore 351 which also is in axial alignment with axis 341. Thus, tube 358 forms a portion of the flow passageway for removing refrigerant from the vicinity of the probe tip via the annular passage 305. A second cylindrical bore 347 of smaller cross-section than bore 345 connects the hollow cylindrical portion 354 of probe connector 342 via bore 345 with the hollow female threaded section 356. Section 356, bore 347 and section 354 are also commonly aligned with axis 341. Cylindrical through-bore 349 extends through solid cylindrical body member 360 and has a longitudinal axis which is axially offset from, but in the same plane as, axis 341. Bore 349 provides a passageway connecting space 354 with space 356, and more particularly, when instrument body members 342 and 350 are assembled as shown in FIG. 27 passageway 349 connects the annular space in chamber 354 around tube 358 with region 356.

The delivery tube connector 350 also includes refrigerant inlet opening 362 and a refrigerant outlet opening 364. Inlet 362 is axially aligned with and is connected to bore 351 via bore 353 and a counterbore 355, also commonly aligned with axis 341. Outlet opening 364 is also connected to bore 351 via bore 353 and channels 357 and 359. Channel 359 may conveniently be molded or bored directly through to the outer wall surface 366 of member 350 and in such case, access to the outer wall surface and the atmosphere will be plugged by plug member 368. In a preferred embodiment, probe connector 342 and delivery tube connector 350 as well as plug 358 may be fabricated from Teflon or similar inert sterilizable resin or plastic, preferably with low coefficients of friction and thermal expansion.

Figure 23A:
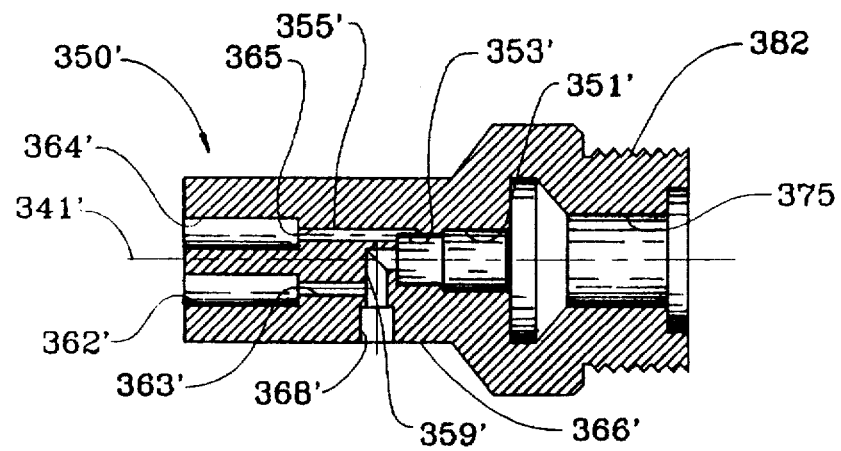
FIG. 23 is a section view along line XXIII—XXIII of FIG. 21.
Figure 24A:
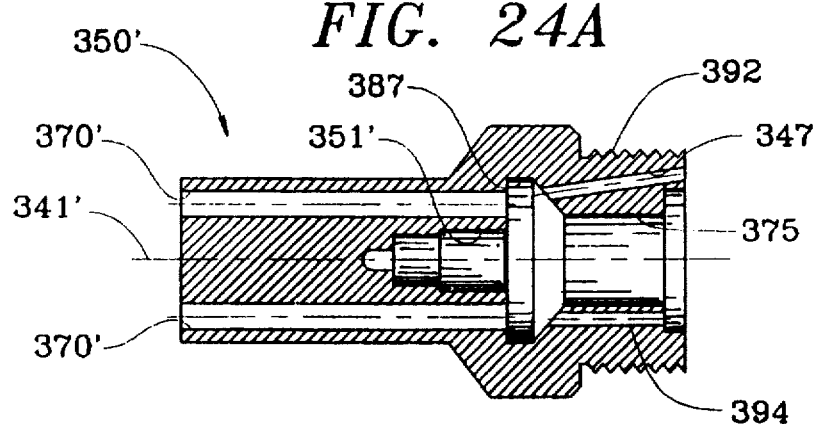
FIG. 24 is a section view along line XXIV—XXIV of FIG. 21.
Figure 21A:
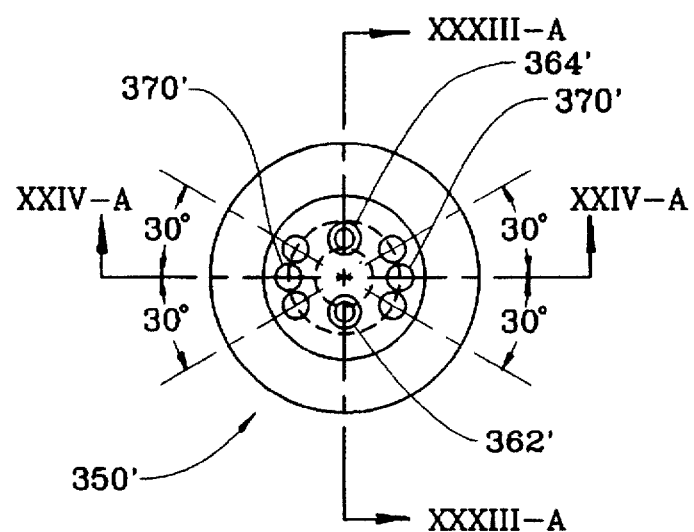
FIG. 21 is a rear end view of an embodiment of a delivery tube connector according to the invention.

As seen in FIGS. 23 and 24 delivery tube connector 350 also includes a vacuum passageway which includes cylindrical bore 370 and narrower cylindrical channel 371, the latter terminating at the hollow female threaded section 352. Through bore 372 in member 350 includes therein female electrical connector 373 for electrical coupling to thermocouple wires (not shown).

To assemble the cryoprobe instrument 400 as shown in FIG. 28, the refrigerant supply tube 306 and exhaust or return tube 304 with attached seal member 320 are slidingly inserted into probe tip shell 302 to an appropriate distance to provide the freezing zone with the predetermined length L. The location of the seal member may be determined by first fully inserting the return tube until the face 322 of member 320 contacts the tapered portion 314 and then withdrawing tube 304 (to the right in FIG. 19) a distance corresponding to the desired movement of seal member 320. Hash marks (not shown) may be provided on the exposed portions of tube 304, for instance at 1/16", 1/8", 1/4" or 1/2" intervals (or, e.g. 2 mm, 5 mm, 8 mm, 10 mm, etc. intervals) to facilitate location of the seal member relative to the closed tip end.

Once the return tube 304 and affixed seal member 320 are adjusted to provide the desired freeze zone length L, the probe tip is engaged with the preassembled instrument body by screwing the female thread portion 344 of member 342 with the male thread portion 332 of probe base 330 such that inlet end 311 of $LN_2$ supply tube 306 extends through cylindrical bore 355 with a fluid tight fit into inlet opening 362 while the outlet end 312 of exhaust tube 304 is located within the refrigerant exhaust passageway provided by tube 358.

Alternatively, the $LN_2$ supply tube, and return tube with affixed seal member are inserted in the probe shell, and probe connector 342 is engaged with the probe base such that the inlet end 311 of the $LN_2$ supply tube extends beyond the free end 361 of tube 358. The protruding inlet end of the $LN_2$ supply tube may then be grasped to move the return tube and affixed seal to locate the seal at the desired position.

For example, the probe tip may be preassembled at the factory, with the return tube and affixed seal being set at a predetermined position and the probe connector attached to the probe base. The delivery tube connector may be attached to the probe connector but more typically will be attached to the delivery tube. In either case, with the delivery tube connector detached from the probe connector, the surgeon may, if desired, readjust the position of the vacuum seal without disengaging the probe connector from the probe tip. For example, a long, thin positioning tool (not shown) including, for example, a calibrated rod having positioning means, such as pincers, at one end thereof adapted to either push or pull tube 304, may be inserted through the annular space 354 between the hollow tube 358 and $LN_2$ supply tube 306 until the moving means contacts the portion of tube 304 extending into the hollow tube 358. The calibrations on the rod can be used to determine the distance that the tube 304 and seal member 320 are moved relative to its original factory preset position.

For a typical cryoprobe instrument according to the invention, the freeze zone length L may be increased from its minimum length by about 3 to 8 cm. When the cryosurgical tool is connected to the refrigerant supply and delivery lines, the refrigerant will travel to the freezing zone via inlet opening 362 and supply tube 306 and flow into the freezing zone via notches 308 and apertures 315 in the outlet end 309. After extracting heat from the shell 302 in the freezing zone the spent refrigerant will be exhausted via the annular channel 305 between tubes 304, 306 and will enter the passageway provided by tube 358 and be withdrawn from the probe connector member 350 via channels 359, 357 and outlet opening 364. Although the seal member 320 may tend to shrink at the cryogenic operating temperatures, since the rubber material is compressed any such shrinkage will be offset by the expansion of the compressed rubber or elastomeric mass forming the seal member, thereby maintaining a fluid tight seal between the freeze zone and the annular space 307 between tube 304 and wall surface 303 behind the seal member forming a thermally insulated vacuum region.

During operation of the cryoprobe an active vacuum may be drawn in the annular space 307 behind the seal member to thermally insulate the outer shell other than in the freeze zone. Similarly, an active vacuum will be drawn in the annular passageway 354 surrounding tube 358 in handle member 342 from an active vacuum source, e.g. vacuum pump and associated vacuum tubing, connected to vacuum passage 370 and channel 351 in communication with passageway 354.

A modified embodiment of an instrument body is shown generally at 340' in FIGS. 27-A (see also FIGS. 21A to 26A) and includes a cylindrical probe connector 342' and a generally cylindrical delivery tube connector 350' having a common cylindrical axis 341'. Members 342' and 350' are connected together by the male threaded section 382 of the delivery tube connector and female threaded section 386 of the probe connector after insertion of one end of hollow tube 358 in cylindrical bore 345' in alignment with longitudinal axis 341'. When assembled, the other end of tube 358 fits in cylindrical bore 351' in the delivery tube connector and which also is in axial alignment with axis 341'. Thus, tube 358 forms a portion of the flow passageway for removing refrigerant from the vicinity of the probe tip via the annular passage 305. A second cylindrical bore 347' of smaller cross-section than bore 345' connects the hollow cylindrical segmented chamber 376 of probe connector 342' via bore 345' with the hollow female threaded section 356'. Section 356', bore 347' and chamber 376 are also commonly aligned with axis 341'. Cylindrical through-bore 349' extends through solid cylindrical body member 360' and has a longitudinal axis which is axially offset from, but in the same plane as, axis 341'. Bore 349' provides a passageway connecting chamber 376 with space 356', and more particularly, when instrument body members 342' and 350' are assembled as shown in FIG. 27A passageway 349' connects the annular space around tube 358 with region 356'.

The delivery tube connector 350' also includes refrigerant inlet passageways 362', 363' and a refrigerant outlet passageways 364', 365'. Inlet 362' is axially offset from but is connected to bore 351' via bore 353' and counterbore 355', all commonly aligned with axis 341', and vertical channel 359'. Outlet 364' is also connected to bore 351' via bore 353' passageway. Channel 359' may conveniently be molded or bored directly through from the outer wall surface 366' of member 350' and in such case, access to the outer wall surface and the atmosphere will be plugged by plug member 368'. Probe connector 342' and delivery tube connector 350' as well as plug 358' may be fabricated from Teflon or similar inert sterilizable resin or plastic, preferably with low coefficients of friction and thermal expansion.

As seen in FIGS. 23-A and 24-A, delivery tube connector 350' also includes a vacuum passageway which includes cylindrical bores 370' which extend through the connector body to communicate with the axially aligned cylindrical bore 387 and cylindrical bore 378. Bores 375 and 387, together with bores 376 and 378 in the probe connector, form a vacuum chamber within the instrument body 340' surrounding hollow tube 358 and the refrigerant flow passageways passing through the instrument body.

Hose connecting barbs 395 and 396 fit within inlet passageway 362' and out passageway 364', respectively, for easy connection to the $LN_2$ supply tube and $LN_2$ return tube in the flexible delivery line.

In this modified embodiment, a molded Teflon probe connector insert 379 sits within cylindrical counter bore 378 of chamber 376. A first ring-shaped probe thermocouple electrical contact 389 is dimensioned to fit with its four projecting legs 391 secured to the outer surface 380 of insert 379 and its inner face 390 abutting against shoulder 381 of insert 379. Protrusions 393 on outer face 392 assure electrical contact with mating first ring-shaped delivery thermocouple electrical contact 389' fitted to the joining face end 361' of the delivery tube connector. Contact 389 and contact 389' are substantially identical in form and size except that contact 389' does not include projections corresponding to projections 393. A second series of mating ring-shaped probe and delivery thermocouple electrical contacts 393 and 393', respectively, and which have the same shapes as, but smaller diameters than, contacts 389 and 389', respectively, fit over face 383 of insert 379 and face end 363' of the delivery tube connector, respectively. Contacts 389, 389' and contacts 393, 393' assure positive, mechanically strong electrical contacts for thermocouple wires (not shown) which are fitted through channels 384 and 385 in insert 379 and through channels 392, 394 in the delivery tube connector and which connect to bore 387. In the probe connector, the thermocouple wire from contact 389 through channel 385 may be wrapped around tube 358 and, together with the thermocouple wire from contact 393 through channel 384, extend through channel 349' and chamber 356 into and through the probe tip to thermocouple 326. Also, the large diameter of ring-shaped contacts 393, 393' will be smaller than the inside diameter (the diameter of the hole or opening) of contacts 389, 389' to avoid electrical contact between contacts 389, 389' and contacts 393, 393'.

Thus, by a very simple arrangement of easily constructed and relatively inexpensive components, the cryosurgical tool of this invention may include a variable freezing zone in the probe tip and an active vacuum insulation. Even if there is a leak in seal member 320 or elsewhere, e.g. at the screwed connection between probe base 330 and probe connector 342, 342' or between probe connector 342 or 342' and delivery tube connector 350 or 350', the active vacuum insulation will still be maintained and the surgical procedure will not need to be disrupted.

Also, while the probe tip components including shell 302 and $LN_2$ supply tube, return tube and affixed seal member and the instrument body may be re-sterilized after use, and reused one or more times, it is a particular advantage of the invention that each of the cryoprobe components may be made sufficiently inexpensively and without requiring expensive complicated machining or welding of the seal member that it becomes practical for the first time to provide the probe tip and instrument body components for single use only, to be discarded after each use.

While there has been described what are considered to be preferred embodiments of the invention, other variations and modifications therein may occur to those skilled in the art once they become acquainted with the basic concepts of the invention. Therefore, it is intended that the appended claims shall be construed to include all such variations and modifications as fall within the true spirit and scope of the invention.

What is claimed is:

1. A surgical system for use in producing very low temperature sufficient to destroy living tissue, comprising a source of pressurized cryogenic liquid refrigerant means for sub-cooling the pressurized cryogenic liquid refrigerant, at least one closed end type cryosurgical instrument having a hollow probe tip with an opening at one end for receiving liquid refrigerant, a closed second end for freezing living tissue, a first passageway providing an internal supply line for carrying the pressurized liquid refrigerant from the opened end to the closed second end, a second passageway providing a return line for carrying the refrigerant from the closed end to outside of the instrument, an external supply line for delivering the sub-cooled pressurized liquid refrigerant to the closed second end of the hollow probe tip through the first passageway, and thermal insulation surrounding at least a portion of the first passageway, whereby during use of the system to destroy unhealthy or undesired living tissue the pressurized cryogenic liquid refrigerant is sub-cooled by the sub-cooling means and the sub-cooled pressurized cryogenic liquid refrigerant is transported to the closed second end to cause heat transfer across the closed second end of the probe tip to result in freezing and destruction of the living tissue in contact with the closed second end.

2. The surgical system of claim 1 wherein said heat exchange device comprises coiled metal tubing forming an elongated heat exchange flow path within said vacuum chamber.

3. The surgical system of claim 2 which comprises a plurality of said heat exchange devices, said vacuum chamber having an inlet and an outlet for each heat exchange device.

4. The surgical system of claim 3 wherein the vacuum chamber further comprises inlet means for feeding liquid nitrogen into said receptacle, and a pre-cooling heat exchanger connected at one end thereof to said inlet means and the other end thereof discharging into said receptacle.

5. The surgical system of claim 1 wherein the hollow probe tip is of the closed end type, said second end being closed and the cryosurgical instrument further including a second passageway providing a return line for carrying the refrigerant from the closed end to outside of the instrument.

6. A surgical system for use in producing very low temperature sufficient to destroy living tissue, comprising a source of cryogenic liquid refrigerant, means for evaporatively sub-cooling the cryogenic liquid refrigerant, at least one cryosurgical instrument having a hollow probe tip with an opening at one end for receiving liquid refrigerant, a second end for freezing living tissue, and a first passageway providing an internal supply line for carrying the liquid refrigerant from the open end to the second end, an external supply line for delivering the sub-cooled liquid refrigerant to the second end of the hollow probe tip through the first passageway, and thermal insulation surrounding at least a portion of the first passageway, wherein the means for evaporatively sub-cooling the liquid nitrogen comprises a vacuum chamber having a receptacle therein for storing liquid nitrogen, means for withdrawing gas from the vacuum chamber to reduce the pressure thereof to as low as about 1.81 psia to evaporatively cool the liquid nitrogen in the receptacle, whereby the temperature of the liquid nitrogen in the receptacle is lowered to below the normal boiling temperature of liquid nitrogen, and means for transporting the evaporatively cooled liquid nitrogen to the internal supply line for carrying the liquid refrigerant to the second end of the hollow probe tip.

7. The surgical system of claim 6 wherein the hollow probe tip is of the closed end type, said second end being closed and the cryosurgical instrument further including a second passageway providing a return line for carrying the refrigerant from the closed end to outside of the instrument.

8. The surgical system of claim 6 wherein the means for transporting the evaporatively cooled liquid nitrogen comprises a liquid cryogen pump.

9. The surgical system of claim 8 wherein the means for transporting the evaporatively cooled liquid nitrogen comprises a source of high pressure nitrogen gas, a conduit connecting the source of high pressure gas to the vacuum chamber containing the evaporatively cooled liquid nitrogen and a delivery line connecting the pressurized evaporatively cooled liquid nitrogen to the internal supply line for carrying the liquid refrigerant to the second end of the hollow probe tip.

10. The surgical system of claim 9 wherein the second end of the hollow probe tip is closed, said cryosurgical instrument further including a second passageway providing a return line for carrying the refrigerant from the closed end to outside of the instrument.

* * * * *

UNITED STATES PATENT AND TRADEMARK OFFICE
CERTIFICATE OF CORRECTION

| | | |
|---|---|---|
| PATENT NO. | : 5,674,218 | |
| APPLICATION NO. | : 08/390371 | |
| DATED | : October 7, 1997 | |
| INVENTOR(S) | : Boris Rubinsky et al. | |

It is certified that error appears in the above-identified patent and that said Letters Patent is hereby corrected as shown below:

At Col. 46, lines 15 - 38, replace the following:

"A surgical system for use in producing very low temperature sufficient to destroy living tissue, comprising a source of pressurized cryogenic liquid refrigerant means for sub-cooling the pressurized cryogenic liquid refrigerant, at least one closed end type cryosurgical instrument having a hollow probe tip with an opening at one end for receiving liquid refrigerant, a closed second end for freezing living tissue, a first passageway providing an internal supply line for carrying the pressurized liquid refrigerant from the opened end to the closed second end, a second passageway providing a return line for carrying the refrigerant from the closed end to outside of the instrument, an external supply line for delivering the sub-cooled pressurized liquid refrigerant to the closed second end of the hollow probe tip through the first passageway, and thermal insulation surrounding at least a portion of the first passageway, whereby during use of the system to destroy unhealthy or undesired living tissue the pressurized cryogenic liquid refrigerant is sub-cooled by the sub-cooling means and the sub-cooled pressurized cryogenic liquid refrigerant is transported to the closed second end to cause heat transfer across the closed second end of the probe tip to result in freezing and destruction of the living tissue in contact with the closed second end."

with

--A surgical system for use in producing very low temperature sufficient to destroy living tissue, comprising a source of cryogenic liquid refrigerant, means for evaporatively sub-cooling the cryogenic liquid refrigerant, at least one cryosurgical instrument having a hollow probe tip with an opening at one end for receiving liquid refrigerant, a second end for freezing living tissue, and a first passageway providing an internal supply line for carrying the liquid refrigerant from the open end to the second end, an external supply line for delivering the sub-cooled liquid refrigerant to the second end of the hollow probe tip through the first passageway, and thermal insulation surrounding at least a portion of the first passageway, wherein the means for evaporatively sub-cooling comprises--

Signed and Sealed this
Twenty-first Day of June, 2011

David J. Kappos
*Director of the United States Patent and Trademark Office*

UNITED STATES PATENT AND TRADEMARK OFFICE
CERTIFICATE OF CORRECTION

| | |
|---|---|
| PATENT NO. | : 5,674,218 |
| APPLICATION NO. | : 08/390371 |
| DATED | : October 7, 1997 |
| INVENTOR(S) | : Boris Rubinsky et al. |

It is certified that error appears in the above-identified patent and that said Letters Patent is hereby corrected as shown below:

At Col. 46, lines 15 - 38, replace the following:

"A surgical system for use in producing very low temperature sufficient to destroy living tissue, comprising a source of pressurized cryogenic liquid refrigerant means for sub-cooling the pressurized cryogenic liquid refrigerant, at least one closed end type cryosurgical instrument having a hollow probe tip with an opening at one end for receiving liquid refrigerant, a closed second end for freezing living tissue, a first passageway providing an internal supply line for carrying the pressurized liquid refrigerant from the opened end to the closed second end, a second passageway providing a return line for carrying the refrigerant from the closed end to outside of the instrument, an external supply line for delivering the sub-cooled pressurized liquid refrigerant to the closed second end of the hollow probe tip through the first passageway, and thermal insulation surrounding at least a portion of the first passageway, whereby during use of the system to destroy unhealthy or undesired living tissue the pressurized cryogenic liquid refrigerant is sub-cooled by the sub-cooling means and the sub-cooled pressurized cryogenic liquid refrigerant is transported to the closed second end to cause heat transfer across the closed second end of the probe tip to result in freezing and destruction of the living tissue in contact with the closed second end."

with

--A surgical system for use in producing very low temperature sufficient to destroy living tissue, comprising a source of cryogenic liquid refrigerant, means for evaporatively sub-cooling the cryogenic liquid refrigerant, at least one cryosurgical instrument having a hollow probe tip with an opening at one end for receiving liquid refrigerant, a second end for freezing living tissue, and a first passageway providing an internal supply line for carrying the liquid refrigerant from the open end to the second end, an external supply line for delivering the sub-cooled liquid refrigerant to the second end of the hollow probe tip through the first passageway, and thermal insulation surrounding at least a portion of the first passageway, wherein the means for evaporatively sub-cooling comprises:

This certificate supersedes the Certificate of Correction issued June 21, 2011.

Signed and Sealed this
Seventeenth Day of April, 2012

David J. Kappos
*Director of the United States Patent and Trademark Office* a source of liquid nitrogen, a vacuum chamber having an inlet for receiving liquid nitrogen from the source, and an outlet for transferring sub-cooled liquid nitrogen to the external supply line, means for withdrawing gas from the vacuum chamber to lower the pressure therein, a receptacle for storing liquid nitrogen within the vacuum chamber, a heat exchange device within the receptacle connected at one end thereof to the inlet of the vacuum chamber and at the opposite end thereof to the outlet of the vacuum chamber, and a conduit connecting the source of liquid nitrogen to the vacuum chamber inlet, whereby in operation a vacuum is generated in the vacuum chamber to cause liquid nitrogen in the receptacle to form sub-cooled liquid nitrogen, such that liquid nitrogen flowing through the heat exchange device in heat exchange contact with the sub-cooled liquid nitrogen has its temperature lowered to below the normal boiling temperature of nitrogen.--